United States Patent
Lee et al.

(10) Patent No.: US 10,150,911 B2
(45) Date of Patent: Dec. 11, 2018

(54) METAL COMPLEX AND COLOR CONVERSION FILM COMPRISING SAME

(71) Applicant: LG CHEM, LTD., Seoul (KR)

(72) Inventors: Hoyong Lee, Daejeon (KR); Kichul Koo, Daejeon (KR); Minyoung Kang, Daejeon (KR); Duy hieu Le, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/540,474

(22) PCT Filed: Dec. 22, 2015

(86) PCT No.: PCT/KR2015/014131
§ 371 (c)(1),
(2) Date: Jun. 28, 2017

(87) PCT Pub. No.: WO2016/122117
PCT Pub. Date: Aug. 4, 2016

(65) Prior Publication Data
US 2017/0349822 A1   Dec. 7, 2017

(30) Foreign Application Priority Data

Jan. 27, 2015 (KR) .................. 10-2015-0013046
Mar. 20, 2015 (KR) .................. 10-2015-0039059

(51) Int. Cl.
*C07F 5/02* (2006.01)
*C09K 11/06* (2006.01)
(Continued)

(52) U.S. Cl.
CPC .............. *C09K 11/06* (2013.01); *C07F 5/02* (2013.01); *C07F 5/022* (2013.01); *C08K 5/55* (2013.01);
(Continued)

(58) Field of Classification Search
CPC .................. C09K 11/06; C09K 11/02; C09K 2211/1022; C09K 2211/1007;
(Continued)

(56) References Cited

U.S. PATENT DOCUMENTS 6,337,536 B1    1/2002  Matsubara et al.
2010/0213356 A1* 8/2010  Berginc ............... G02F 1/3523
                                                           250/226
(Continued)

FOREIGN PATENT DOCUMENTS

EP    1253151 A1   10/2002
JP    2004-200162 A  7/2004
(Continued)

OTHER PUBLICATIONS

Loudet, Aurore, et al., BODIPY Dyes and Their Derivatives: Synthesis and Spectroscopic Properties, Oct. 2007, Chem. Rev., 107, 4891-4932.*

(Continued)

*Primary Examiner* — Eli D. Strah
(74) *Attorney, Agent, or Firm* — Dentons US LLP

(57) ABSTRACT

The present specification relates to a novel compound, and a color conversion film, a backlight unit, and a display device, comprising the same.

13 Claims, 2 Drawing Sheets

(51) Int. Cl.
　　　*G02F 1/1335*　　(2006.01)
　　　*F21K 9/64*　　(2016.01)
　　　*F21V 9/30*　　(2018.01)
　　　*C08K 5/55*　　(2006.01)
　　　*C09K 11/02*　　(2006.01)
　　　*C09B 23/04*　　(2006.01)
　　　*C09B 57/00*　　(2006.01)
　　　*C09B 57/10*　　(2006.01)
　　　*B32B 17/10*　　(2006.01)
　　　*H01L 51/00*　　(2006.01)
(52) U.S. Cl.
　　　CPC .............. *C09B 23/04* (2013.01); *C09B 57/00* (2013.01); *C09B 57/10* (2013.01); *C09K 11/02* (2013.01); *F21K 9/64* (2016.08); *F21V 9/30* (2018.02); *G02F 1/1335* (2013.01); *B32B 17/10669* (2013.01); *B32B 2307/422* (2013.01); *B32B 2457/206* (2013.01); *C09K 2211/1007* (2013.01); *C09K 2211/1011* (2013.01); *C09K 2211/1022* (2013.01); *H01L 51/008* (2013.01)
(58) Field of Classification Search
　　　CPC ..... C09K 2211/1011; F21V 9/30; F21K 9/64; C08K 5/55; C07F 5/022; H01L 51/008; B32B 2457/206; B32B 17/10669; B32B 2307/422
　　　See application file for complete search history.

(56) References Cited

U.S. PATENT DOCUMENTS

| | | |
|---|---|---|
| 2012/0037890 A1 | 2/2012 | Okuda et al. |
| 2012/0091883 A1* | 4/2012 | Nagai ................... C09K 11/06 313/504 |
| 2016/0284947 A1 | 9/2016 | Koenemann et al. |

FOREIGN PATENT DOCUMENTS

| | | | |
|---|---|---|---|
| JP | 2007-273440 A | 10/2007 | |
| JP | 4827434 B2 | 11/2011 | |
| JP | 2011-241160 A | 12/2011 | |
| KR | 10-2000-0011622 A | 2/2000 | |
| KR | 10-2008-0044160 A | 5/2008 | |
| KR | 10-2013-0129543 A | 11/2013 | |
| KR | 10-2014-0051214 A | 4/2014 | |
| WO | WO 2015/006374 A1 * | 1/2015 | ............ B82Y 30/00 |

OTHER PUBLICATIONS

"BODIPY Dyes and Their Derivatives: Syntheses and Spectroscopic Properties"; Loudet, et al; 2007 American Chemical Society, 107, 4891-4932.
"A Modular Synthesis of Unsymmetrical Tetraarylazadipyrromethenes"; Hall, et al.; J. Org. Chem., vol. 70, No. 14, 2005.
"A General Synthetic Strategy for the Design of New BODIPY Fluorophores Based on Pyrroles with Polycondensed Aromatic and Metallocene ACHTUNGTRENUNGSubstituents"; Schmidt, et al.; Chem. Eur. J. 2011, 17, 3069-3073.
"Red-emissive Polyphenylated BODIPY Derivatives:Effect of Peripheral Phenyl Groups on the Photophysical and Electrochemical Properties"; Wakamiya, et al.; Chemistry Letters vol. 37, No. 10 (2008).
M. Mao et al., "Highly efficient light-harvesting boradiazaindacene sensitizers for dye-sensitized solar cells featuring phenothiazine donor antenna," Journal of Power Sources, 2014, vol. 268, pp. 965-976.

* cited by examiner

[Figure 1]
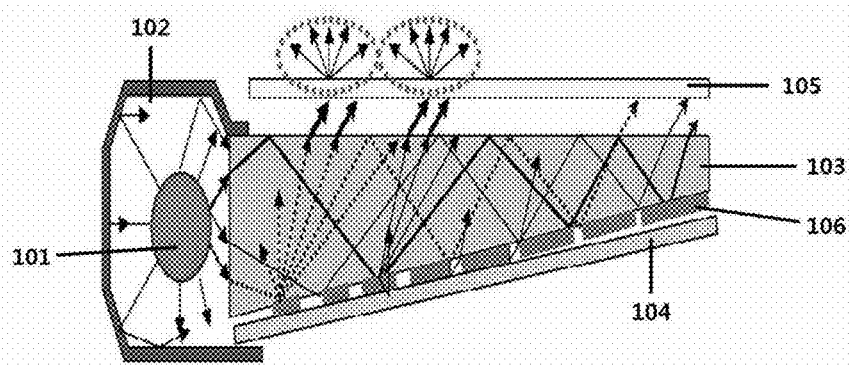
[Figure 2]
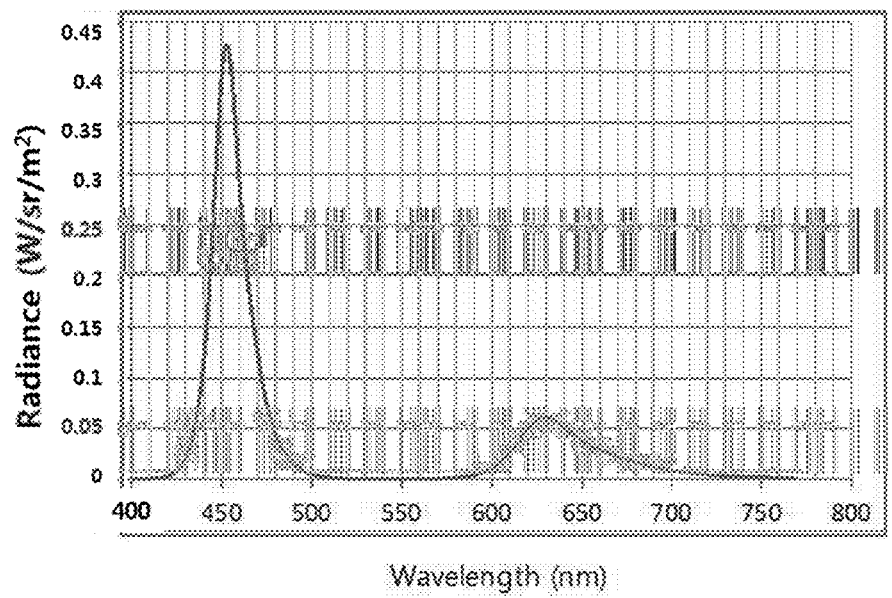

[Figure 3]
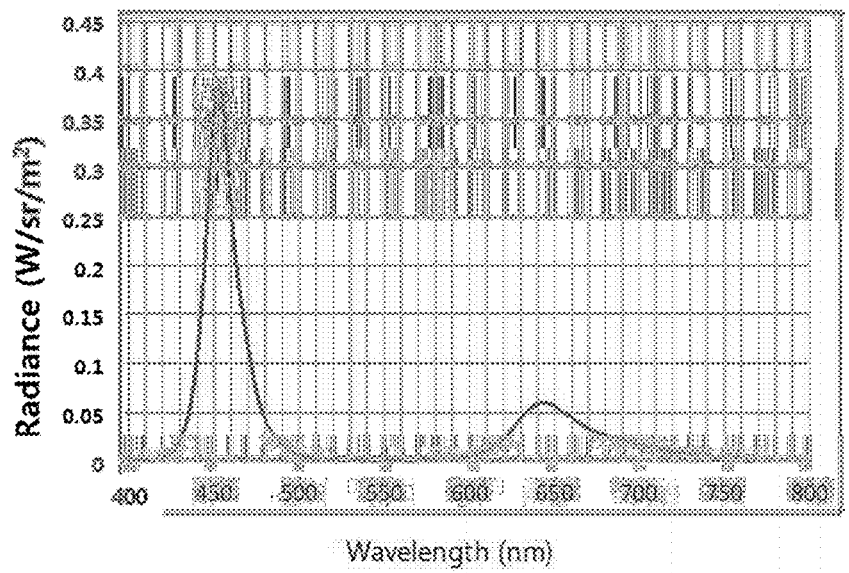
[Figure 4]
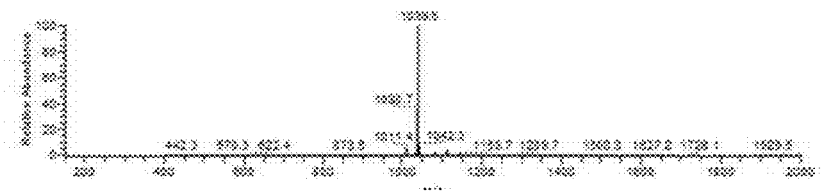
[Figure 5]
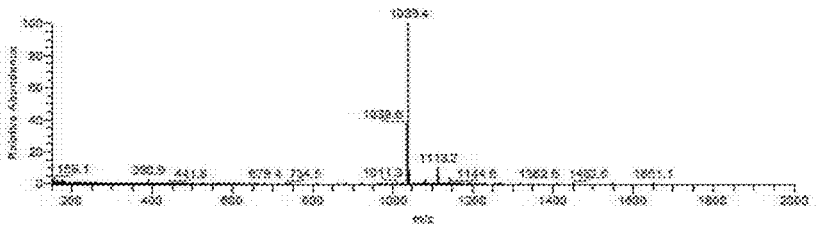

METAL COMPLEX AND COLOR CONVERSION FILM COMPRISING SAME

TECHNICAL FIELD

This application is a National Stage Entry of International Application No. PCT/KR2015/014131, filed on Dec. 22, 2015, and claims the benefit of and priority to Korean Application No. 10-2015-0013046, filed on Jan. 27, 2015, and Korean Application No. 10-2015-0039059, filed on Mar. 20, 2015 all of which are hereby incorporated by reference in their entirety for all purposes as if fully set forth herein.

The present specification relates to a novel metal complex and a color conversion film comprising the same. The present specification also relates to a backlight unit and a display device, comprising the color conversion film.

BACKGROUND ART

The existing light emitting diodes (LEDs) are obtained by mixing a green phosphor and a red phosphor with a blue light emitting diode or mixing a yellow phosphor and a blue-green phosphor with a UV light emission light emitting diode. However, in this method, it is difficult to control colors, and accordingly, the color rendition is not good. Therefore, the color gamut deteriorates.

In order to overcome the deterioration in color gamut and reduce the production costs, methods of implementing green and red colors have been recently attempted by using a method of producing a quantum dot in the form of a film and combining the same with a blue LED. However, cadmium-based quantum dots have safety problems, and the other quantum dots have much lower efficiencies than those of the cadmium-based quantum dots. Further, quantum dots have low stability against oxygen and water, and have a disadvantage in that the performance thereof significantly deteriorates when the quantum dots are aggregated. In addition, when quantum dots are produced, it is difficult to maintain the size thereof at a certain level, and thus, the production cost is high.

CITATION LIST

[Patent Document]

(Patent Document 1) Korean Patent Application Laid-Open No. 2000-0011622

DISCLOSURE

Technical Problem

The present specification provides a novel metal complex and a color conversion film comprising the same. Further, the present specification provides a backlight unit and a display device, comprising the color conversion film.

Technical Solution

According to an exemplary embodiment of the present specification, provided is a compound represented by the following Chemical Formula 1.

[Chemical Formula 1]

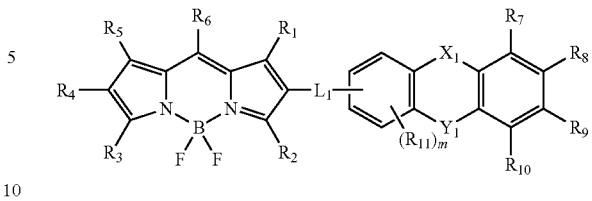

In Chemical Formula 1, $L_1$ is a direct bond; a substituted or unsubstituted alkylene group; or a substituted or unsubstituted arylene group, $X_1$ is $CR_{12}R_{13}$, $NR_{14}$, O, or S, $Y_1$ is a direct bond, $CR_{15}R_{16}$, $NR_{17}$, O, or S, $R_1$ to $R_{17}$ are the same as or different from each other, and are each independently hydrogen; deuterium; a halogen group; a nitrile group; a nitro group; a carbonyl group; a carboxyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted amine group; a substituted or unsubstituted aryl group; or a substituted or unsubstituted heterocyclic group, or any adjacent two of $R_7$ to $R_{10}$ may be linked to each other to form a substituted or unsubstituted hydrocarbon ring; or a substituted or unsubstituted hetero ring, and m is an integer of 1 to 3.

According to another exemplary embodiment of the present specification, provided is a color conversion film comprising: a resin matrix; and the compound represented by Chemical Formula 1, which is dispersed in the resin matrix.

According to still another exemplary embodiment of the present specification, provided is a backlight unit comprising the color conversion film.

According to yet another exemplary embodiment of the present specification, provided is a display device comprising the backlight unit.

Advantageous Effects

The metal complex described in the present specification has high fluorescence efficiency, is stable against water or oxygen, and has lower production cost than those of quantum dots. Therefore, by using the metal complex described in the present specification as a fluorescent material of a color conversion film, it is possible to provide a color conversion film of which brightness and color gamut are excellent, the production process is simple, and production cost is low.

DESCRIPTION OF DRAWINGS

FIG. 1 is a schematic view in which a color conversion film according to an exemplary embodiment of the present specification is applied to a backlight unit.

FIG. 2 is a light emitting spectrum of a color conversion film produced in Example 1.

FIG. 3 is a light emitting spectrum of a color conversion film produced in Example 3.

FIG. 4 is NMR spectra of Compounds 1-60 produced in Preparation Example 16.

FIG. 5 is NMR spectra of Compounds 1-62 produced in Preparation Example 18.

BEST MODE

Hereinafter, the present specification will be described in more detail.

A color conversion film according to an exemplary embodiment of the present specification provides the compound represented by Chemical Formula 1.

The compound represented by Chemical Formula 1 has a high glass transition temperature as a condensed ring group comprising a pentacyclic or hexacyclic ring is introduced as a substituent into a boron-dipyrromethene metal complex core. Accordingly, thermal stability may be secured.

Furthermore, an intermolecular stacking of the boron-dipyrromethene metal complex core structure may be reduced by introducing a condensed ring group comprising a pentacyclic or hexacyclic ring as a substituent into the boron-dipyrromethene metal complex core structure of the compound represented by Chemical Formula 1, thereby preventing the aggregation. Preferably, the effect is further increased when a condensed ring group comprising a pentacyclic or hexacyclic ring is introduced as a substituent into the 2- or 8-position of the above-described Chemical Formula 1; or the 2- and 8-positions of Chemical Formula 2 to be described below. Accordingly, the color conversion film comprising the compound represented by Chemical Formula 1 is formed, and then there are effects of increasing the fluorescence efficiency and reducing the full width at half maximum.

According to an exemplary embodiment of the present specification, the compound represented by Chemical Formula 1 may be represented by the following Chemical Formula 2.

or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted amine group; a substituted or unsubstituted aryl group; or a substituted or unsubstituted heterocyclic group, or any adjacent two of $R_{18}$ to $R_{21}$ may be linked to each other to form a substituted or unsubstituted hydrocarbon ring; or a substituted or unsubstituted hetero ring, and n is an integer of 1 to 3.

According to an exemplary embodiment of the present specification, the compound represented by Chemical Formula 1 may absorb blue light according to the substituent to emit green light or red light.

According to an exemplary embodiment of the present specification, the compound represented by Chemical Formula 1 may simultaneously absorb blue light and green light to emit red light.

According to an exemplary embodiment of the present specification, the compound represented by Chemical Formula 1 may be represented by the following Chemical Formula 3.

[Chemical Formula 3]

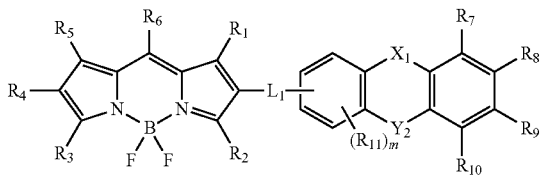

In Chemical Formula 3, the definitions of $L_1$, $X_1$, $R_1$ to $R_{11}$, and m are the same as those in Chemical Formula 1, $Y_2$ is $CR_{15}R_{16}$, $NR_{17}$, O, or S, and the definitions of $R_{15}$ to $R_{17}$ are the same as those in Chemical Formula 1.

According to an exemplary embodiment of the present specification, the compound represented by Chemical Formula 1 may be represented by the following Chemical Formula 4.

[Chemical Formula 2]

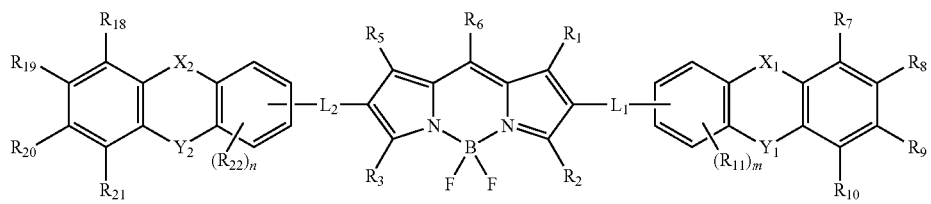

In Chemical Formula 2, the definitions of $L_1$, $X_1$, $Y_1$, $R_1$ to $R_3$, $R_5$ to $R_{11}$, and m are the same as those in Chemical Formula 1, $L_2$ is a direct bond; a substituted or unsubstituted alkylene group; or a substituted or unsubstituted arylene group, $X_2$ is $CR_{23}R_{24}$, $NR_{25}$, O, or S, $Y_2$ is a direct bond, $CR_{26}R_{27}$, $NR_{28}$, O, or S $R_{18}$ to $R_{28}$ are the same as or different from each other, and are each independently hydrogen; deuterium; a halogen group; a nitrile group; a nitro group; a carbonyl group; a carboxyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted

[Chemical Formula 4]

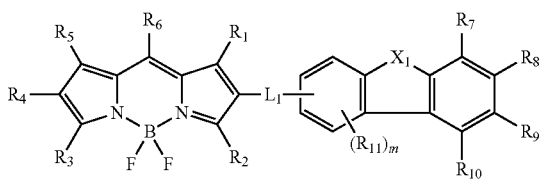

In Chemical Formula 4, the definitions of $L_1$, $X_1$, $R_1$ to $R_{11}$, and m are the same as those in Chemical Formula 1, According to an exemplary embodiment of the present specification, the compound represented by Chemical Formula 4 may be represented by any one of the following Chemical Formulae 4-1 to 4-4.

[Chemical Formula 4-1]
[Chemical Formula 4-2]
[Chemical Formula 4-3]
[Chemical Formula 4-4]

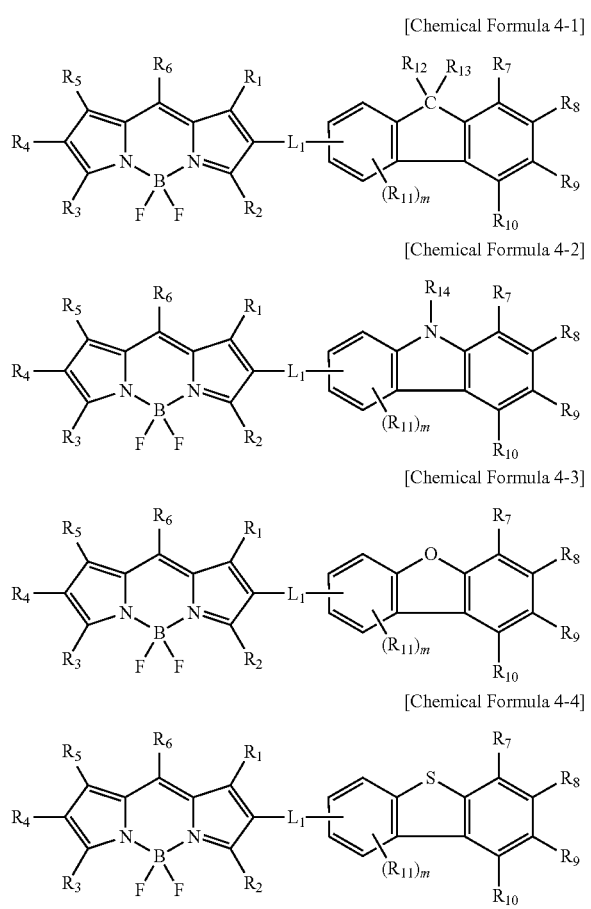

In Chemical Formulae 4-1 to 4-4, the definitions of $L_1$, $R_1$ to $R_{14}$, and m are the same as those in Chemical Formula 1, According to an exemplary embodiment, in the compound represented by Chemical Formula 1, the maximum light emission peak in a film state is present within 520 nm to 550 nm. The compound as described above emits green light.

According to an exemplary embodiment, in the compound represented by Chemical Formula 1, the maximum light emission peak in a film state is present within 520 nm to 550 nm, and the full width at half maximum of the light emission peak is 50 nm or less. In the case of having a narrow full width at half maximum as described above, the color gamut may be further increased. In this case, the narrower the full width at half maximum of the light emission peak of the compound represented by Chemical Formula 1 is, the better is the color gamut is.

According to an exemplary embodiment, in the compound represented by Chemical Formula 1, the maximum light emission peak in a film state is present within 610 nm to 650 nm. The compound as described above emits red light.

According to an exemplary embodiment, in the compound represented by Chemical Formula 1, the maximum light emission peak in a film state is present within 610 nm to 650 nm, and the full width at half maximum of the light emission peak is 60 nm or less. In the case of having a narrow full width at half maximum as described above, the color gamut may be further increased. In this case, the full width at half maximum of the light emission peak of the compound represented by Chemical Formula 1 may be 5 nm or more.

According to an exemplary embodiment, the compound represented by Chemical Formula 1 has a quantum efficiency of 0.9 or more.

In the present specification, "a film state" does not mean a solution state, but means a state produced in the form of a film by using the compound represented by Chemical Formula 1 alone or mixing the compound with other components which does not affect the measurement of the full width at half maximum and the quantum efficiency.

In the present specification, the full width at half maximum means a width of the light emission peak when the height is half the maximum height in the maximum light emission peak of light emitted from the compound represented by Chemical Formula 1.

In the present specification, the quantum efficiency may be measured by using a method known in the art, and may be measured by using, for example, an integrating sphere.

Examples of the substituents of Chemical Formula 1 will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a sulfonate group; a carboxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, in a carbonyl group, (—C═O) may be substituted with a straight-chained, branched, or cyclic alkyl group having 1 to 25 carbon atoms, or an aryl group having 6 to 25 carbon atoms.

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

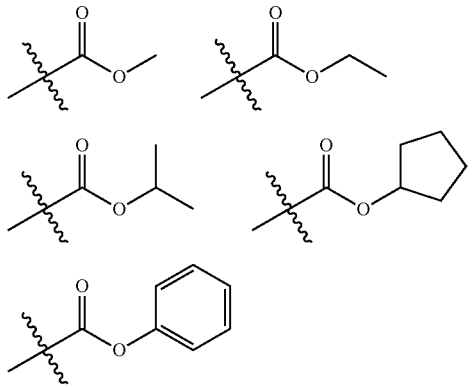

In the present specification, the number of carbon atoms of an imide group is not particularly limited, but is preferably 1 to 25. Specifically, the imide group may be a compound having the following structures, but is not limited thereto.

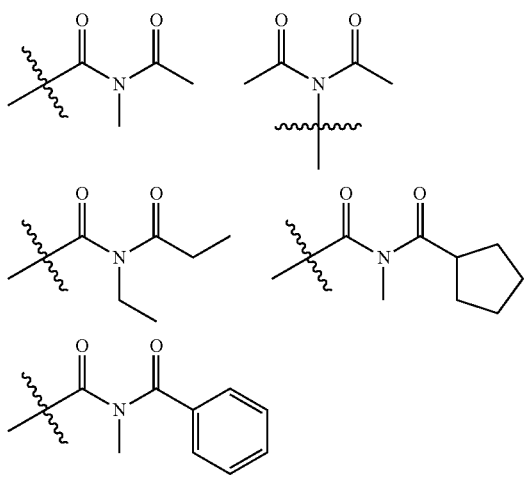

In the present specification, in an amide group, one or two nitrogen atoms of the amide group may be substituted with hydrogen, a straight-chained, branched, or cyclic alkyl group having 1 to 25 carbon atoms, or an aryl group having 6 to 25 carbon atoms. Specifically, the amide group may be a compound having the following structural formulae, but is not limited thereto.

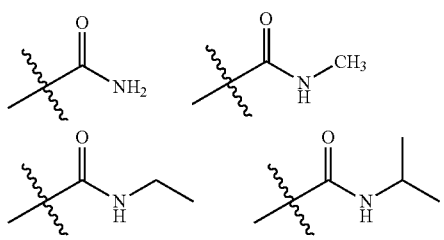

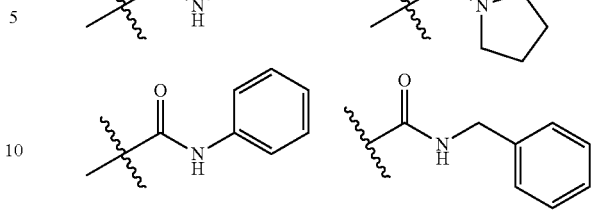

In the present specification, a sulfonate group may be expressed as —$SO_3X$, and X may be hydrogen or an element of Group 1. Examples of the sulfonate group include —$SO_3Na$.

In the present specification, a carboxyl group may be represented by —$R_{100}C(=O)$ OH, $R_{100}$ may be a substituted or unsubstituted alkylene group; a substituted or unsubstituted arylene group; a substituted or unsubstituted alkenylene group; or a substituted or unsubstituted heteroarylene group, and the carboxyl group may be substituted with a straight-chained, branched, or cyclic alkyl group having 1 to 25 carbon atoms, or an aryl group having 6 to 25 carbon atoms.

In the present specification, an alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, n-decanyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, an aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, a quaterphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

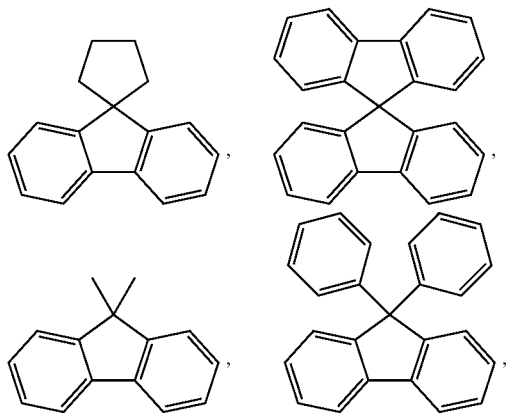

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, a silyl group may be represented by —SiRR'R", and R, R', and R" may be each independently hydrogen, a straight-chained, branched, or cyclic alkyl group having 1 to 25 carbon atoms, or an aryl group having 6 to 25 carbon atoms. Specific examples thereof include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by —BRR'R", and R, R', and R" may be each independently hydrogen, a straight-chained, branched, or cyclic alkyl group having 1 to 25 carbon atoms, or an aryl group having 6 to 25 carbon atoms.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including the two or more aryl groups may include a monocyclic aryl group, a polycyclic aryl group, or both a monocyclic aryl group and a polycyclic aryl group.

In the present specification, a heterocyclic group is a heterocyclic group including one or more of O, N, and S as a hetero element, and the number of carbon atoms thereof is not particularly limited, but is preferably 2 to 60. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, an aryl group in an aryloxy group, an arylthioxy group, an arylsulfoxy group, and an aralkylamine group is the same as the above-described examples of the aryl group. Specifically, examples of a haloaryl group include a fluoroaryl group, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, an alkyl group in an alkylthioxy group and an alkylsulfoxy group is the same as the above-described examples of the alkyl group. Specifically, examples of a haloalkyl group include a fluoroalkyl group, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, an alkylene group means that there are two bonding positions in an alkyl group, that is, a divalent group. The above-described description on the alkyl group may be applied, except that the alkylene groups are each a divalent group.

In the present specification, an arylene group means that there are two bonding positions in an aryl group, that is, a divalent group. The above-described description on the aryl group may be applied, except that the arylene groups are each a divalent group.

In the present specification, a hydrocarbon ring may be an aromatic ring, an aliphatic ring, or a condensed ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more of an atom other than carbon, that is, a heteroatom, and specifically, the heteroatom may include one or more atoms selected from the group consisting of O, N, Se, and S, and the like. The hetero ring may be monocyclic or polycyclic, may be an aromatic ring, an aliphatic ring, or a condensed ring of and the aromatic ring and the aliphatic ring, and may be selected from the examples of the heteroaryl group, except for the hetero ring which is not monovalent.

According to an exemplary embodiment of the present specification, $R_1$ to $R_6$ are the same as or different from each other, and are each independently hydrogen; a halogen group; a nitrile group; a sulfonate group; a carboxyl group; a substituted or unsubstituted alkyl group; a substituted or unsubstituted cycloalkyl group; a substituted or unsubstituted aryl group; or a substituted or unsubstituted heterocyclic group.

According to an exemplary embodiment of the present specification, $R_1$ to $R_6$ are the same as or different from each other, and are each independently hydrogen; a halogen group; a nitrile group; —$SO_3X$; —$R_{100}$(C=O)OH; a substituted or unsubstituted straight-chained or branched alkyl group having 1 to 30 carbon atoms; a substituted or unsubstituted monocyclic or polycyclic cycloalkyl group having 3 to 30 carbon atoms; a substituted or unsubstituted aryl group having 6 to 30 carbon atoms; or a substituted or unsubstituted monocyclic or polycyclic heterocyclic group having 2 to 30 carbon atoms, and X is an element of Group 1, and $R_{100}$ is a substituted or unsubstituted straight-chained or branched alkylene group having 1 to 30 carbon atoms; or a substituted or unsubstituted arylene group having 6 to 30 carbon atoms.

According to an exemplary embodiment of the present specification, $R_1$ to $R_6$ are the same as or different from each other, and are each independently hydrogen; a halogen group; a nitrile group; —$SO_3X$; —$R_{100}$(C=O)OH; a substituted or unsubstituted straight-chained or branched alkyl group having 1 to 20 carbon atoms; a substituted or unsubstituted monocyclic or polycyclic cycloalkyl group having 3 to 20 carbon atoms; a substituted or unsubstituted aryl group having 6 to 20 carbon atoms; or a substituted or unsubstituted monocyclic or polycyclic heterocyclic group having 2 to 20 carbon atoms, and X is an element of Group 1, and $R_{103}$ is a substituted or unsubstituted straight-chained or branched alkylene group having 1 to 20 carbon atoms; or a substituted or unsubstituted arylene group having 6 to 20 carbon atoms.

According to an exemplary embodiment of the present specification, $R_1$ to $R_6$ are the same as or different from each other, and are each independently hydrogen; chlorine; a nitrile group; —$SO_3Na$; —$R_{100}$(C=O)OH; a substituted or unsubstituted methyl group; a substituted or unsubstituted isopropyl group; a substituted or unsubstituted isobutyl group; a substituted or unsubstituted tert-butyl group; a substituted or unsubstituted n-hexyl group; a substituted or unsubstituted n-decanyl group; a substituted or unsubstituted cyclopropyl group; a substituted or unsubstituted cyclopentyl group; a substituted or unsubstituted cyclohexyl group; a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted fluorenyl group; a substituted or unsubstituted dibenzofuranyl group; a substituted or unsubstituted dibenzothiophene group; or a substituted or unsubstituted carbazolyl group, and $R_{100}$ is a substituted or unsubstituted n-decanylene group; or a substituted or unsubstituted phenylene group.

According to an exemplary embodiment of the present specification, $R_1$ to $R_6$ are the same as or different from each other, and are each independently hydrogen; chlorine; a nitrile group; —$SO_3Na$; —$R_{100}$(C=O)OH; a methyl group which is unsubstituted or substituted with fluorine; an isopropyl group; an isobutyl group; a tert-butyl group; an n-hexyl group; an n-decanyl group; a cyclopropyl group; a cyclopentyl group; a cyclohexyl group; a phenyl group which is unsubstituted or substituted with one or more selected from the group consisting of fluorine, a nitro group, a methyl group, a phenyl group, a biphenyl group, a terphenyl group, a methoxy group, a carbazolyl group, a dibenzofuranyl group, a tert-butyl group, an isopropyl group, an isobutoxy group, a methyl group substituted with fluorine, an n-hexyloxy group, and an n-hexyloxy group substituted with fluorine; a biphenyl group which is unsubstituted or substituted with one or more selected from the group consisting of fluorine, a methyl group, a tert-butyl group, a phenyl group, and a methoxy group; a terphenyl group which is unsubstituted or substituted with one or more selected from the group consisting of a methyl group, a phenyl group, and a methoxy group; a naphthyl group which is unsubstituted or substituted with one or more selected from the group consisting of a phenyl group, a biphenyl group, a dibenzofuranyl group, a dibenzothiophene group, and a fluorenyl group substituted with a methyl group; an anthracenyl group which is unsubstituted or substituted with a phenyl group; a fluorenyl group which is unsubstituted or substituted with a methyl group or a phenyl group; a dibenzofuranyl group which is unsubstituted or substituted with a tert-butyl group; a dibenzothiophene group; or a carbazolyl group which is unsubstituted or substituted with a phenyl group, or a phenyl group substituted with a nitro group, and $R_{100}$ is an n-decanylene group; or a phenylene group which is unsubstituted or substituted with a methyl group.

According to an exemplary embodiment of the present specification, in Chemical Formula 1, $L_1$ is a direct bond; or a substituted or unsubstituted monocyclic or polycyclic arylene group having 6 to 30 carbon atoms.

According to an exemplary embodiment of the present specification, in Chemical Formula 1, $L_1$ is a direct bond; or a substituted or unsubstituted monocyclic or polycyclic arylene group having 6 to 20 carbon atoms.

According to an exemplary embodiment of the present specification, in Chemical Formula 1, $L_1$ is a direct bond; or a substituted or unsubstituted monocyclic or polycyclic arylene group having 6 to 10 carbon atoms.

According to an exemplary embodiment of the present specification, in Chemical Formula 1, $L_1$ is a direct bond; a substituted or unsubstituted phenylene group; or a substituted or unsubstituted naphthylene group.

According to an exemplary embodiment of the present specification, in Chemical Formula 1, $L_1$ is a direct bond; a phenylene group which is unsubstituted or substituted with a phenyl group or a dibenzofuranyl group; or a naphthylene group.

According to an exemplary embodiment of the present specification, in Chemical Formula 1, $X_1$ is $CR_{12}R_{13}$, $NR_{14}$, O, or S, and $R_{12}$ to $R_{14}$ are the same as or different from each other, and are each independently a substituted or unsubstituted straight-chained or branched alkyl group having 1 to 30 carbon atoms; or a substituted or unsubstituted aryl group having 6 to 30 carbon atoms.

According to an exemplary embodiment of the present specification, $R_{12}$ to $R_{14}$ are the same as or different from each other, and are each independently a substituted or unsubstituted straight-chained or branched alkyl group having 1 to 20 carbon atoms; or a substituted or unsubstituted aryl group having 6 to 20 carbon atoms.

According to an exemplary embodiment of the present specification, $R_{12}$ to $R_{14}$ are the same as or different from each other, and are each independently a substituted or unsubstituted methyl group; a substituted or unsubstituted isobutyl group; a substituted or unsubstituted phenyl group; or a substituted or unsubstituted biphenyl group.

According to an exemplary embodiment of the present specification, $R_{12}$ to $R_{14}$ are the same as or different from each other, and are each independently a methyl group; an isobutyl group; a phenyl group which is unsubstituted or substituted with a methyl group, a nitro group, or a tert-butyl group; or a biphenyl group.

According to an exemplary embodiment of the present specification, in Chemical Formula 1, $Y_1$ is a direct bond or $CR_{15}R_{16}$, and $R_{15}$ and $R_{16}$ are the same as or different from each other, and are each independently a substituted or unsubstituted straight-chained or branched alkyl group having 1 to 30 carbon atoms.

According to an exemplary embodiment of the present specification, $R_{15}$ and $R_{16}$ are the same as or different from each other, and are each independently a substituted or unsubstituted straight-chained or branched alkyl group having 1 to 20 carbon atoms.

According to an exemplary embodiment of the present specification, $R_{15}$ and $R_{16}$ are the same as or different from each other, and are each independently a substituted or unsubstituted methyl group.

According to an exemplary embodiment of the present specification, $R_{15}$ and $R_{16}$ are a methyl group.

According to an exemplary embodiment of the present specification, in Chemical Formula 1, $R_7$ to $R_{11}$ are the same as or different from each other, and are each independently hydrogen; or a substituted or unsubstituted alkyl group.

According to an exemplary embodiment of the present specification, $R_7$ to $R_{11}$ are the same as or different from each other, and are each independently hydrogen; or a substituted or unsubstituted straight-chained or branched alkyl group having 1 to 30 carbon atoms.

According to an exemplary embodiment of the present specification, $R_7$ to $R_{11}$ are hydrogen.

According to an exemplary embodiment of the present specification, in Chemical Formula 1, any adjacent two of $R_7$ to $R_{10}$ are linked to each other to form a substituted or unsubstituted hydrocarbon ring.

According to an exemplary embodiment of the present specification, any adjacent two of $R_7$ to $R_{10}$ are linked to each other to form a substituted or unsubstituted monocyclic or polycyclic hydrocarbon ring having 3 to 30 carbon atoms.

According to an exemplary embodiment of the present specification, any adjacent two of $R_7$ to $R_{10}$ are linked to each other to form a substituted or unsubstituted benzene ring.

According to an exemplary embodiment of the present specification, any adjacent two of $R_7$ to $R_{10}$ are linked to each other to form a benzene ring.

According to an exemplary embodiment of the present specification, in Chemical Formula 2, $L_2$ is a direct bond; or a substituted or unsubstituted monocyclic or polycyclic arylene group having 6 to 30 carbon atoms.

According to an exemplary embodiment of the present specification, in Chemical Formula 2, $L_2$ is a direct bond; or a substituted or unsubstituted monocyclic or polycyclic arylene group having 6 to 20 carbon atoms.

According to an exemplary embodiment of the present specification, in Chemical Formula 2, $L_2$ is a direct bond; or a substituted or unsubstituted monocyclic or polycyclic arylene group having 6 to 10 carbon atoms.

According to an exemplary embodiment of the present specification, in Chemical Formula 2, $L_2$ is a direct bond; a substituted or unsubstituted phenylene group; or a substituted or unsubstituted naphthylene group.

According to an exemplary embodiment of the present specification, in Chemical Formula 2, $L_2$ is a direct bond; a phenylene group which is unsubstituted or substituted with a phenyl group or a dibenzofuranyl group; or a naphthylene group.

According to an exemplary embodiment of the present specification, in Chemical Formula 2, $X_2$ is $CR_{23}R_{24}$, $NR_{25}$, O, or S, and $R_{23}$ to $R_{25}$ are the same as or different from each other, and are each independently a substituted or unsubstituted straight-chained or branched alkyl group having 1 to 30 carbon atoms; or a substituted or unsubstituted aryl group having 6 to 30 carbon atoms.

According to an exemplary embodiment of the present specification, $R_{23}$ to $R_{25}$ are the same as or different from each other, and are each independently a substituted or unsubstituted straight-chained or branched alkyl group having 1 to 20 carbon atoms; or a substituted or unsubstituted aryl group having 6 to 20 carbon atoms.

According to an exemplary embodiment of the present specification, $R_{23}$ to $R_{25}$ are the same as or different from each other, and are each independently a substituted or unsubstituted methyl group; a substituted or unsubstituted isobutyl group; a substituted or unsubstituted phenyl group; or a substituted or unsubstituted biphenyl group.

According to an exemplary embodiment of the present specification, $R_{23}$ to $R_{25}$ are the same as or different from each other, and are each independently a methyl group; an isobutyl group; a phenyl group which is unsubstituted or substituted with a methyl group, a nitro group, or a tert-butyl group; or a biphenyl group.

According to an exemplary embodiment of the present specification, in Chemical Formula 2, $Y_2$ is a direct bond or $CR_{26}R_{27}$, and $R_{26}$ and $R_{27}$ are the same as or different from each other, and are each independently a substituted or unsubstituted straight-chained or branched alkyl group having 1 to 30 carbon atoms.

According to an exemplary embodiment of the present specification, $R_{26}$ and $R_{27}$ are the same as or different from each other, and are each independently a substituted or unsubstituted straight-chained or branched alkyl group having 1 to 20 carbon atoms.

According to an exemplary embodiment of the present specification, $R_{26}$ and $R_{27}$ are the same as or different from each other, and are each independently a substituted or unsubstituted methyl group.

According to an exemplary embodiment of the present specification, $R_{26}$ and $R_{27}$ are a methyl group.

According to an exemplary embodiment of the present specification, in Chemical Formula 2, $R_{18}$ to $R_{22}$ are the same as or different from each other, and are each independently hydrogen; or a substituted or unsubstituted alkyl group.

According to an exemplary embodiment of the present specification, $R_{18}$ to $R_{22}$ are the same as or different from each other, and are each independently hydrogen; or a substituted or unsubstituted straight-chained or branched alkyl group having 1 to 30 carbon atoms.

According to an exemplary embodiment of the present specification, $R_{18}$ to $R_{22}$ are hydrogen.

According to an exemplary embodiment of the present specification, the compound represented by Chemical Formula 1 is any one selected from the following Compounds 1-1 to 1-111.

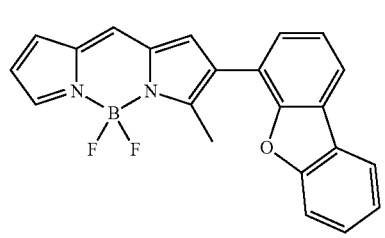

Compound 1-1

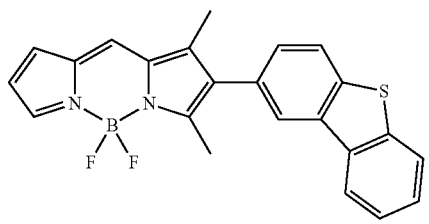

Compound 1-2

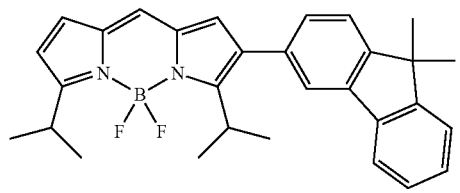

Compound 1-3

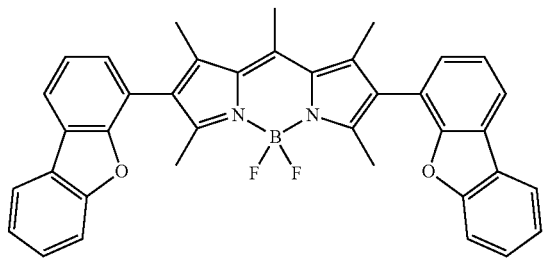

Compound 1-4

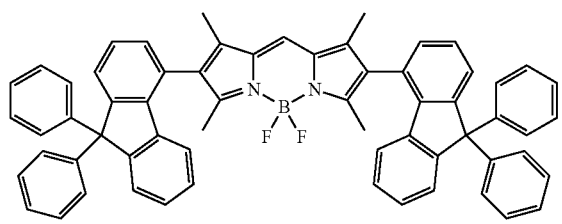

Compound 1-5

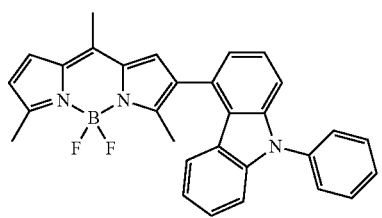

Compound 1-6

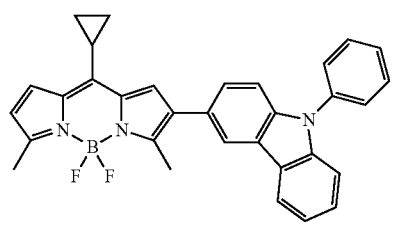

Compound 1-7

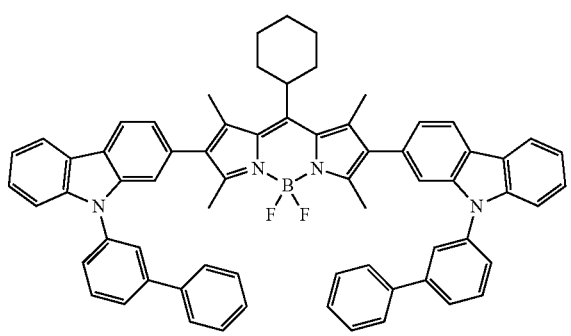

Compound 1-8

-continued
Compound 1-9
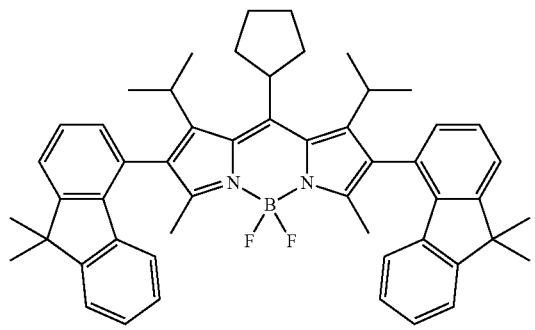
Compound 1-10
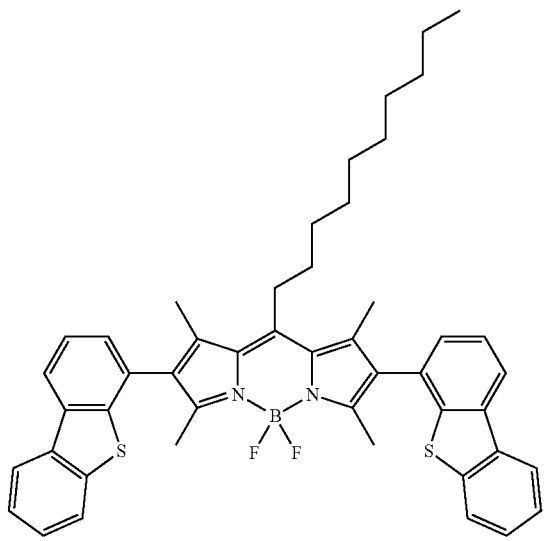
Compound 1-11
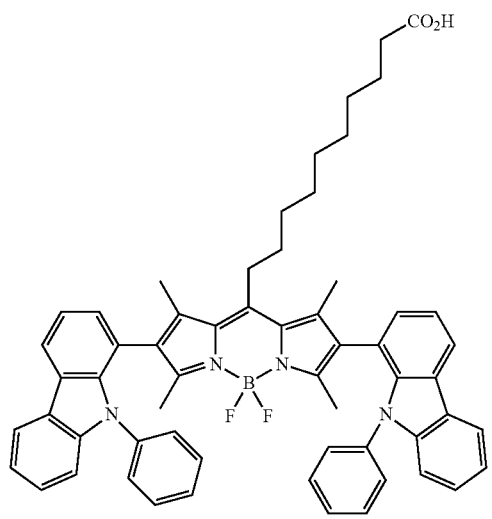
Compound 1-12
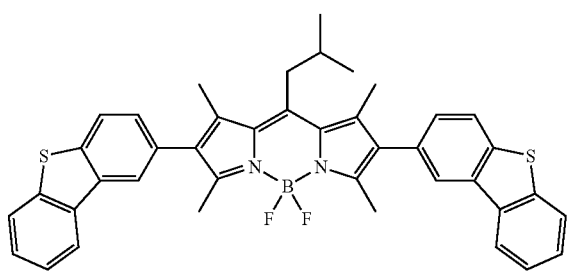
Compound 1-13
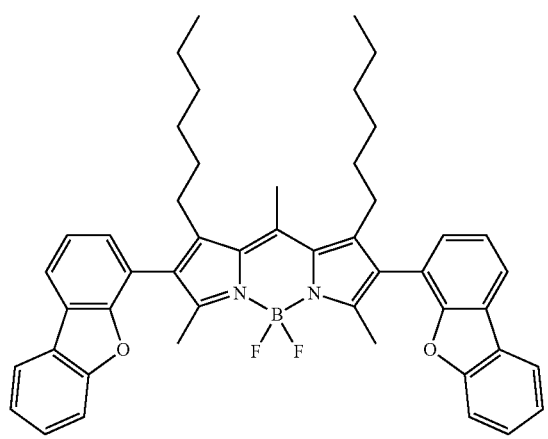
Compound 1-14
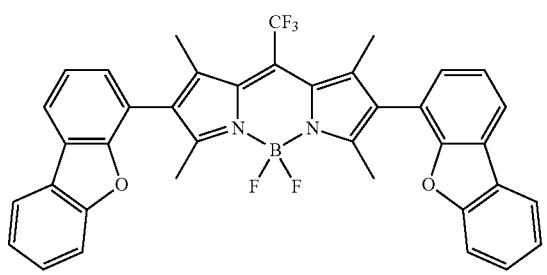

Compound 1-15
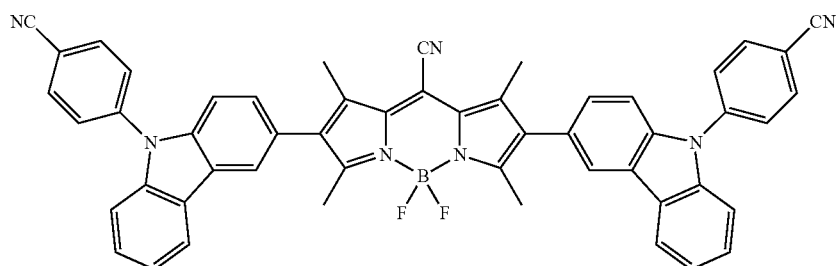
Compound 1-16
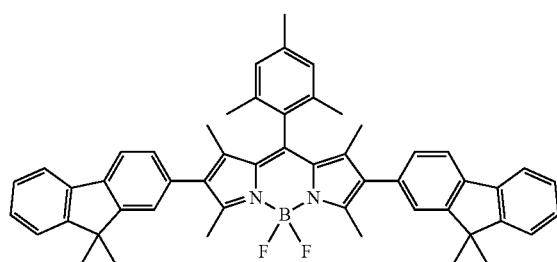
Compound 1-17
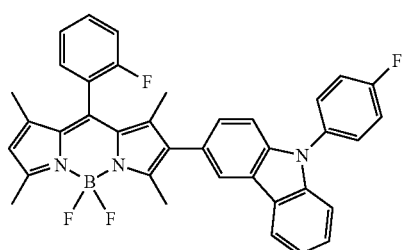
Compound 1-18
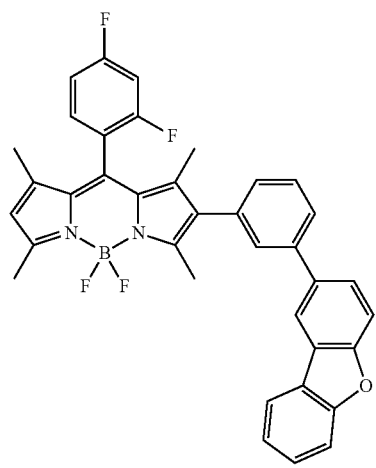
Compound 1-19
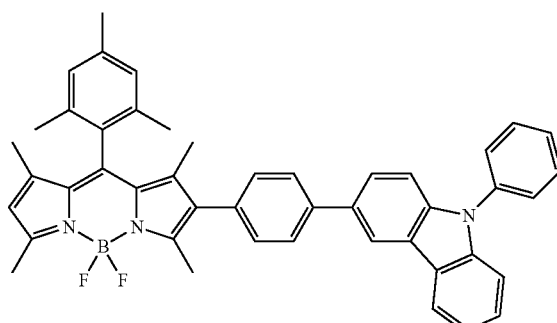
Compound 1-20
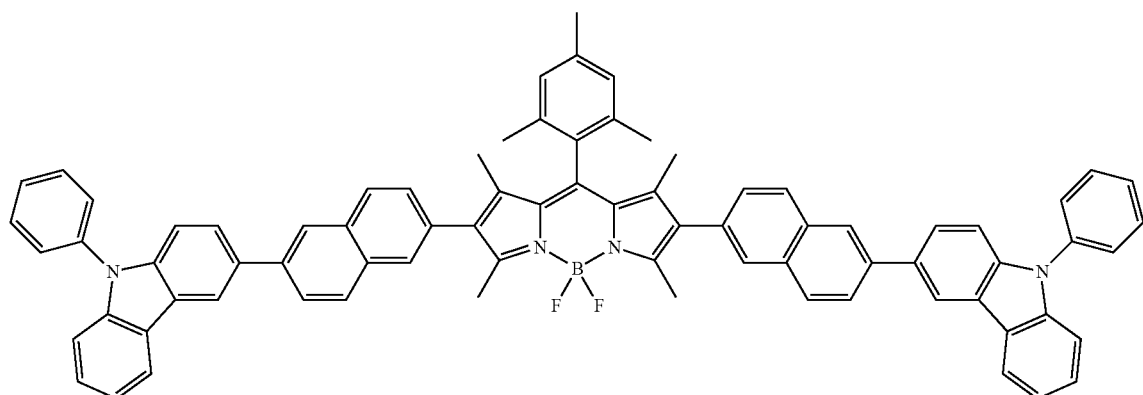

-continued
Compound 1-21
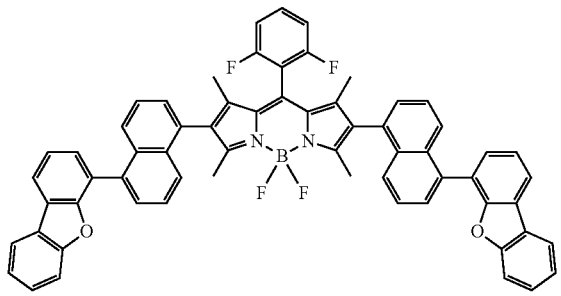
Compound 1-22
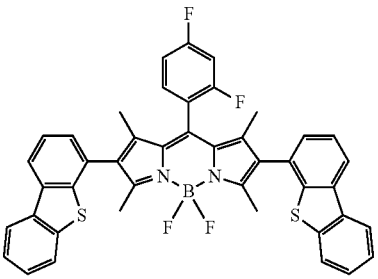
Compound 1-23
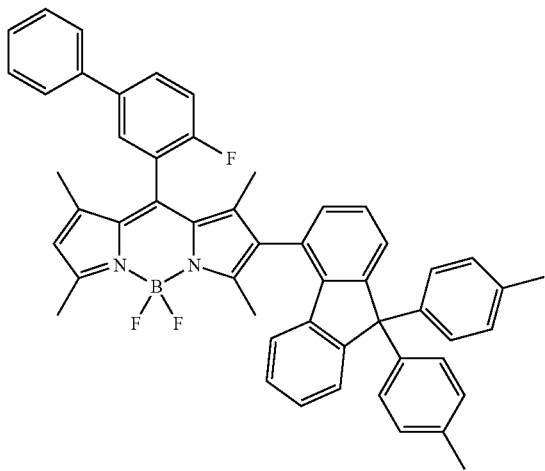
Compound 1-24
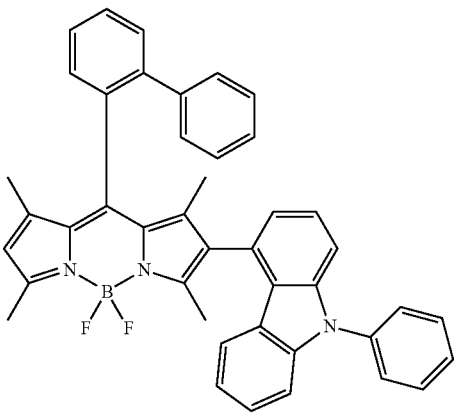
Compound 1-25
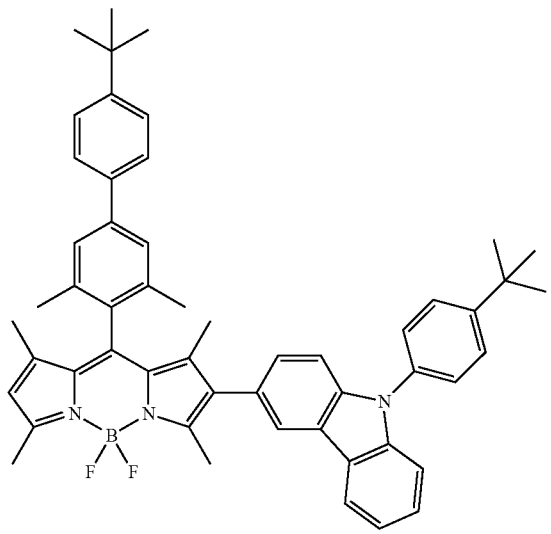
Compound 1-26
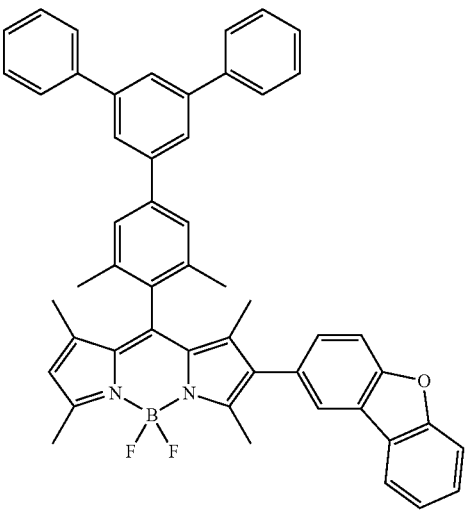

-continued
Compound 1-27
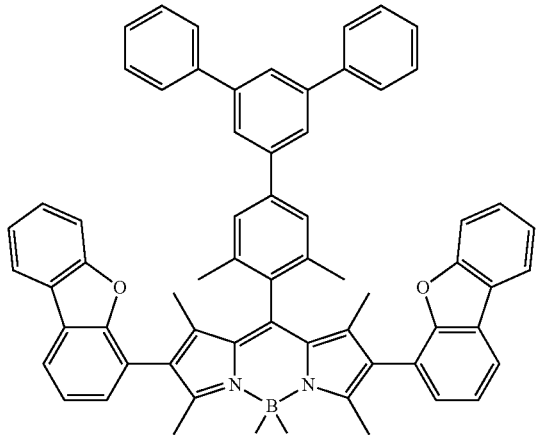
Compound 1-28
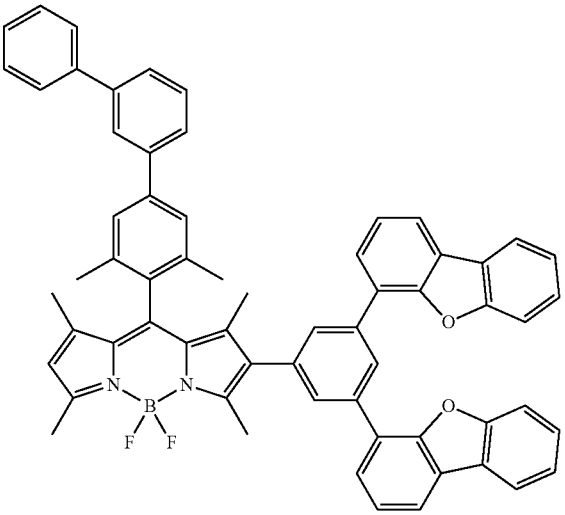
Compound 1-29
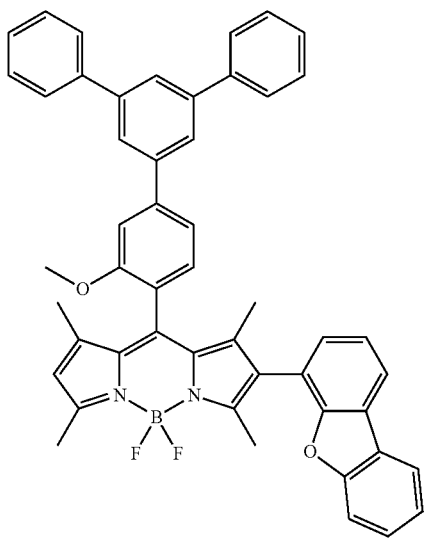
Compound 1-30
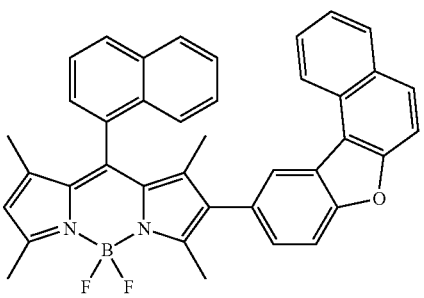
Compound 1-31
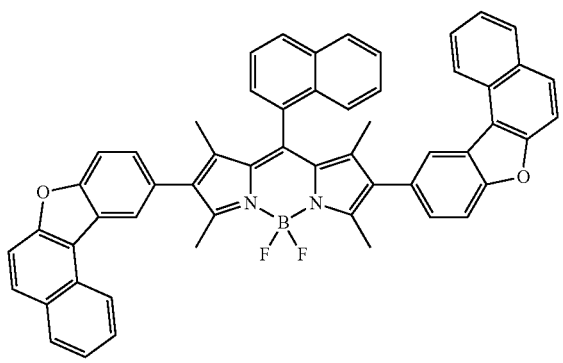
Compound 1-32
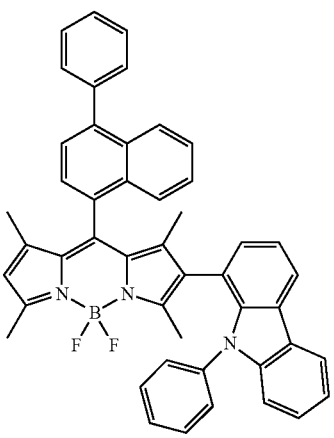

-continued
Compound 1-33
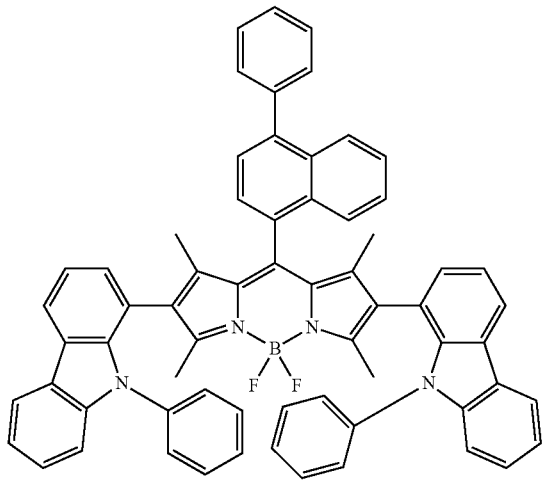
Compound 1-34
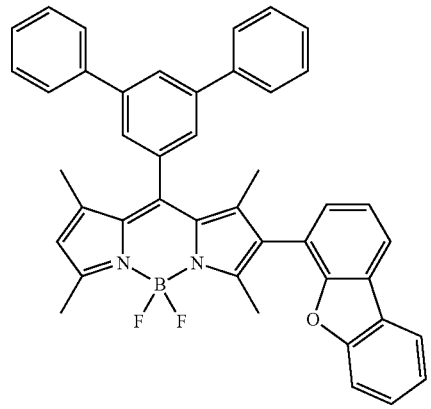
Compound 1-35
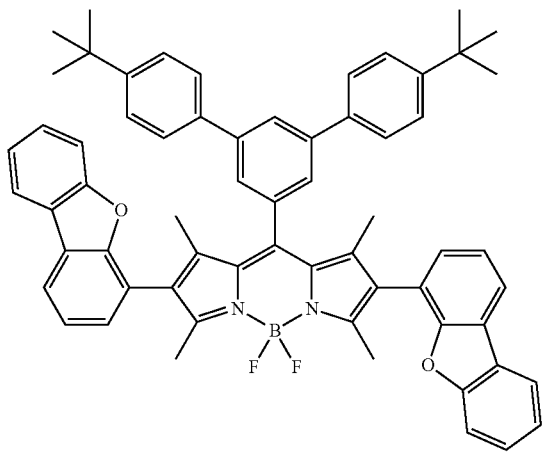
Compound 1-36
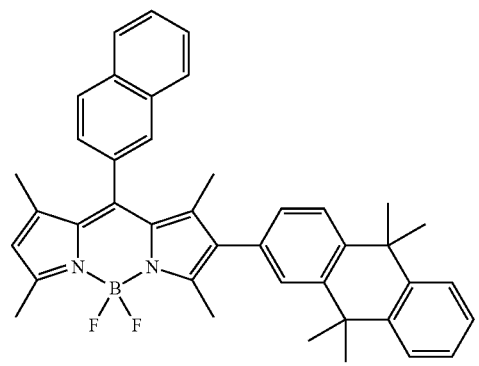
Compound 1-37
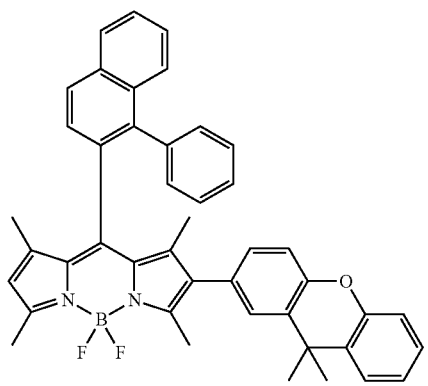
Compound 1-38
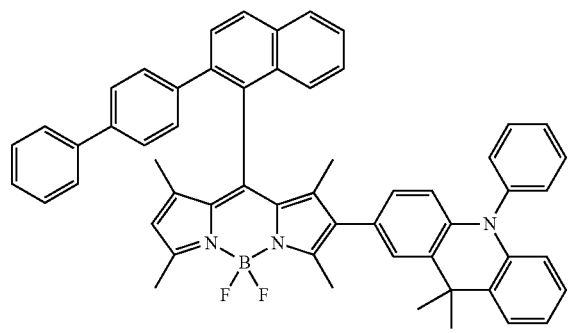

-continued
Compound 1-39
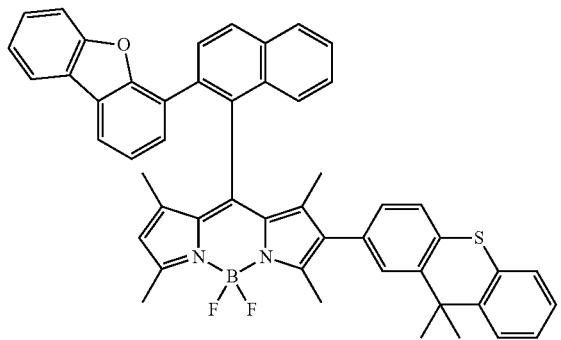
Compound 1-40
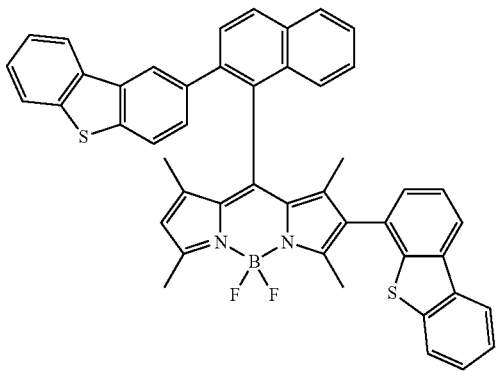
Compound 1-41
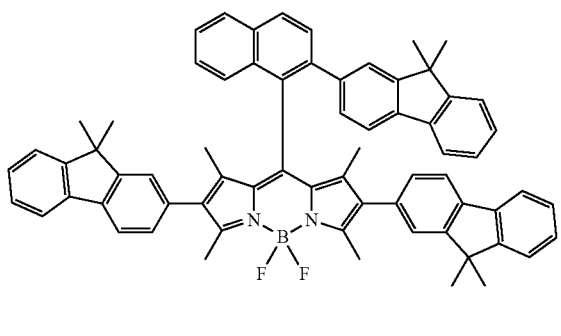
Compound 1-42
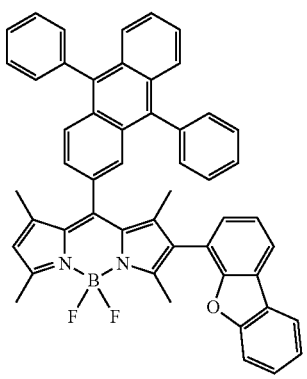
Compound 1-43
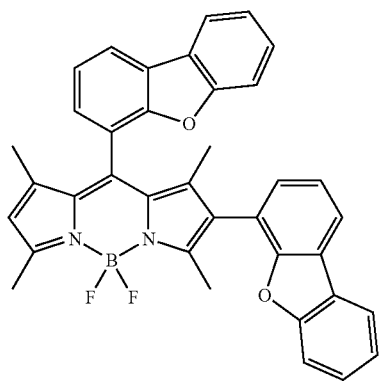
Compound 1-44
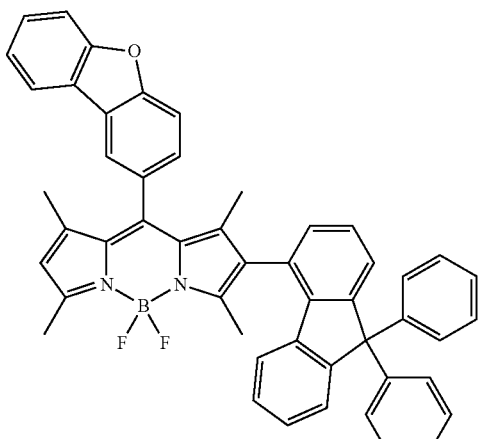
Compound 1-45
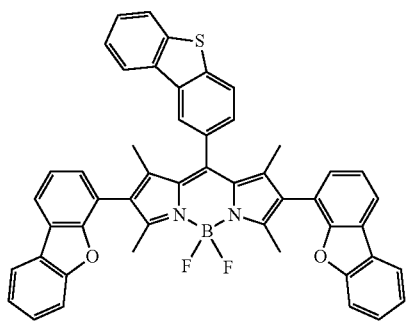
Compound 1-46
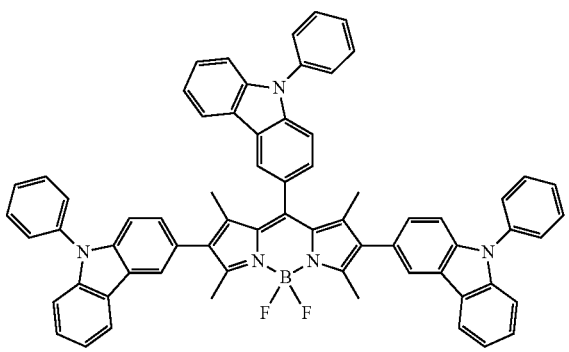

-continued
Compound 1-47
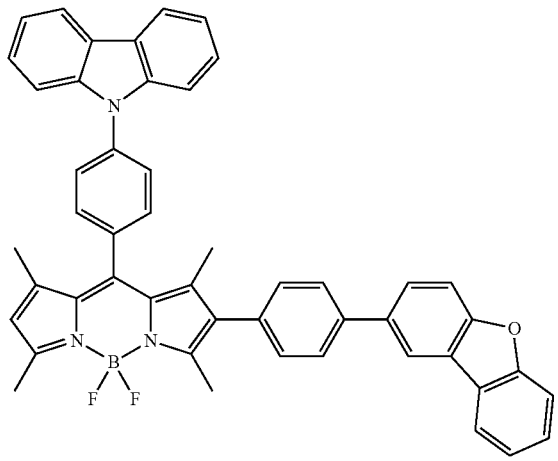
Compound 1-48
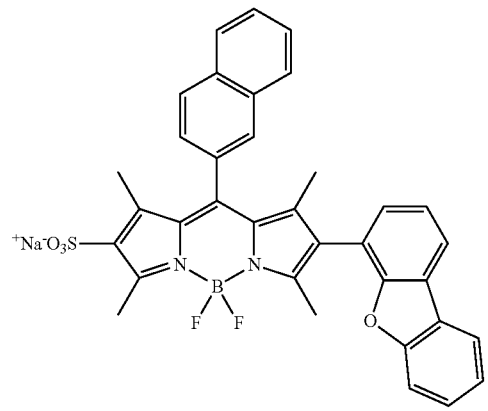
Compound 1-49
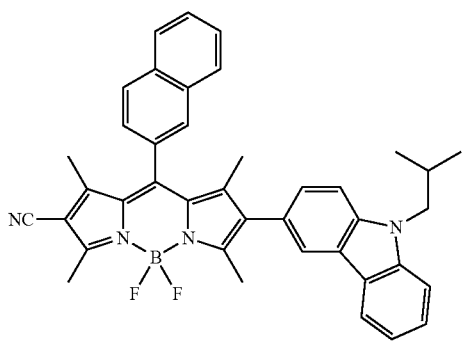
Compound 1-50
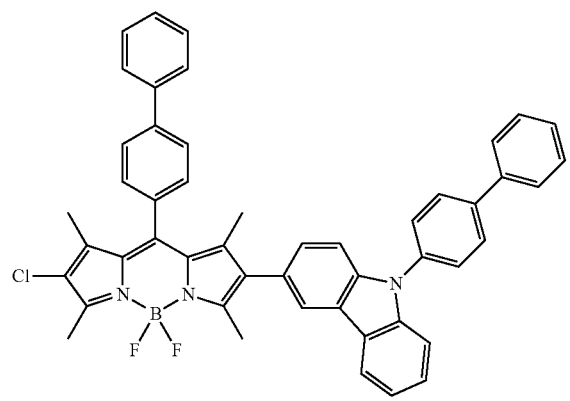
Compound 1-51
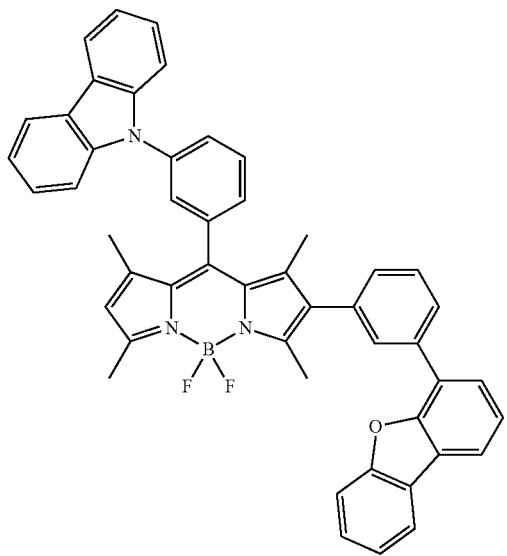
Compound 1-52
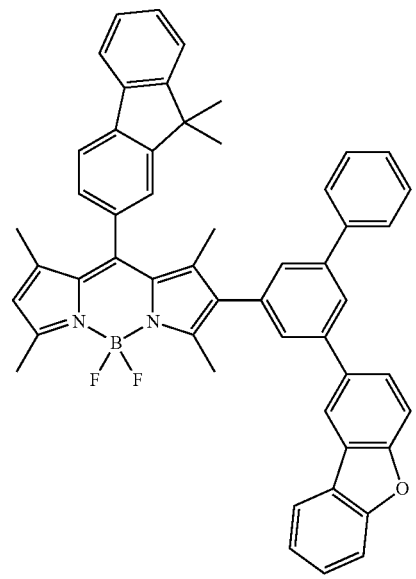

-continued
Compound 1-53
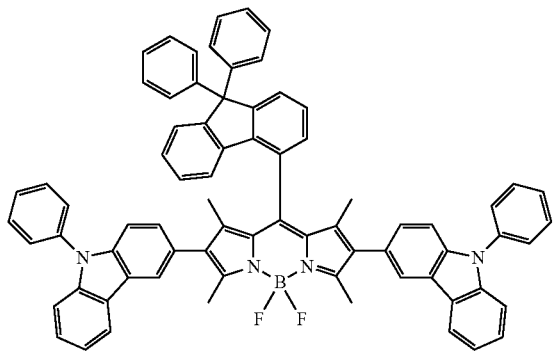
Compound 1-54
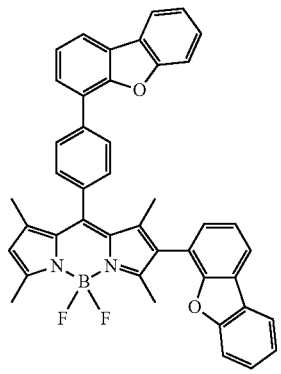
Compound 1-55
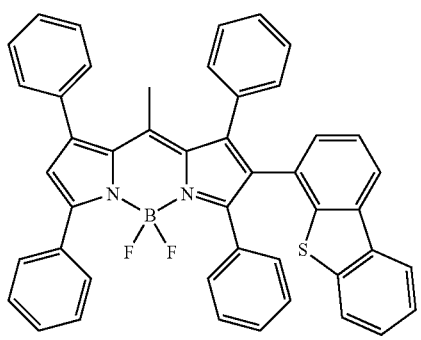
Compound 1-56
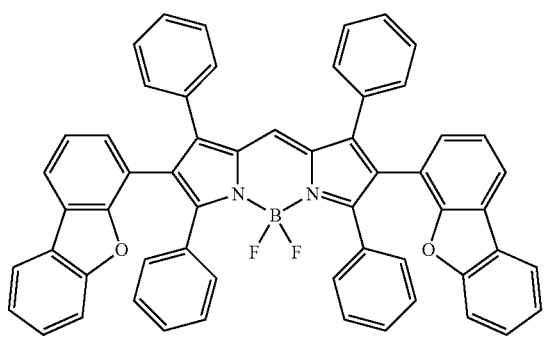
Compound 1-57
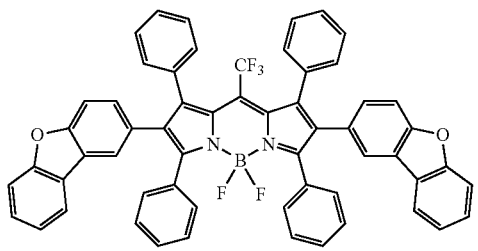
Compound 1-58
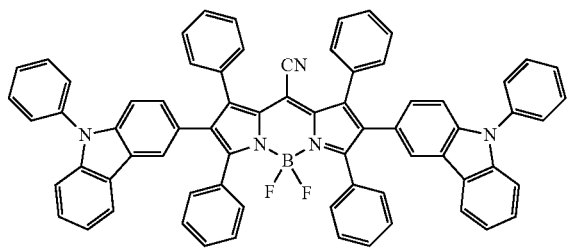
Compound 1-59
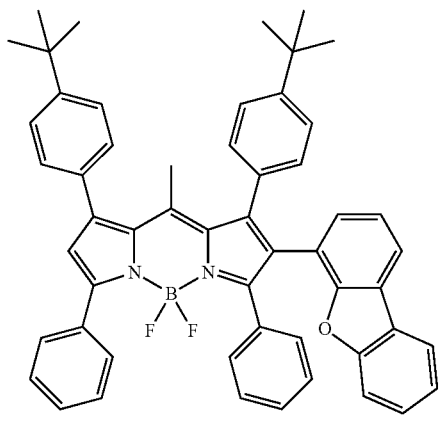
Compound 1-60
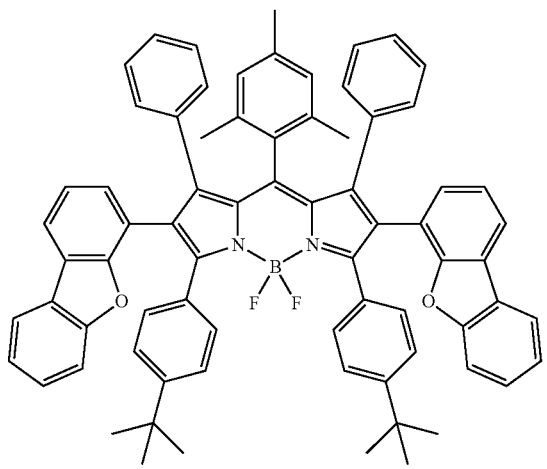

-continued
Compound 1-61
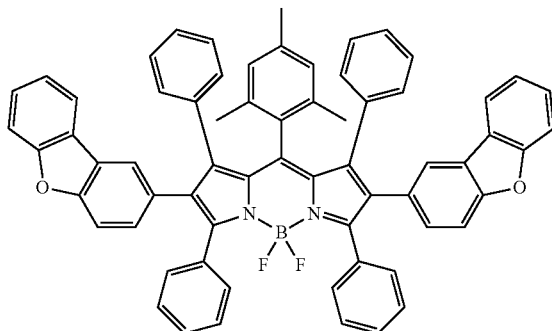
Compound 1-62
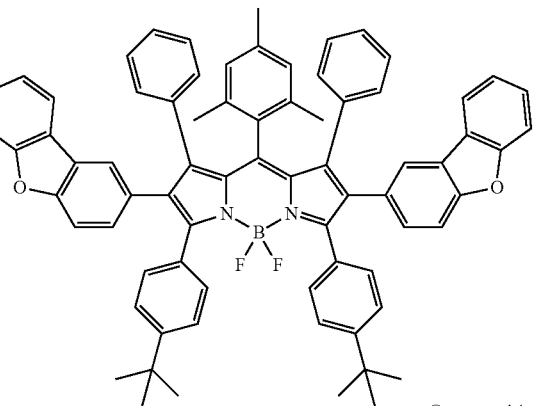
Compound 1-63
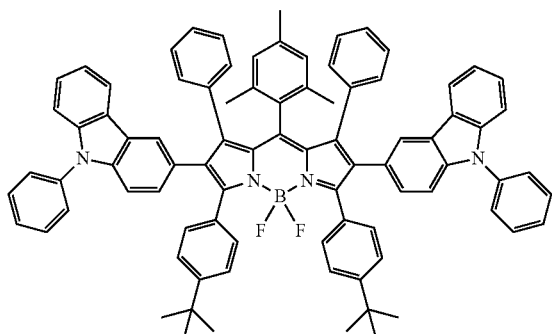
Compound 1-64
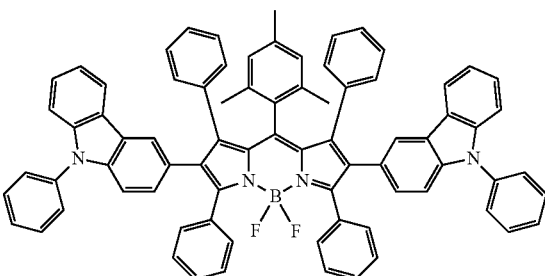
Compound 1-65
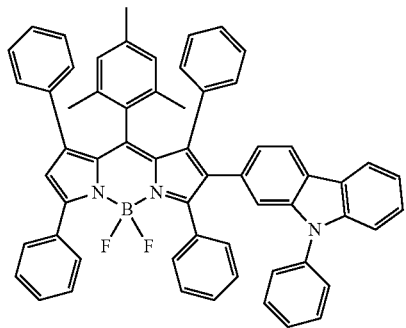
Compound 1-66
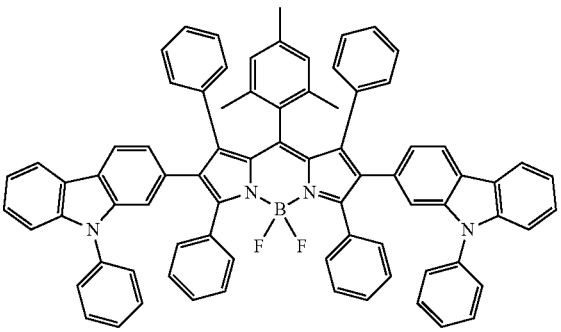
Compound 1-67
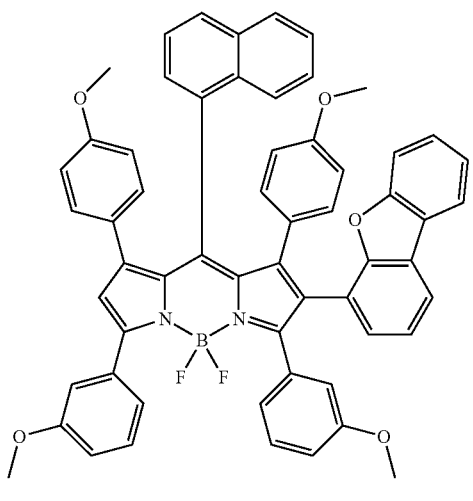
Compound 1-68
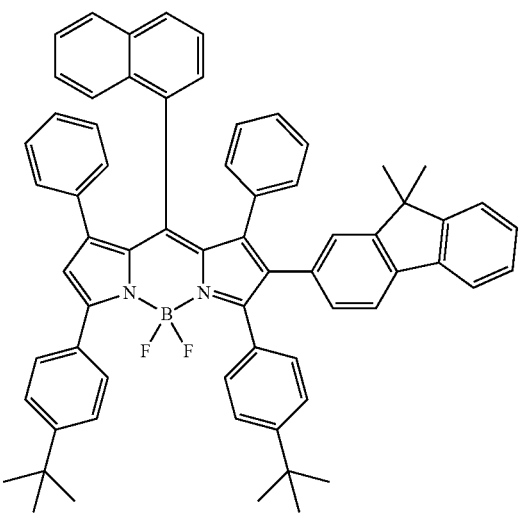

-continued
Compound 1-69
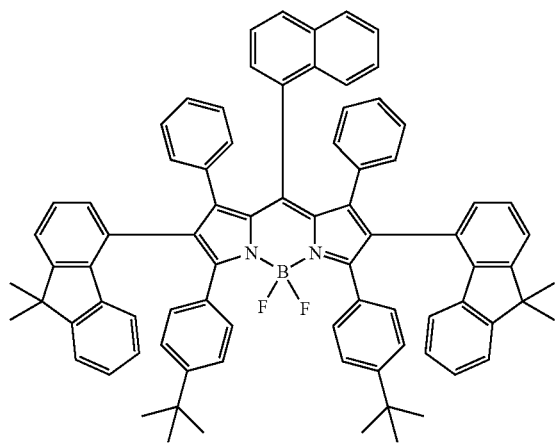
Compound 1-70
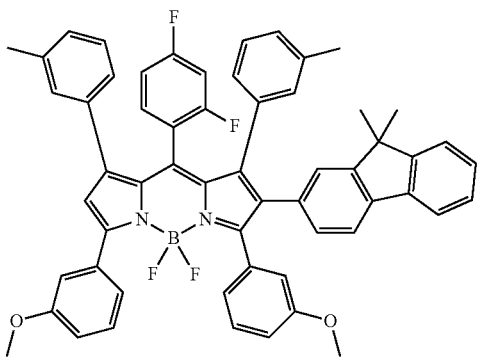
Compound 1-71
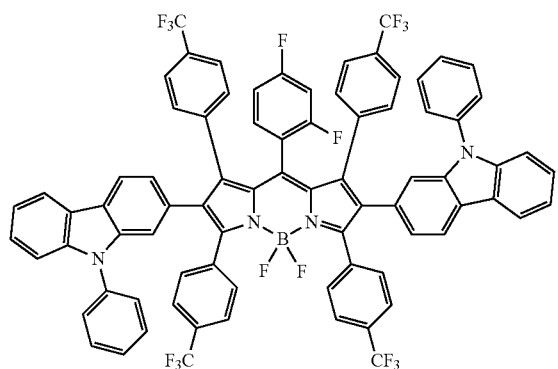
Compound 1-72
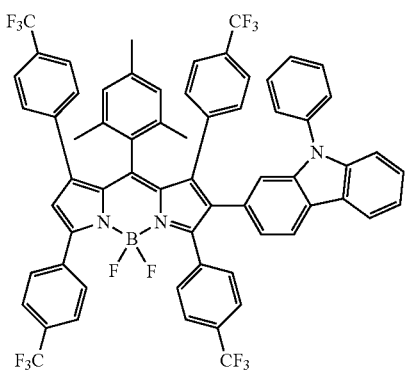
Compound 1-73
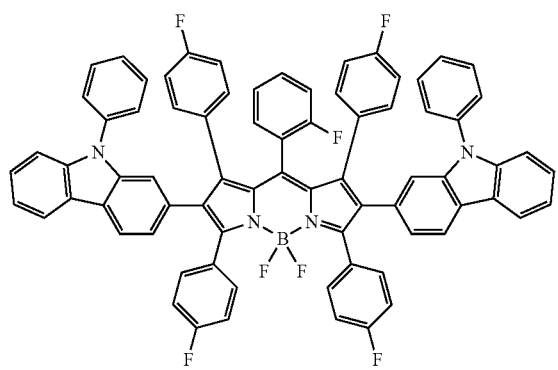
Compound 1-74
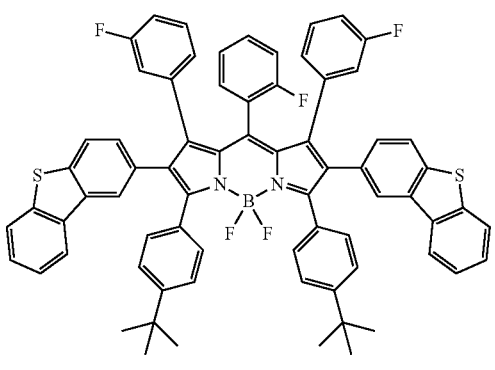
Compound 1-75
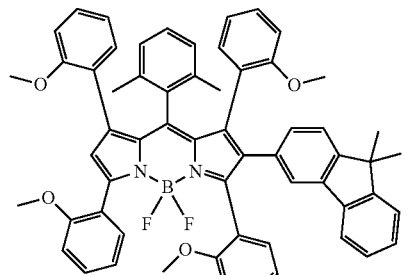
Compound 1-76
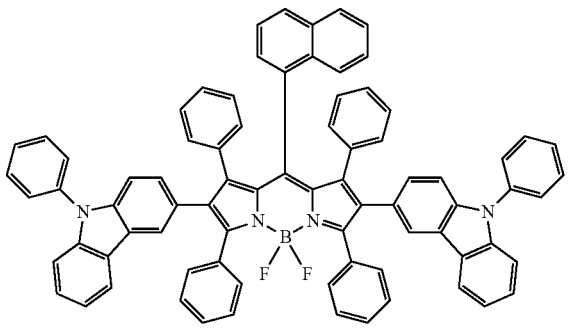

-continued
Compound 1-77
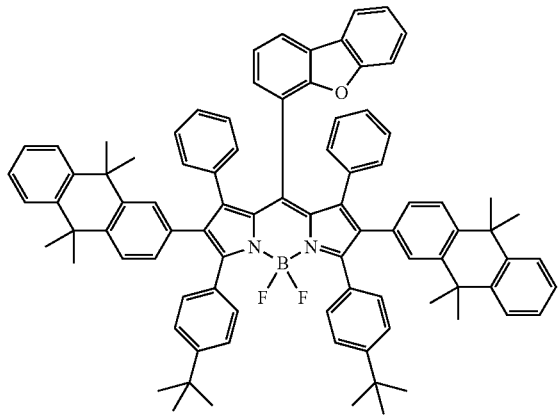
Compound 1-78
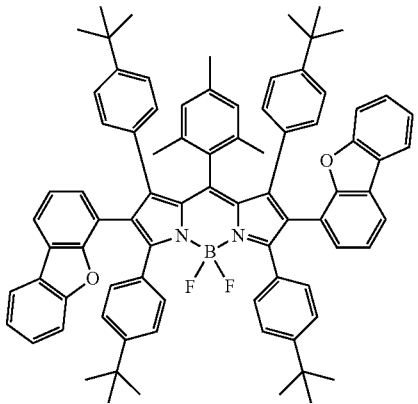
Compound 1-79
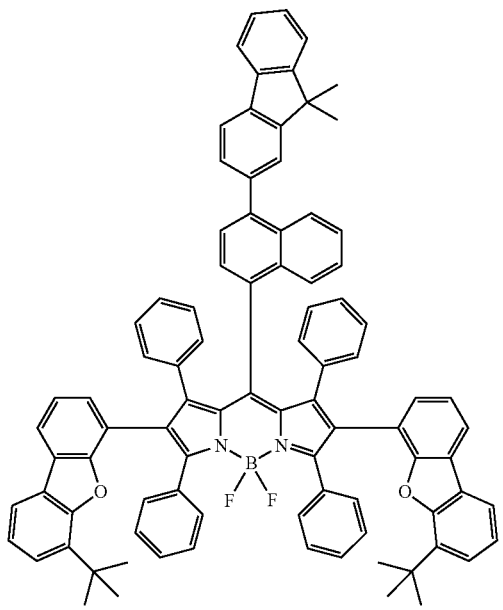
Compound 1-80
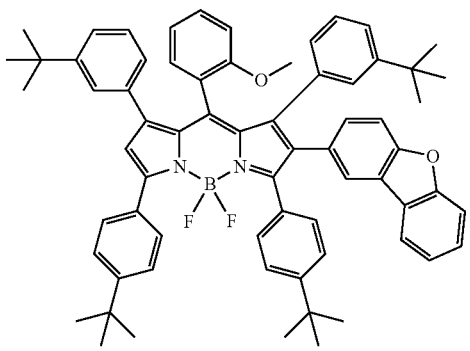
Compound 1-81
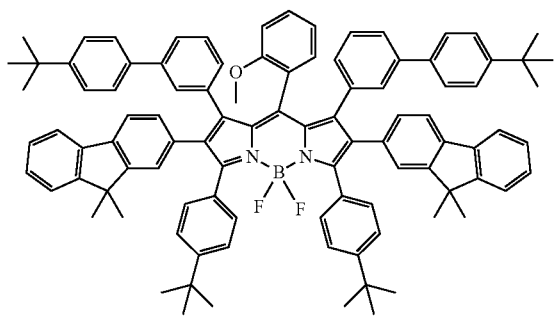
Compound 1-82
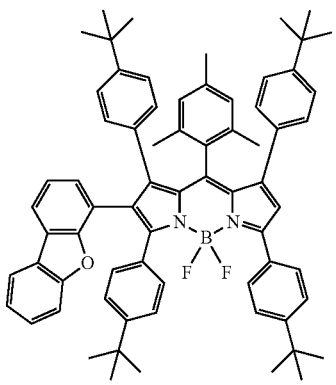

-continued
Compound 1-83
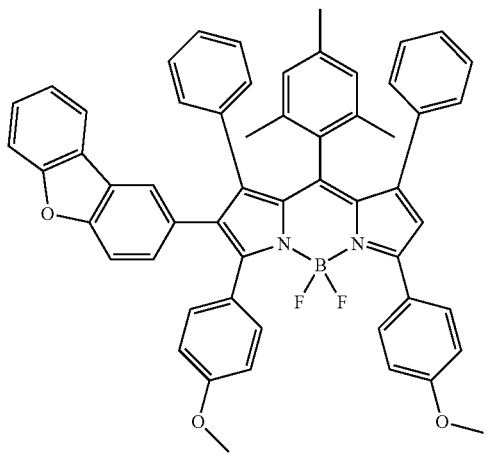
Compound 1-84
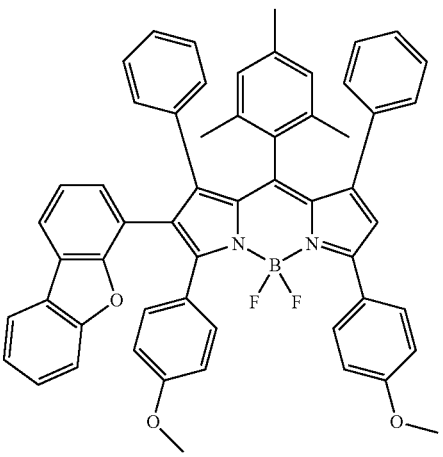
Compound 1-85
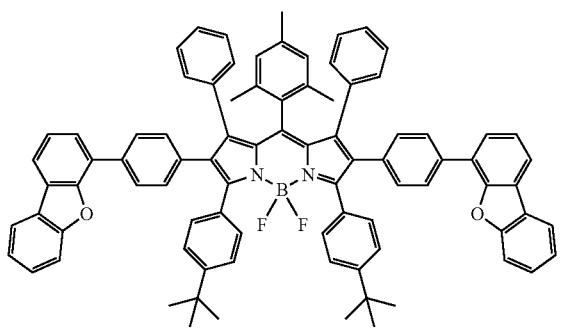
Compound 1-86
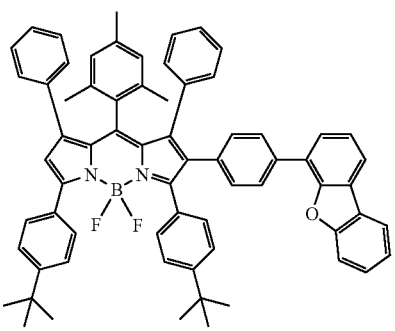
Compound 1-87
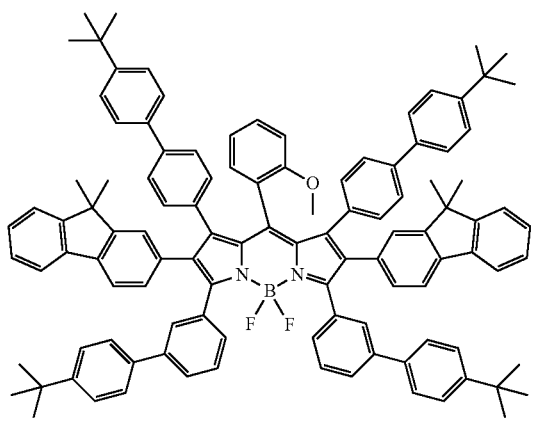
Compound 1-88
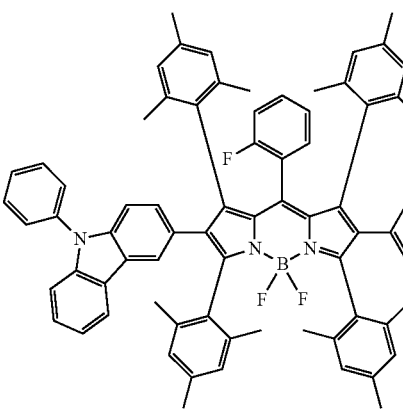
Compound 1-89
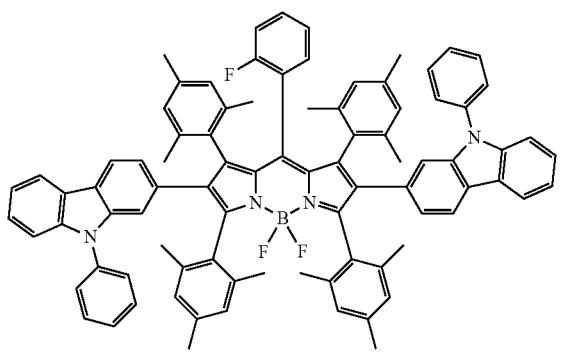
Compound 1-90
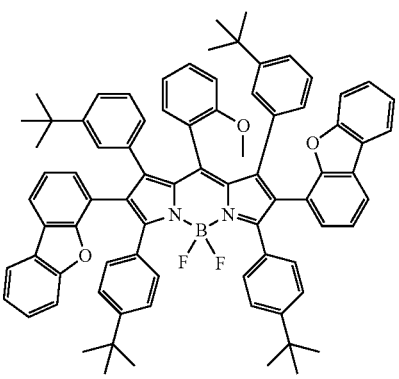

-continued
Compound 1-91
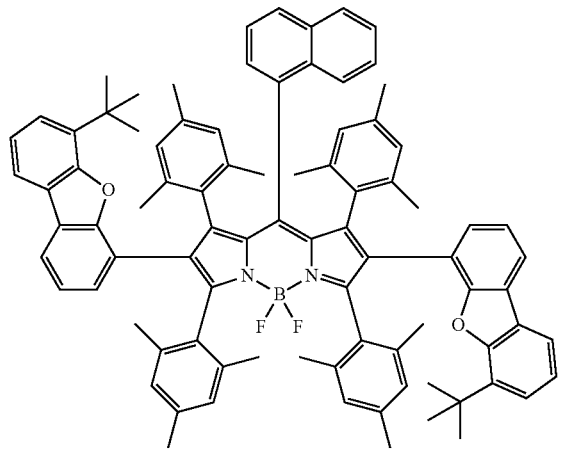
Compound 1-92
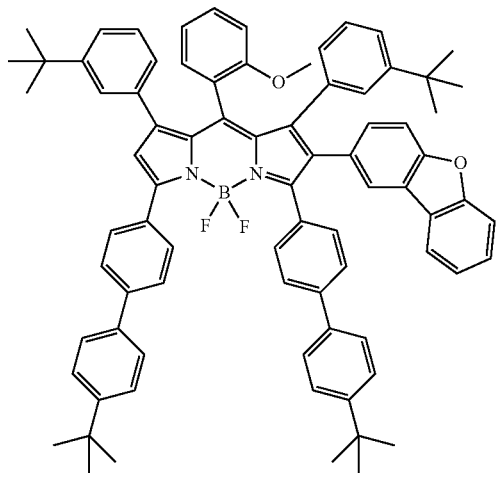
Compound 1-93
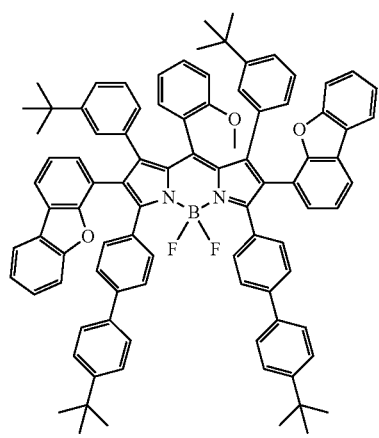
Compound 1-94
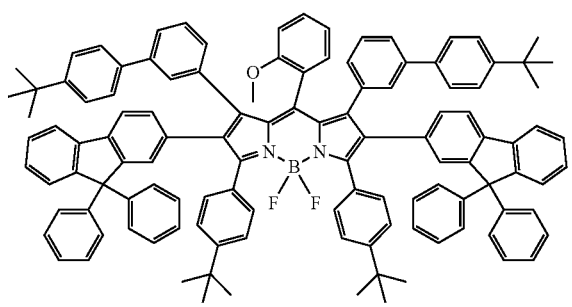
Compound 1-95
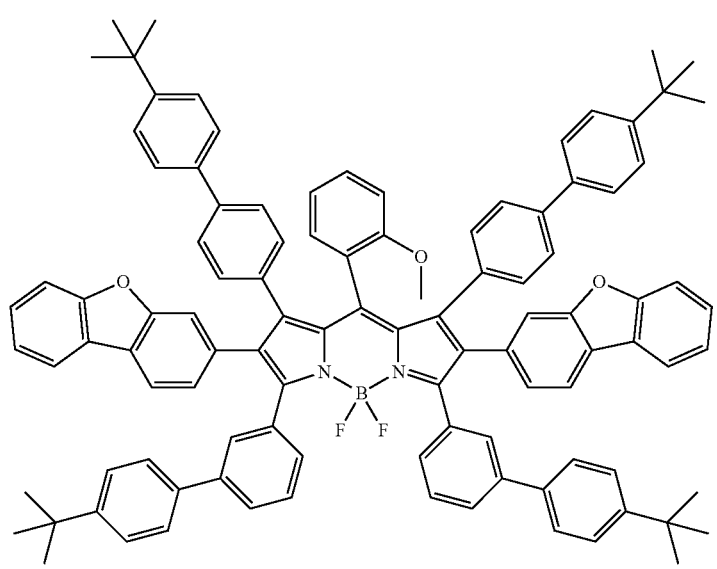

Compound 1-96
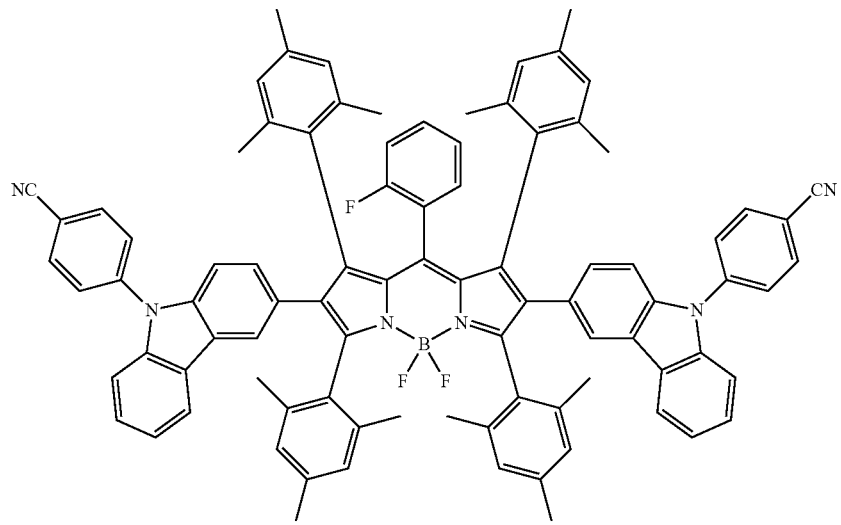
Compound 1-97
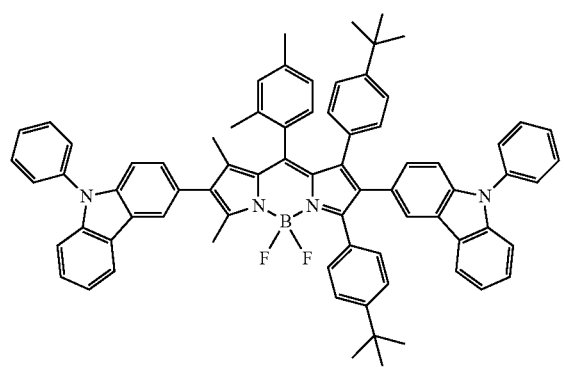
Compound 1-98
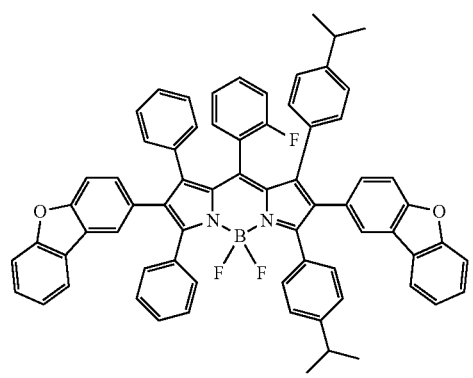
Compound 1-99
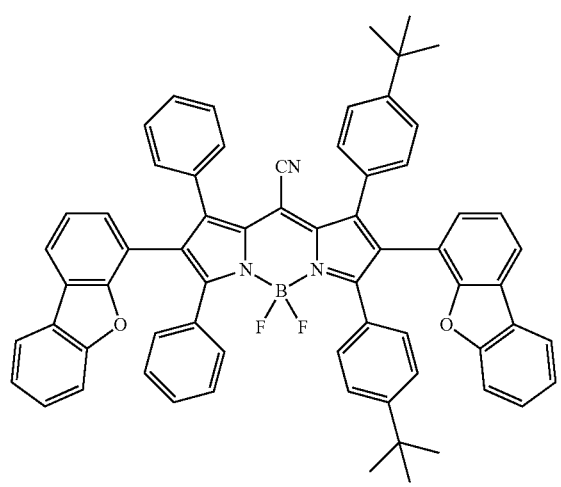
Compound 1-100
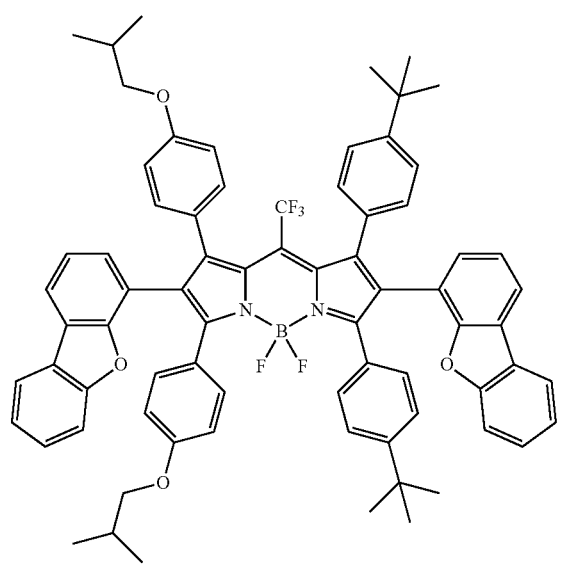

-continued
Compound 1-101
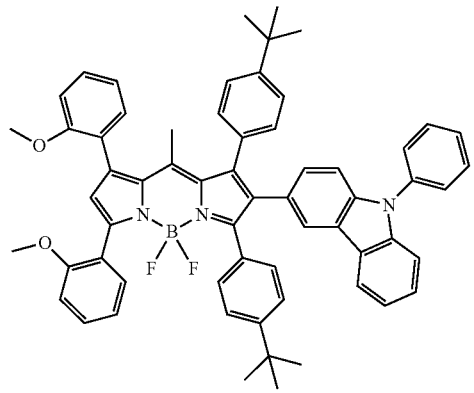
Compound 1-102
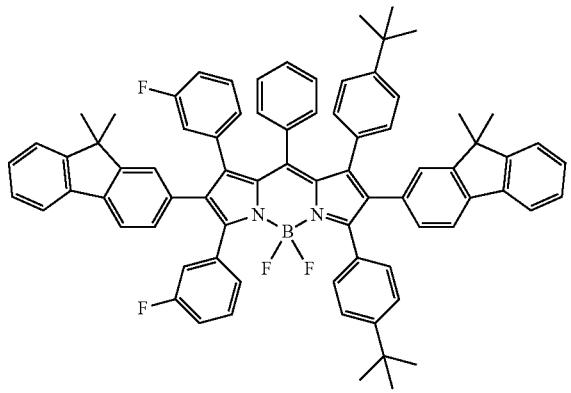
Compound 1-103
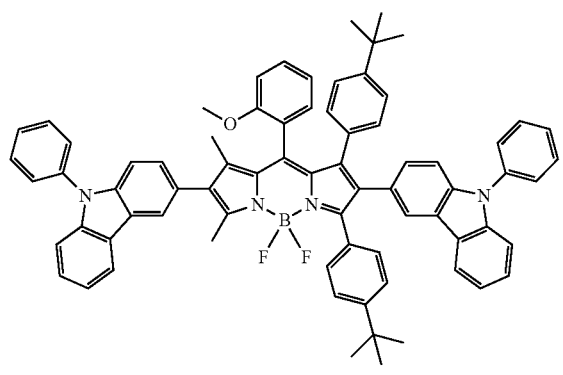
Compound 1-104
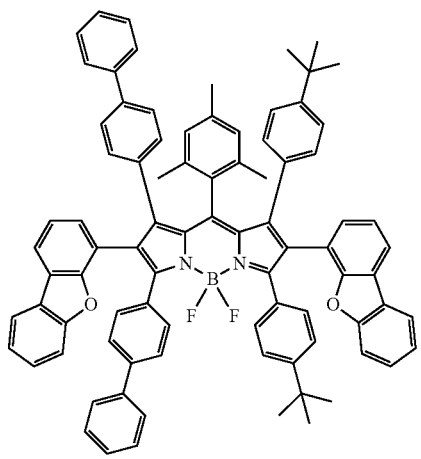
Compound 1-105
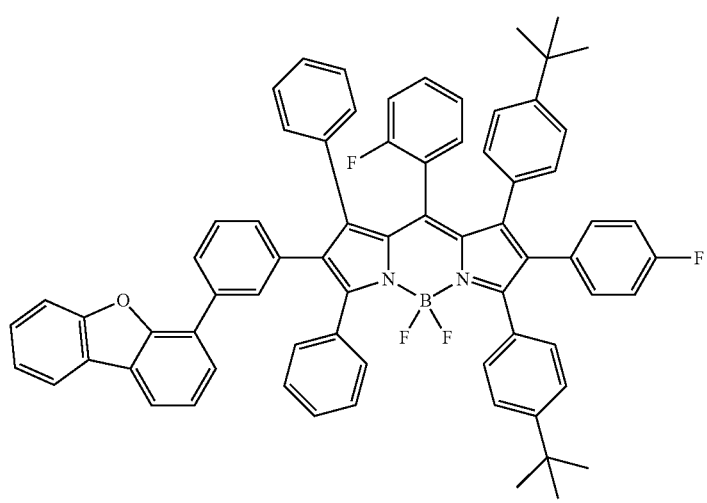

Compound 1-106
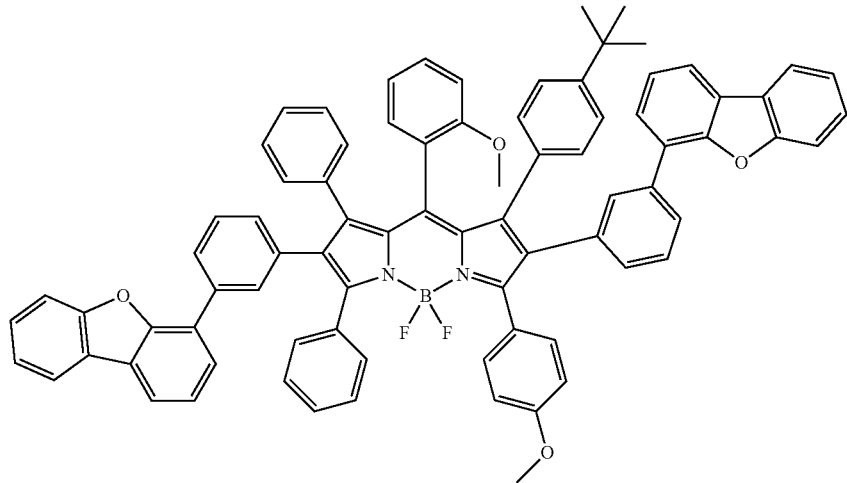
Compound 1-107
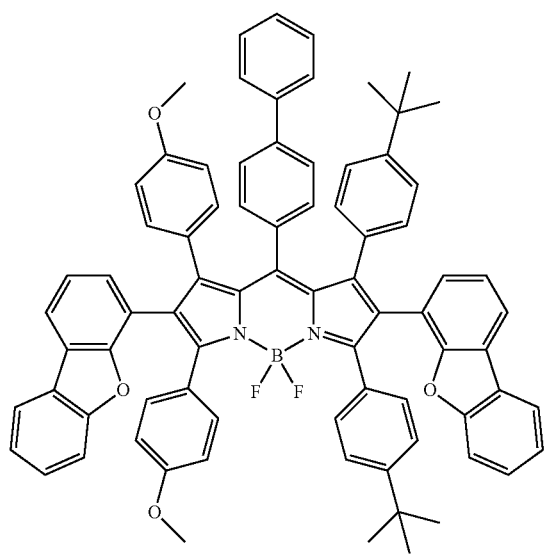
Compound 1-108
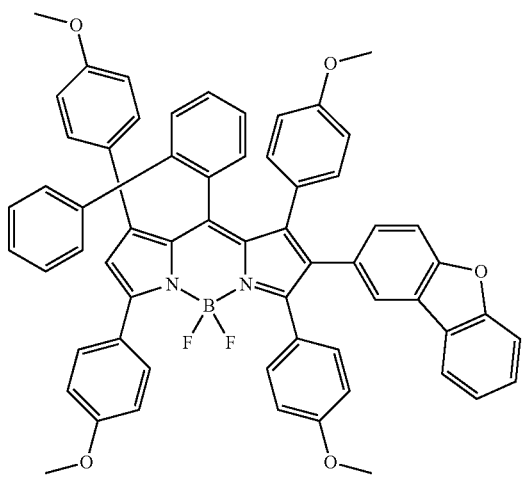
Compound 1-109
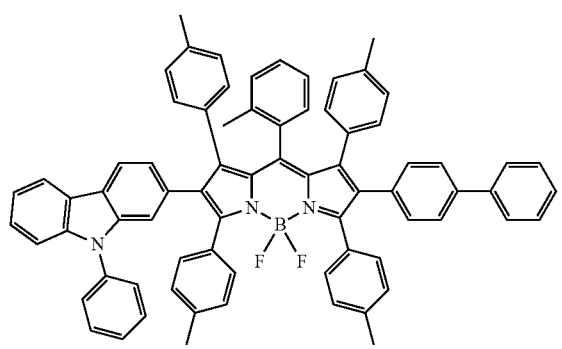
Compound 1-110
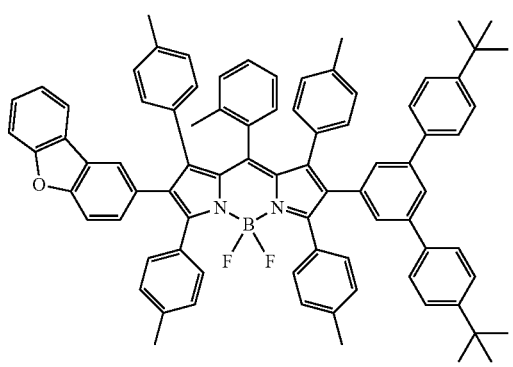

Compound 1-111

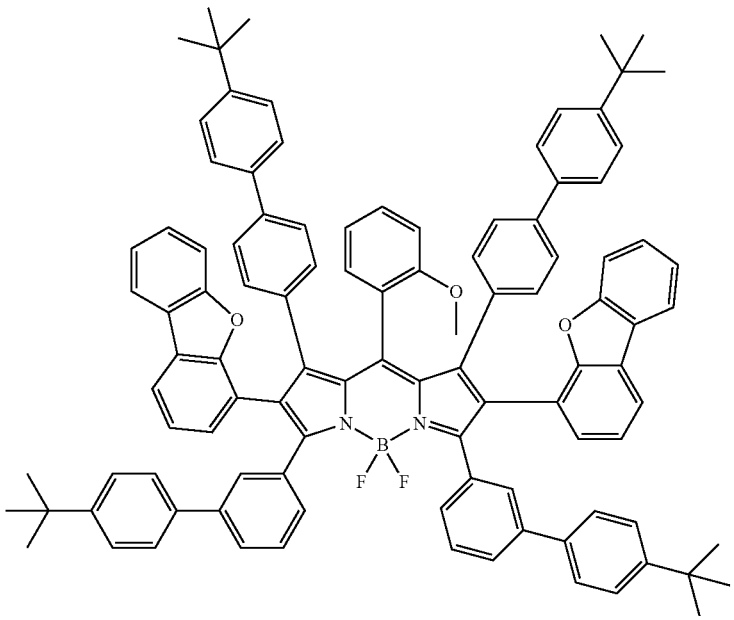

According to another exemplary embodiment of the present specification, provided is a color conversion film comprising: a resin matrix; and the compound represented by Chemical Formula 1, which is dispersed in the resin matrix.

The content of the compound represented by Chemical Formula 1 in the color conversion film may be within a range of 0.001 to 10 wt %.

The color conversion film may also comprise one of the compounds represented by Chemical Formula 1, and may comprise two or more. For example, the color conversion film may comprise one compound which emits green light among the compounds represented by Chemical Formula 1. As another example, the color conversion film may comprise one compound which emits red light among the compounds represented by Chemical Formula 1. As still another example, the color conversion film may comprise one compound which emits green light and one compound which emits red light among the compounds represented by Chemical Formula 1.

The color conversion film may further include an additional fluorescent material in addition to the compound represented by Chemical Formula 1. When a light source which emits blue light is used, it is preferred that the color conversion film comprises both a fluorescent material which emits green light and a fluorescent material which emits red light. Further, when a light source which emits blue light and green light is used, the color conversion film may comprise only a fluorescent material which emits red light. However, the color conversion film is not limited thereto, and even when a light source which emits blue light is used, the color conversion film may comprise only a compound which emits red light in the case where a separate film comprising a fluorescent material which emits green light is stacked. Conversely, even when a light source which emits blue light is used, the color conversion film may comprise only a compound which emits green light in the case where a separate film comprising a fluorescent material which emits red light is stacked.

The color conversion film may further comprise an additional layer comprising: a resin matrix; and a compound which is dispersed in the resin matrix and emits light having a wavelength different from that of the compound represented by Chemical Formula 1. The compound which emits light having a wavelength different from that of the compound represented by Chemical Formula 1 may also be the compound expressed as Chemical Formula 1, and may also be another publicly-known fluorescent material.

It is preferred that a material for the resin matrix is a thermoplastic polymer or a thermosetting polymer. Specifically, as the material for the resin matrix, it is possible to use a poly(meth)acrylic material such as polymethylmethacrylate (PMMA), a polycarbonate (PC)-based material, a polystyrene (PS)-based material, a polyarylene (PAR)-based material, a polyurethane (TPU)-based material, a styrene-acrylonitrile (SAN)-based material, a polyvinylidenefluoride (PVDF)-based material, a modified-polyvinylidenefluoride (modified-PVDF)-based material, and the like.

According to an exemplary embodiment of the present specification, the color conversion film according to the above-described exemplary embodiments additionally comprises a light-diffusing particle. By dispersing a light-diffusing particle in the color conversion film instead of a light-diffusing film used in the related art in order to improve brightness, an attaching process may be omitted, and a higher brightness may be exhibited as compared to the case where a separate light-diffusing film is used.

As the light-diffusing particle, a resin matrix and a particle having a high refractive index may be used, and it is possible to use, for example, $TiO_2$, silica, borosilicate, alumina, sapphire, air or another gas, air- or gas-filled hollow beads or particles (for example, air/gas-filled glass or polymer); polymer particles including polystyrene, polycarbonate, polymethylmethacrylate, acryl, methyl methacrylate, styrene, a melamine resin, a formaldehyde resin, or a melamine and formaldehyde resin, or any suitable combination thereof.

The particle diameter of the light-diffusing particle may be within a range of 0.1 μm to 5 μm, for example, within a range of 0.3 μm to 1 μm. The content of the light-diffusing particle may be determined, if necessary, and may be, for example, within a range of about 1 to 30 parts by weight based on 100 parts by weight of the resin matrix.

The color conversion film according to the above-described exemplary embodiments may have a thickness of 2 μm to 200 μm. In particular, the color conversion film may exhibit high brightness even in a small thickness of 2 μm to 20 μm. This is because the content of the fluorescent material molecule included in a unit volume is higher than that of a quantum dot.

In the color conversion film according to the above-described exemplary embodiments, a base material may be provided on a surface of the color conversion film. The base material may serve as a support when the color conversion film is produced. The kind of base material is not particularly limited, and the material or thickness of the base material is not limited as long as the base material is transparent and may serve as the support. Here, transparency means that the transmittance of visible light is 70% or more. For example, as the base material, a PET film may be used.

The above-described color conversion film may be produced by coating a resin solution, in which the above-described compound represented by Chemical Formula 1 is dissolved, on a base material and drying the resin solution, or extruding the above-described compound represented by Chemical Formula 1 together with the resin to produce a film.

Since the above-described compound represented by Chemical Formula 1 is dissolved in the resin solution, the compound represented by Chemical Formula 1 is uniformly distributed in the solution. This is different from a process of producing a quantum dot film, which requires a separate dispersing process.

For the resin solution in which the compound represented by Chemical Formula 1 is dissolved, the production method thereof is not particularly limited as long as the above-described compound represented by Chemical Formula 1 is present in a state where the resin is dissolved in the solution.

According to an example, the resin solution in which the compound represented by Chemical Formula 1 is dissolved may be produced by a method including: dissolving the compound represented by Chemical Formula 1 in a solvent to prepare a first solution, dissolving a resin in a solvent to prepare a second solution, and mixing the first solution with the second solution. When the first solution and the second solution are mixed, it is preferred to uniformly mix the solutions. However, the method is not limited thereto, and it is possible to use a method including: simultaneously adding a compound represented by Chemical Formula 1 and a resin to a solvent to dissolve the compound and the resin, a method including: dissolving the compound represented by Chemical Formula 1 in a solvent, and subsequently adding the resin thereto to dissolve the compound and the resin, a method including: dissolving the resin in a solvent, and subsequently adding the compound represented by Chemical Formula 1 thereto to dissolve the compound, and the like.

As the resin included in the solution, it is possible to use the above-described resin matrix material, a monomer which is curable by the resin matrix, or a mixture thereof. Examples of the monomer which is curable by the resin matrix include a (meth)acrylic monomer, and the monomer may be formed as a resin matrix material by UV curing. When a curable monomer is used as described above, an initiator required for curing may be further added, if necessary.

The solvent is not particularly limited, and is not particularly limited as long as the solvent may be removed by a subsequent drying while not adversely affecting the coating process. As a non-limiting example of the solvent, it is possible to use toluene, xylene, acetone, chloroform, various alcohol-based solvents, MEK (methyl ethyl ketone), MIBK (methyl isobutyl ketone), EA (ethyl acetate), butyl acetate, DMF (dimethylformamide), DMAc (dimethylacetamide), DMSO (dimethylsulfoxide), NMP (N-methyl-pyrrolidone), and the like, and a mixture of one or two or more thereof may be used. When the first solution and the second solution are used, the solvents included in each of the solutions may also be the same as or different from each other. Even when different solvents are used in the first solution and the second solution, it is preferred that these solvents have compatibility so as to be mixed with each other.

For the process of coating the resin solution, in which the compound represented by Chemical Formula 1 is dissolved, on a base material, a roll-to-roll process may be used. For example, the process may be performed by a process including: unwinding a base material from a roll on which the base material is wound, coating the resin solution, in which the compound represented by Chemical Formula 1 is dissolved, on one surface of the base material, drying the resin solution, and then winding the base material on the roll again. When the roll-to-roll process is used, it is preferred that the viscosity of the resin solution is determined within a range in which the process may be implemented, and the viscosity may be determined within a range of, for example, 200 to 2,000 cps.

As the coating method, various publicly-known methods may be used, and for example, a die coater may also be used, and it is also possible to use various bar-coating methods such as a comma coater and a reverse comma coater.

After the coating, a drying process is performed. The drying process may be performed under conditions required for removing the solvent. For example, a color conversion film comprising a fluorescent material comprising the compound represented by Chemical Formula 1 may be obtained at a desired thickness and concentration on a base material by drying the base material under a condition in which the solvent is sufficiently volatilized from an oven disposed adjacent to a coater in a direction in which the base material proceeds during the coating process.

When the monomer which is curable by the resin matrix is used as a resin included in the solution, curing, for example, UV curing may be performed before the drying or simultaneously with the drying.

When the compound represented by Chemical Formula 1 is extruded together with a resin to produce a film, an extrusion method known in the art may be used, and for example, a color conversion film may be produced by extruding the compound represented by Chemical Formula 1 together with a resin such as a polycarbonate (PC)-based resin, a poly(meth)acrylic resin, and a styrene-acrylonitrile (SAN)-based resin.

According to an exemplary embodiment of the present specification, in the color conversion film, a proactive film or a barrier film may be provided on at least one surface thereof. As the protective film and the barrier film, films known in the art may be used.

According to an exemplary embodiment of the present specification, provided is a backlight unit comprising the above-described color conversion film. The backlight unit may have a backlight unit configuration known in the art, except that the backlight unit comprises the color conversion film. FIG. 1 illustrates a schematic view of a backlight unit structure according to an example. The backlight unit according to FIG. 1 includes a branch-type light source 101, a reflective plate 102 which surrounds the light source, a light guide plate 103 which emits light directly from the light source, or guides light reflected from the reflective plate, a reflective layer 104 which is provided on one surface of the light guide plate, and a color conversion film 105 which is provided on a surface opposite to a surface facing the reflective layer of the light guide plate. A region indicated as grey in FIG. 1 is a light-dispersion pattern 106 of the light guide plate. The light incident inside the light guide plate has an irregular light distribution due to the repetition of an optical process such as reflection, total reflection, refraction, and transmission, and a 2-dimensional light dispersion pattern may be used in order to guide the light distribution to have a uniform luminosity. However, the scope of the present invention is not limited by FIG. 1, and not only a branch-type light source but also a direct-type light source may also be used as the light source, and the reflective plate or reflective layer may be omitted or may also be replaced with another configuration, if necessary, and an additional film, for example, a light-diffusing film, a light collecting film, a brightness enhancement film, and the like may be further provided, if necessary.

According to an exemplary embodiment of the present specification, provided is a display device comprising the backlight unit. The display device is not particularly limited as long as the device is a display device comprising a backlight unit, and may be included in a TV, a monitor of a computer, a laptop computer, a mobile phone, and the like.

MODE FOR INVENTION

Hereinafter, the present specification will be described in detail with reference to the Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

The compound represented by Chemical Formula 1 may be produced by a general synthesis method such as the following Formula 1.

In Formula 1, the definitions of $L_1$, $X_1$, $R_1$ to $R_{11}$, and m are the same as those in Chemical Formula 1.

A boron-pyrromethene metal complex was synthesized by a general producing method in a reference document (Chem. Rev. 2007, 107, 4891-4932), an iodine group X was introduced through N-iodosuccinimide (NIS), and then a pentacyclic or hexacyclic ring was introduced through a Suzuki coupling.

Aryl pyrrole was synthesized according to a reference document (J. Org. Chem. 2005, 70, 5571-5578).

Preparation Example 1) Production of Compound P1

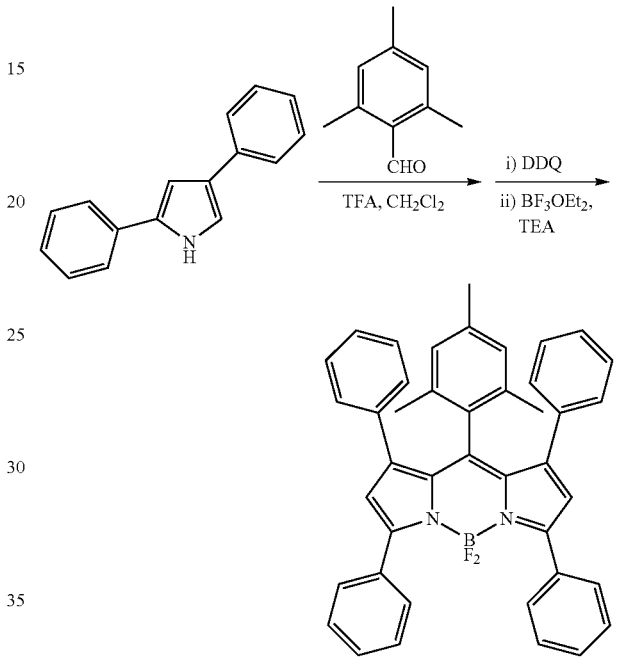

[Formula 1]

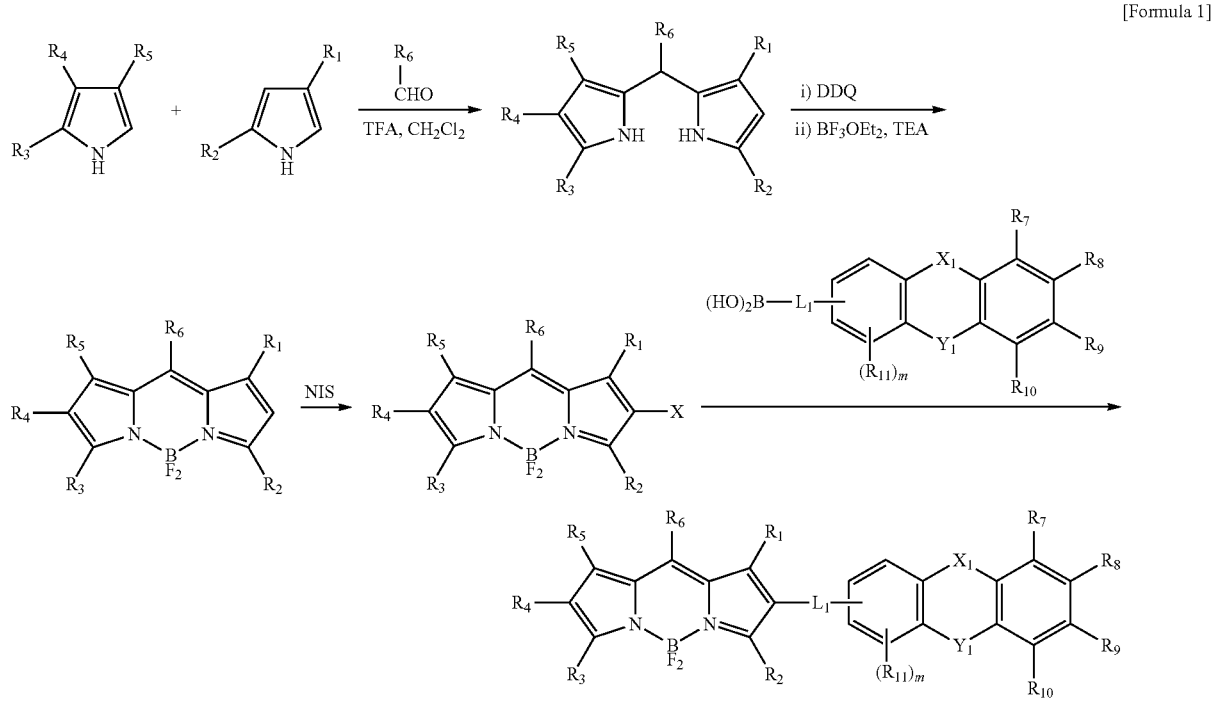

2,4-diphenyl-1H-pyrrole (3 g, 13.6 mmol) and 1,3,5-trimethylbenzaldehyde (1.0 g, 6.7 mmol) were completely dissolved in CH$_2$Cl$_2$ (100 mL), and then 2 drops of trifluoroacetic acid were added thereto, and the resulting mixture was stirred at normal temperature for 3 hours. The obtained mixture was cooled to 0° C., and then DDQ (1.8 g, 7.9 mmol) was added thereto. The resulting mixture was stirred at normal temperature for 1 hour, and then TEA (8 mL) was added dropwise thereto. After the resulting mixture was stirred for 30 minutes, BF$_3$OEt$_2$ (12 mL) was added dropwise thereto, and then the resulting mixture was stirred at normal temperature for 3 hours. The solvent was distilled under reduced pressure and removed, and then the residue was purified by column chromatography (hexane/ethyl acetate) to obtain blackish red solid P1 (2.2 g, yield: 53%).

[M−F=595]

Preparation Example 2) Production of Compound P2

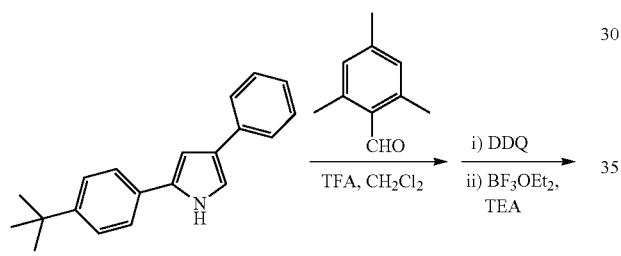

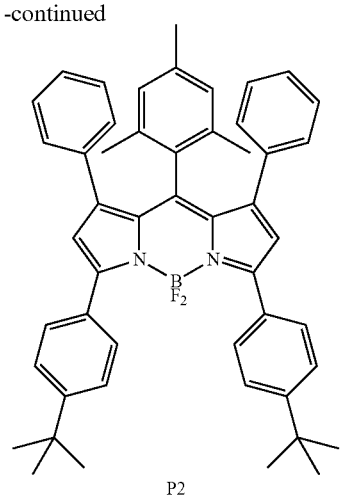

P2

A compound was synthesized by using 2-((4-tert butyl)phenyl)-4-phenyl-1H-pyrrole (2.6 g, 11.3 mmol) and 1,3,5-trimethylbenzaldehyde (0.7 g, 4.7 mmol) according to the method of producing Compound P1, and then purified by column chromatography (hexane/ethyl acetate) to obtain blackish red solid P2 (1.8 g, 52%).

[M−F=707]

Preparation Example 3) Production of Compound P3

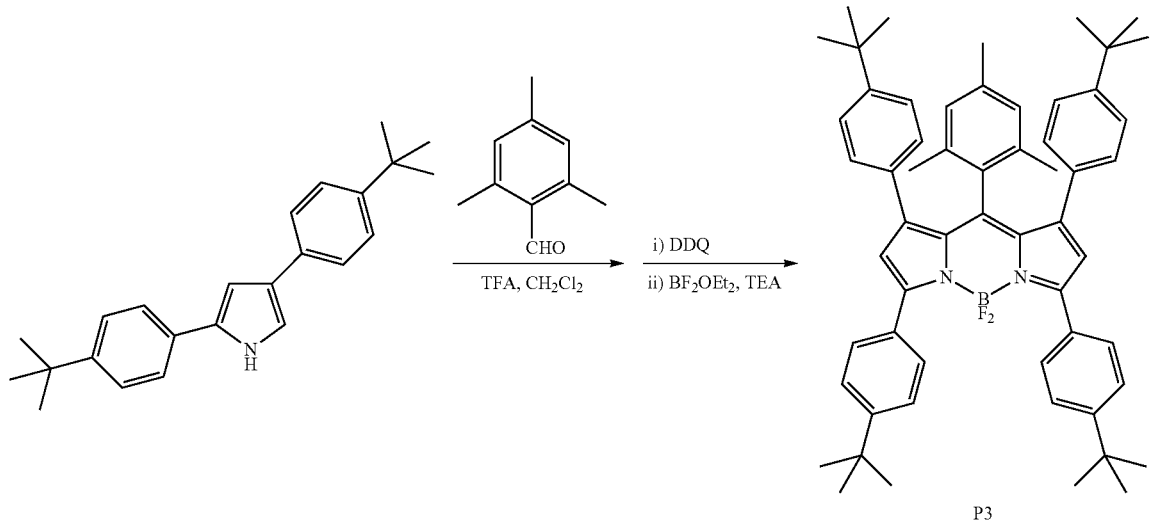

P3

A compound was synthesized by using 2.4-((4-tert butyl)phenyl)-1H-pyrrole (5.1 g, 15.3 mmol) and 1,3,5-trimethylbenzaldehyde (1.2 g, 8.0 mmol) according to the method of producing Compound P1, and then purified by column chromatography (hexane/ethyl acetate) to obtain blackish red solid P3 (3.6 g, 53%).

[M−F=819]

Preparation Example 4) Production of Compound P4

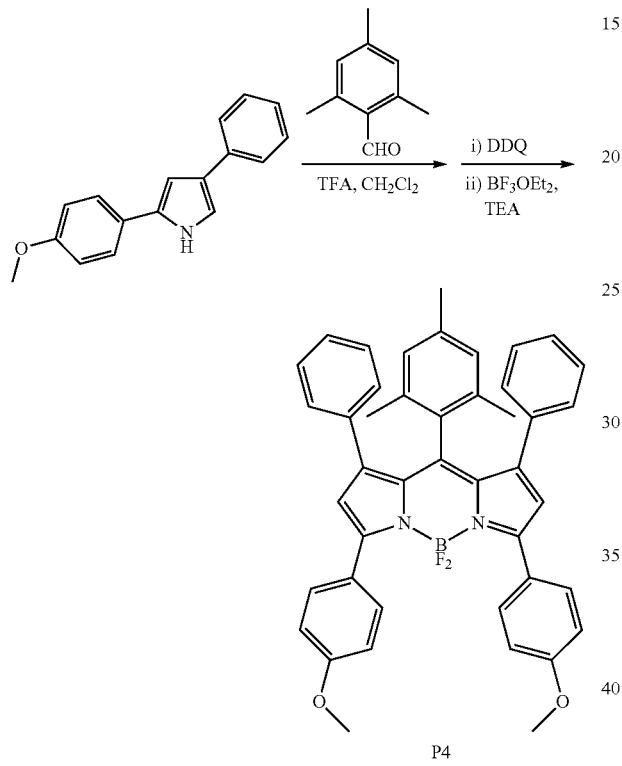

P4

A compound was synthesized by using 2-((4-methoxy) phenyl)-4-phenyl-1H-pyrrole (3.7 g, 14.9 mmol) and 1,3,5-trimethylbenzaldehyde (1.1 g, 7.4 mmol) according to the method of producing Compound P1, and then purified by column chromatography (hexane/ethyl acetate) to obtain blackish red solid P4 (3.9 g, 77%).

[M−F=655]

Preparation Example 5) Production of Compound P5

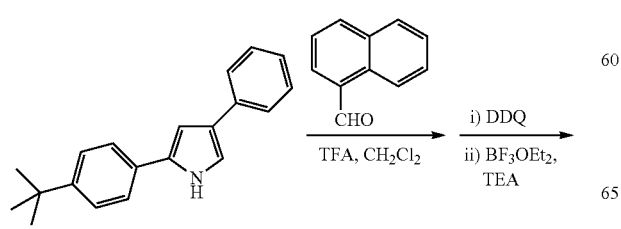

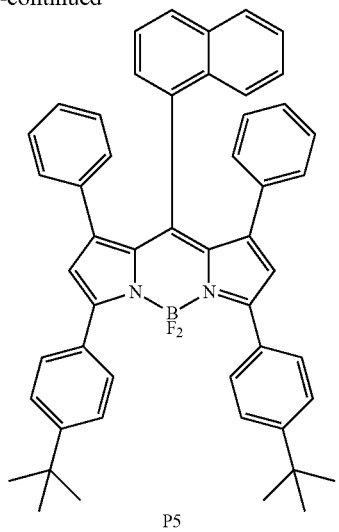

P5

A compound was synthesized by using 2-((4-tert butyl)phenyl)-4-phenyl-1H-pyrrole (3.3 g, 12 mmol) and 1-naphthaldehyde (0.93 g, 6.0 mmol) according to the method of producing Compound P1, and then purified by column chromatography (hexane/ethyl acetate) to obtain blackish red solid P5 (2.9 g, 65%).

[M−F=715]

Preparation Example 6) Production of Compound P6

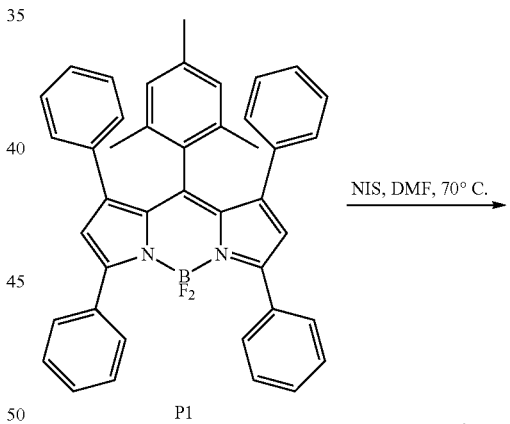

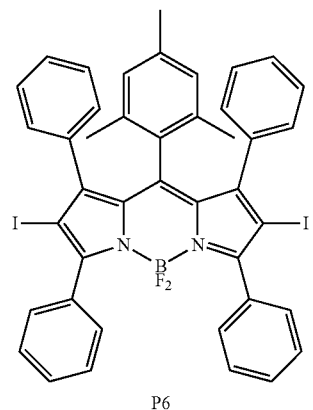

P6

Compound P1 (2.0 g, 3.2 mmol) and NIS (4.39 g, 19.5 mmol) were suspended in DMF, and then the resulting suspension was stirred at 70° C. for 5 hours. Water was added to the reactant, and the reactant was extracted with ethyl acetate. The extracted ethyl acetate solution was washed several times with water. The resulting product was distilled under reduced pressure to obtain blackish golden solid P6 (2.5 g, 88%).

[M−F=847]

Preparation Example 7) Production of Compound P7

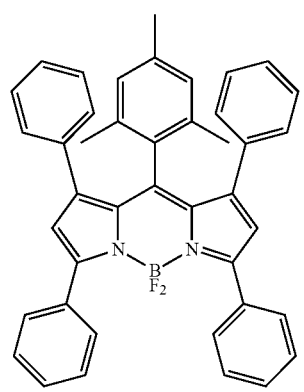

Preparation Example 8) Production of Compound P8

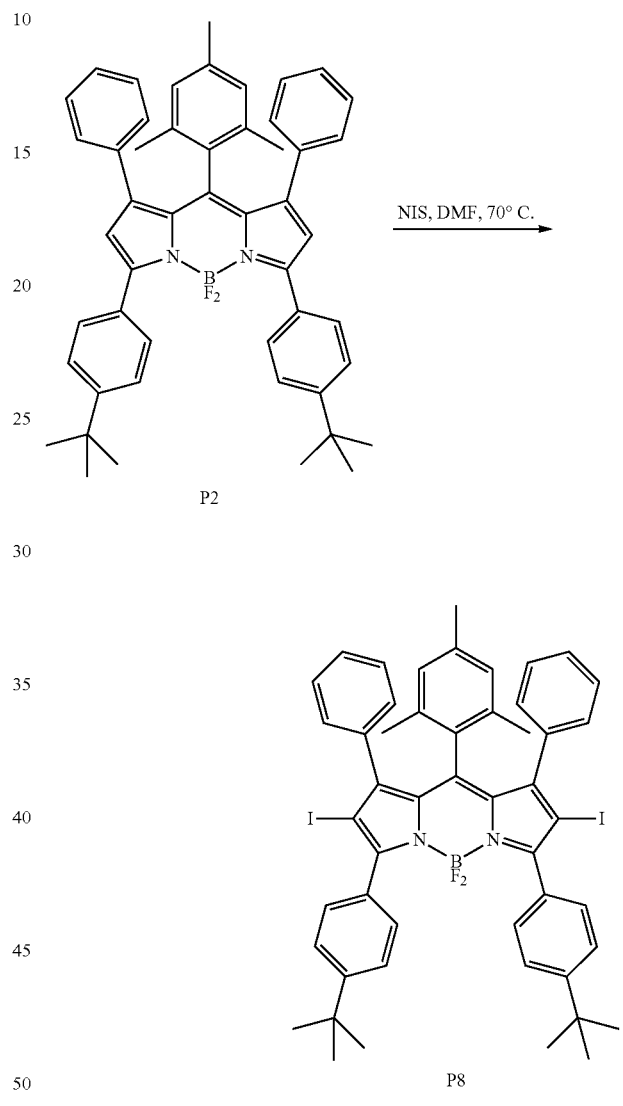

Compound P1 (2.1 g, 3.4 mmol) and NIS (1.6 g, 7.1 mmol) were suspended in DMF, and then the resulting suspension was stirred at 70° C. for 2 hours. Water was added to the reactant, and the reactant was extracted with ethyl acetate. The extracted ethyl acetate solution was washed several times with water. The resulting product was distilled under reduced pressure, and then purified by column chromatography (hexane/ethyl acetate) to obtain blackish golden solid P7 (2.0 g, 7.9%).

[M−F=721]

Compound P2 (3.1 g, 4.26 mmol) and NIS (5.6 g, 24.8 mmol) were suspended in DMF, and then the resulting suspension was stirred at 70° C. for 5 hours. Water was added to the reactant, and the reactant was extracted with ethyl acetate. The extracted ethyl acetate solution was washed several times with water. The resulting product was distilled under reduced pressure to obtain blackish golden solid P8 (3.9 g, 39.8 mmol).

[M−F=959]

Preparation Example 9) Production of Compound P9

Preparation Example 10) Production of Compound P10

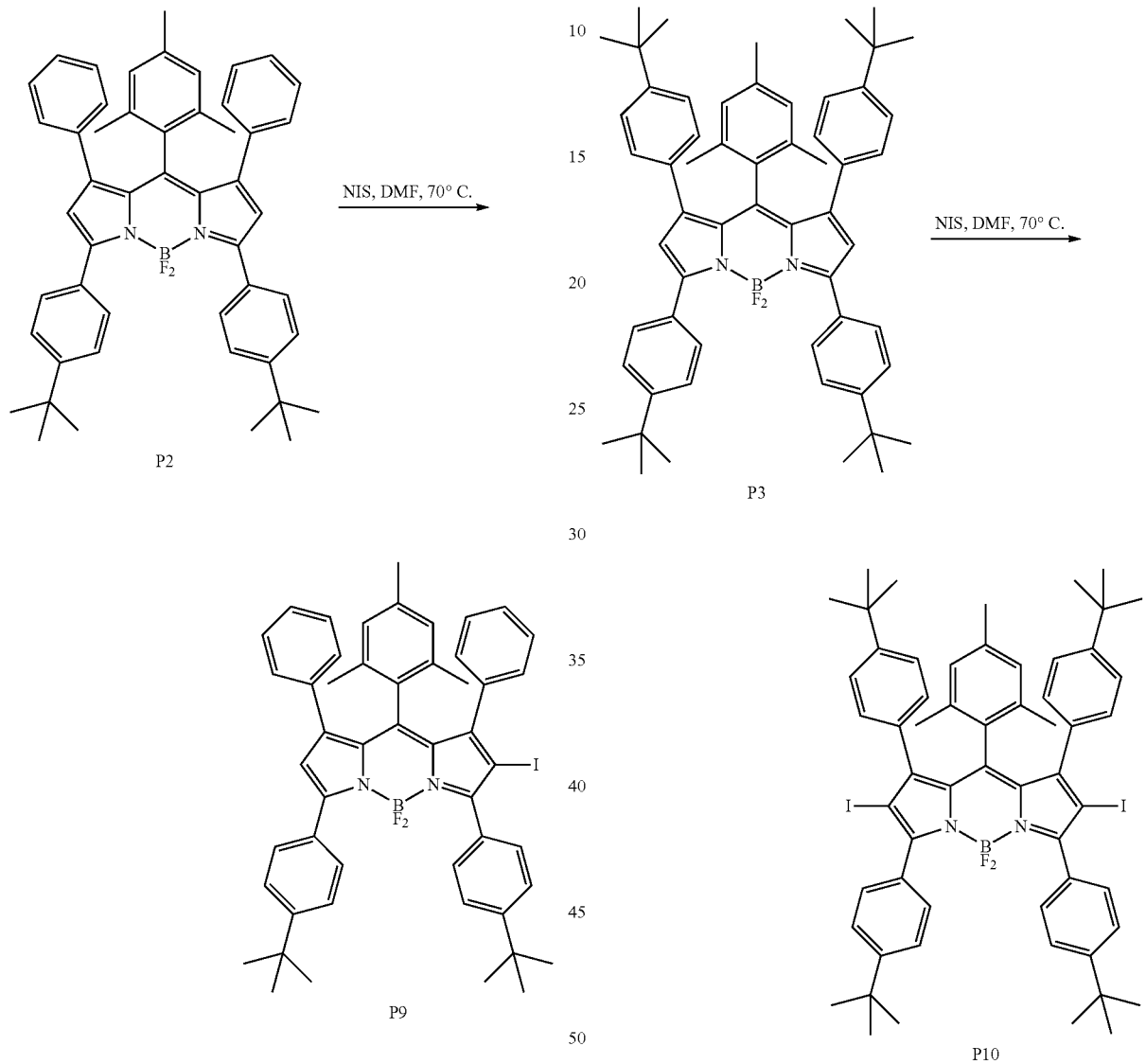

Compound P2 (2.8 g, 3.8 mmol) and NIS (1.8 g, 8.0 mmol) were suspended in DMF, and then the resulting suspension was stirred at 70° C. for 2 hours. Water was added to the reactant, and the reactant was extracted with ethyl acetate. The extracted ethyl acetate solution was washed several times with water. The resulting product was distilled under reduced pressure, and then purified by column chromatography (hexane/ethyl acetate) to obtain blackish golden solid P9 (2.4 g, 73%).

[M−F=833]

Compound P3 (2.4 g, 2.8 mmol) and NIS (3.8 g, 16.9 mmol) were suspended in DMF, and then the resulting suspension was stirred at 70° C. for 5 hours. Water was added to the reactant, and the reactant was extracted with ethyl acetate. The extracted ethyl acetate solution was washed several times with water. The resulting product was distilled under reduced pressure to obtain blackish golden solid P10 (2.6 g, 83%).

[M−F=1071]

Preparation Example 11) Production of Compound P11

Preparation Example 12) Production of Compound P12

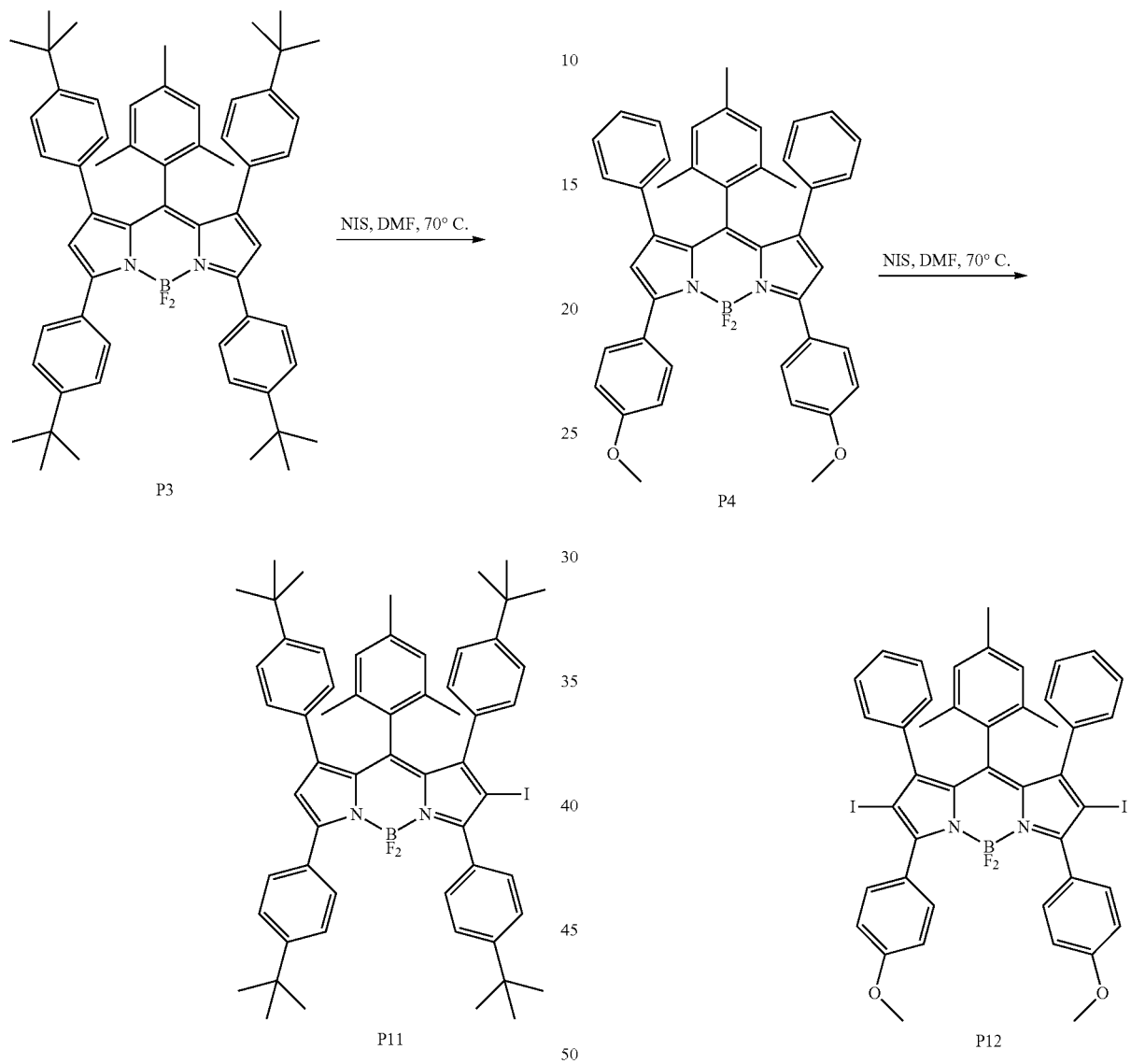

Compound P3 (3.8 g, 4.5 mmol) and NIS (2.0 g, 8.8 mmol) were suspended in DMF, and then the resulting suspension was stirred at 70° C. for 2 hours. Water was added to the reactant, and the reactant was extracted with ethyl acetate. The extracted ethyl acetate solution was washed several times with water. The resulting product was distilled under reduced pressure, and then purified by column chromatography (hexane/ethyl acetate) to obtain blackish golden solid P11 (3.1 g, 71%).

[M−F=945]

Compound P4 (3.4 g, 5.0 mmol) and NIS (6.8 g, 30 mmol) were suspended in DMF, and then the resulting suspension was stirred at 70° C. for 5 hours. Water was added to the reactant, and the reactant was extracted with ethyl acetate. The extracted ethyl acetate solution was washed several times with water. The resulting product was distilled under reduced pressure to obtain blackish golden solid P12 (3.0 g, 65%).

[M−F=907]

Preparation Example 13) Production of Compound P13

Preparation Example 14) Production of Compound P14

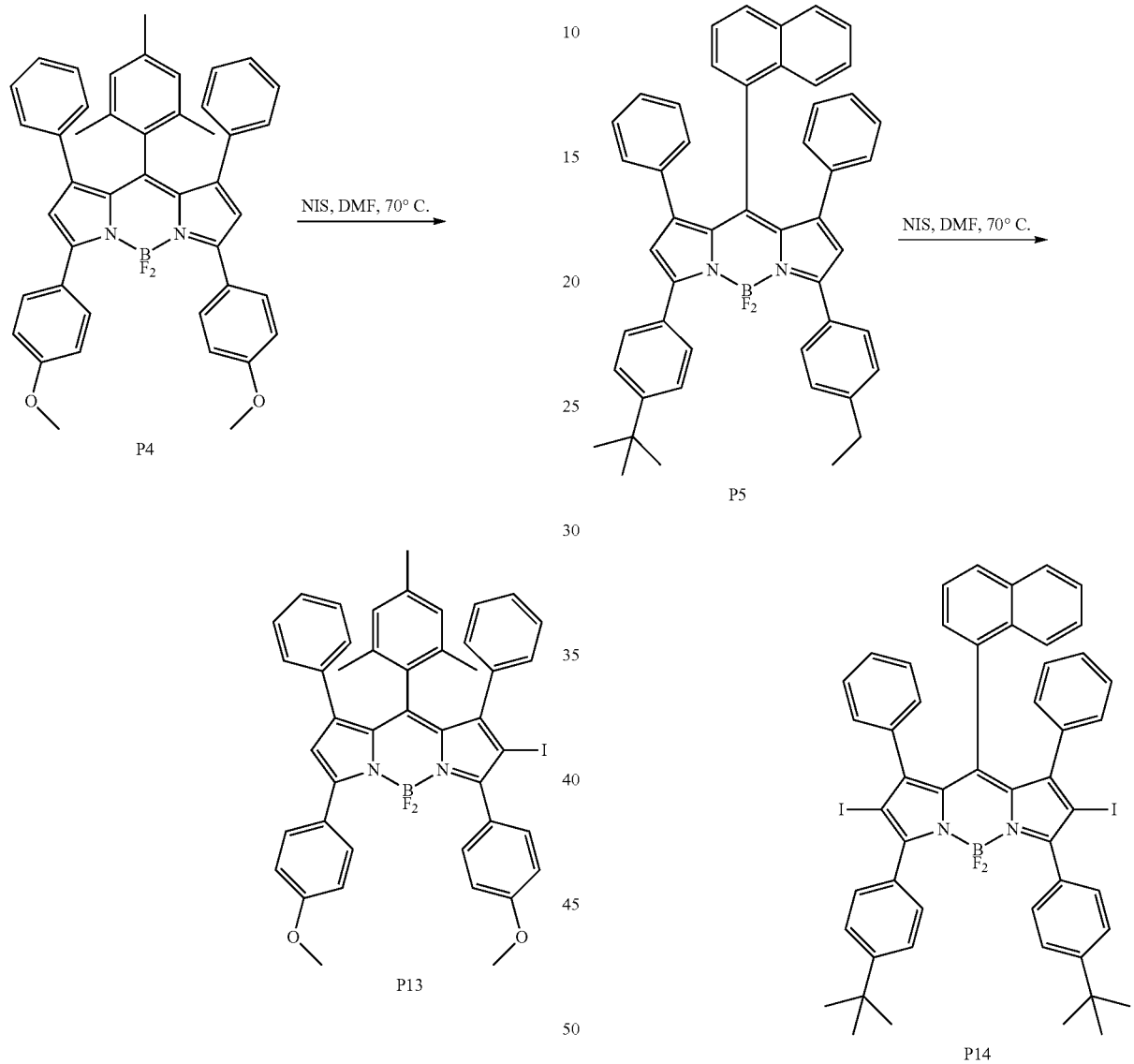

Compound P4 (2.8 g, 4.1 mmol) and NIS (1.8 g, 8.0 mmol) were suspended in DMF, and then the resulting suspension was stirred at 70° C. for 2 hours. Water was added to the reactant, and the reactant was extracted with ethyl acetate. The extracted ethyl acetate solution was washed several times with water. The resulting product was distilled under reduced pressure, and then purified by column chromatography (hexane/ethyl acetate) to obtain blackish golden solid P13 (1.8 g, 54%).

[M−F=781]

Compound P5 (3.7 g, 5.2 mmol) and NIS (7.0 g, 31 mmol) were suspended in DMF, and then the resulting suspension was stirred at 70° C. for 5 hours. Water was added to the reactant, and the reactant was extracted with ethyl acetate. The extracted ethyl acetate solution was washed several times with water. The resulting product was distilled under reduced pressure to obtain blackish golden solid P14 (3.9 g, 76%).

[M−F=967]

Preparation Example 15) Production of Compound P15

Preparation Example 16) Production of Compound 1-60

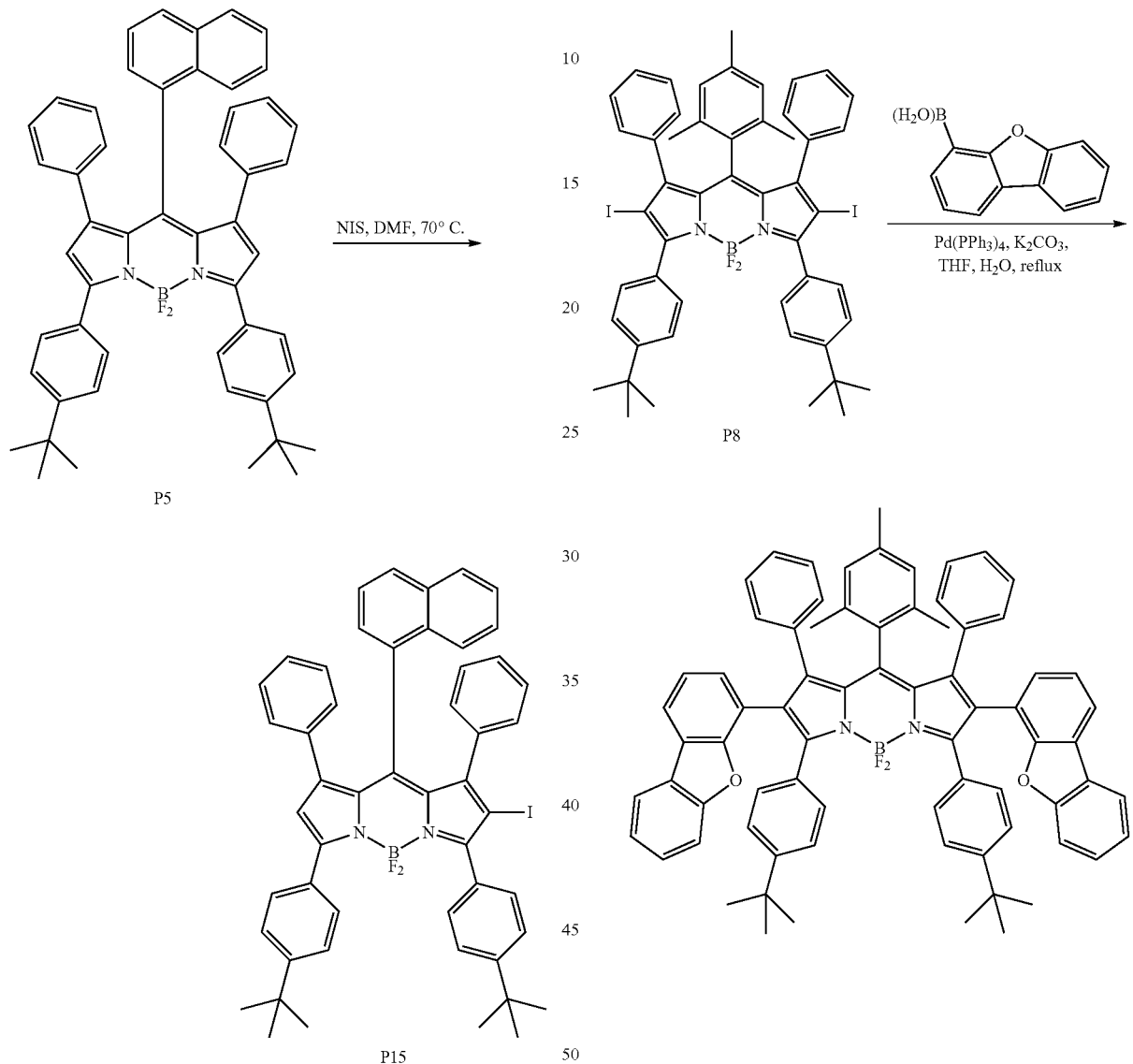

Compound P5 (2.7 g, 3.6 mmol) and NIS (1.7 g, 7.5 mmol) were suspended in DMF, and then the resulting suspension was stirred at 70° C. for 2 hours. Water was added to the reactant, and the reactant was extracted with ethyl acetate. The extracted ethyl acetate solution was washed several times with water. The resulting product was distilled under reduced pressure, and then purified by column chromatography (hexane/ethyl acetate) to obtain blackish golden solid P15 (2.4 g, 77%).

[M−F=841]

Compound P8 (1.8 g, 1.8 mmol), dibenzofuran-4-boronic acid (1.2 g, 6.1 mmol), Pd(PPh$_3$)$_4$ (50 mg, 0.04 mmol), and K$_2$CO$_3$ (1.3 g, 9.4 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-60 (0.51 g, 26%).

[M−F=1040]

Preparation Example 17) Production of Compound 1-61

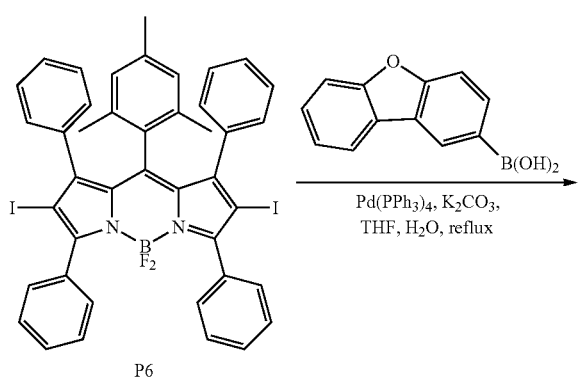

P6

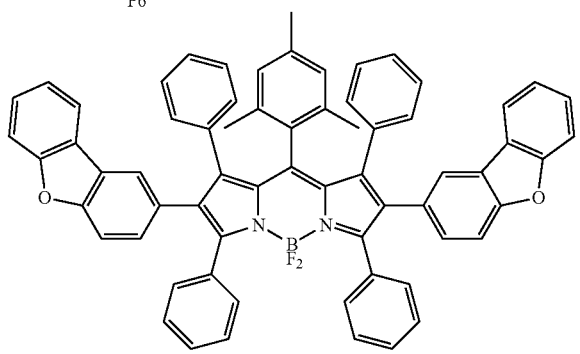

Compound P6 (1.7 g, 1.9 mmol), dibenzofuran-2-boronic acid (1.3 g, 6.1 mmol), Pd(PPh$_3$)$_4$ (50 mg, 0.04 mmol), and K$_2$CO$_3$ (1.5 g, 10 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-61 (0.7 g, 38%).

[M−F=927]

Preparation Example 18) Production of Compound 1-62

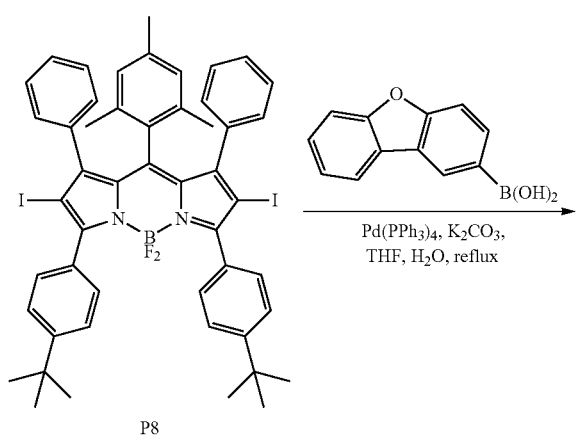

P8

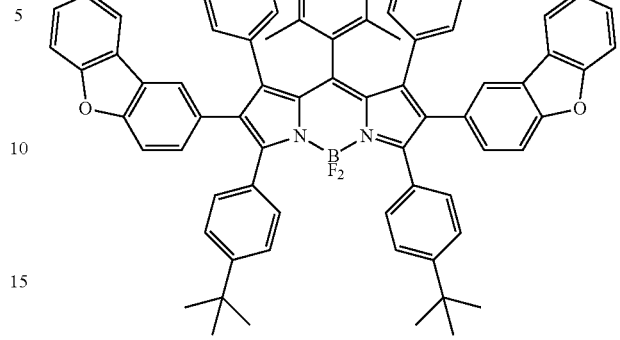

Compound P8 (2.0 g, 2.0 mmol), dibenzofuran-2-boronic acid (1.7 g, 8 mmol), Pd(PPh$_3$)$_4$ (50 mg, 0.04 mmol), and K$_2$CO$_3$ (1.8 mmol, 13 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-62 (0.8 g, 37%).

[M−F=1039]

Preparation Example 19) Production of Compound 1-65

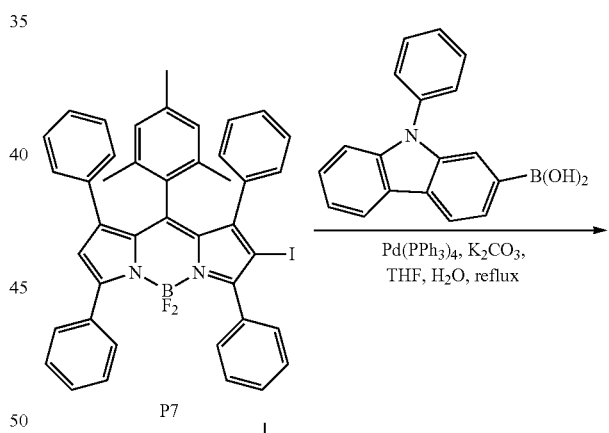

P7

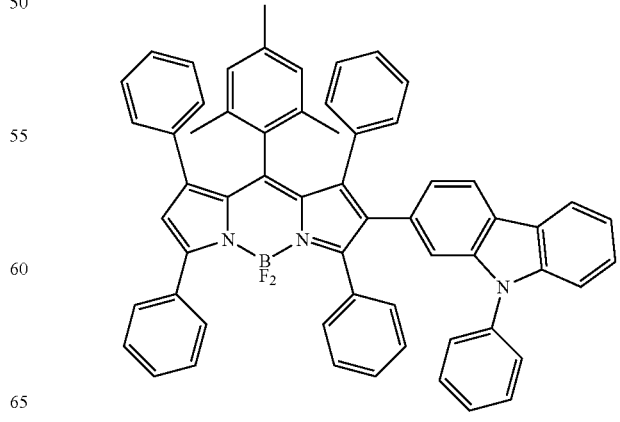

Compound P7 (1.3 g, 1.7 mmol), N-phenylcarbazole-2-boronic acid (0.9 g, 3.1 mmol), Pd(PPh$_3$)$_4$ (50 mg, 0.04 mmol), and K$_2$CO$_3$ (0.9 g, 6.5 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-65 (1.1 g, 75%).

[M–F=846]

Preparation Example 20) Production of Compound 1-66

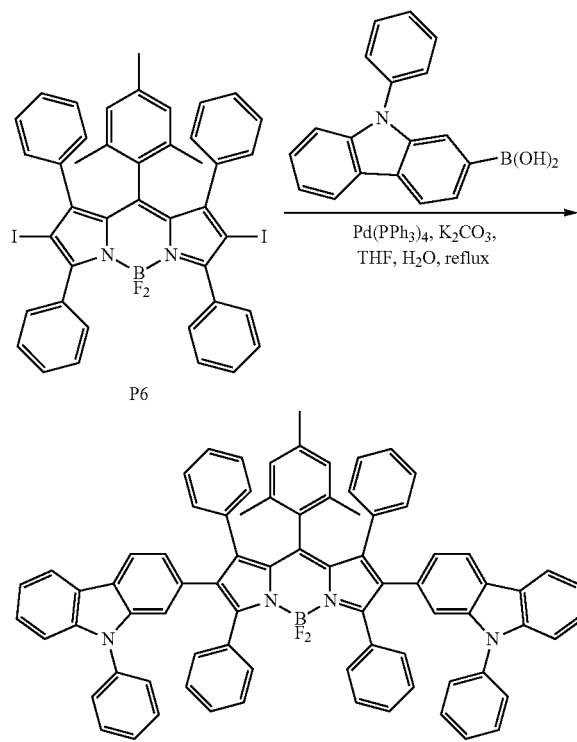

P6

Preparation Example 21) Production of Compound 1-68

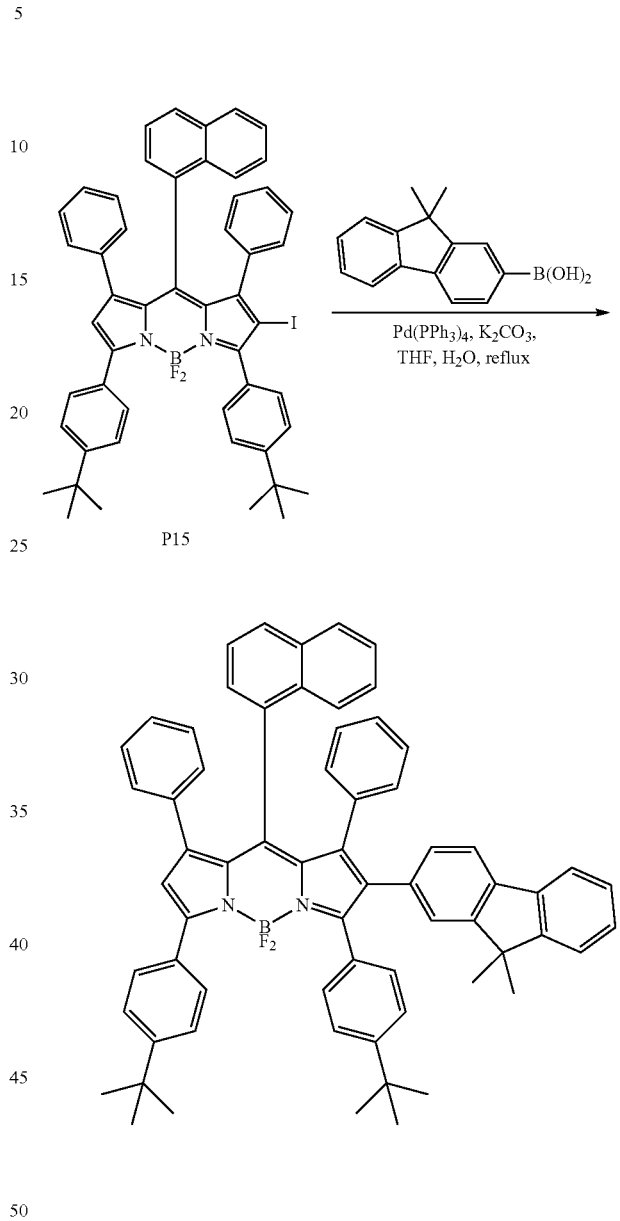

Compound P6 (1.2 g, 1.3 mmol), N-phenylcarbazole-2-boronic acid (2.2 g, 7.6 mmol), Pd(PPh$_3$)$_4$ (50 mg, 0.04 mmol), and K$_2$CO$_3$ (2.1 g, 15 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-66 (1.3 g, 90%).

[M–F=1078]

Compound P15 (1.3 g, 1.5 mmol), 9,9-dimethyl-9H-fluorene-2-boronic acid (0.9 g, 3.7 mmol), Pd(PPh$_3$)$_4$ (50 mg, 0.04 mmol), and K$_2$CO$_3$ (2.1 g, 15 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-68 (0.8 g, 56%).

[M–F=908]

Preparation Example 22) Production of Compound 1-69

Preparation Example 23) Production of Compound 1-78

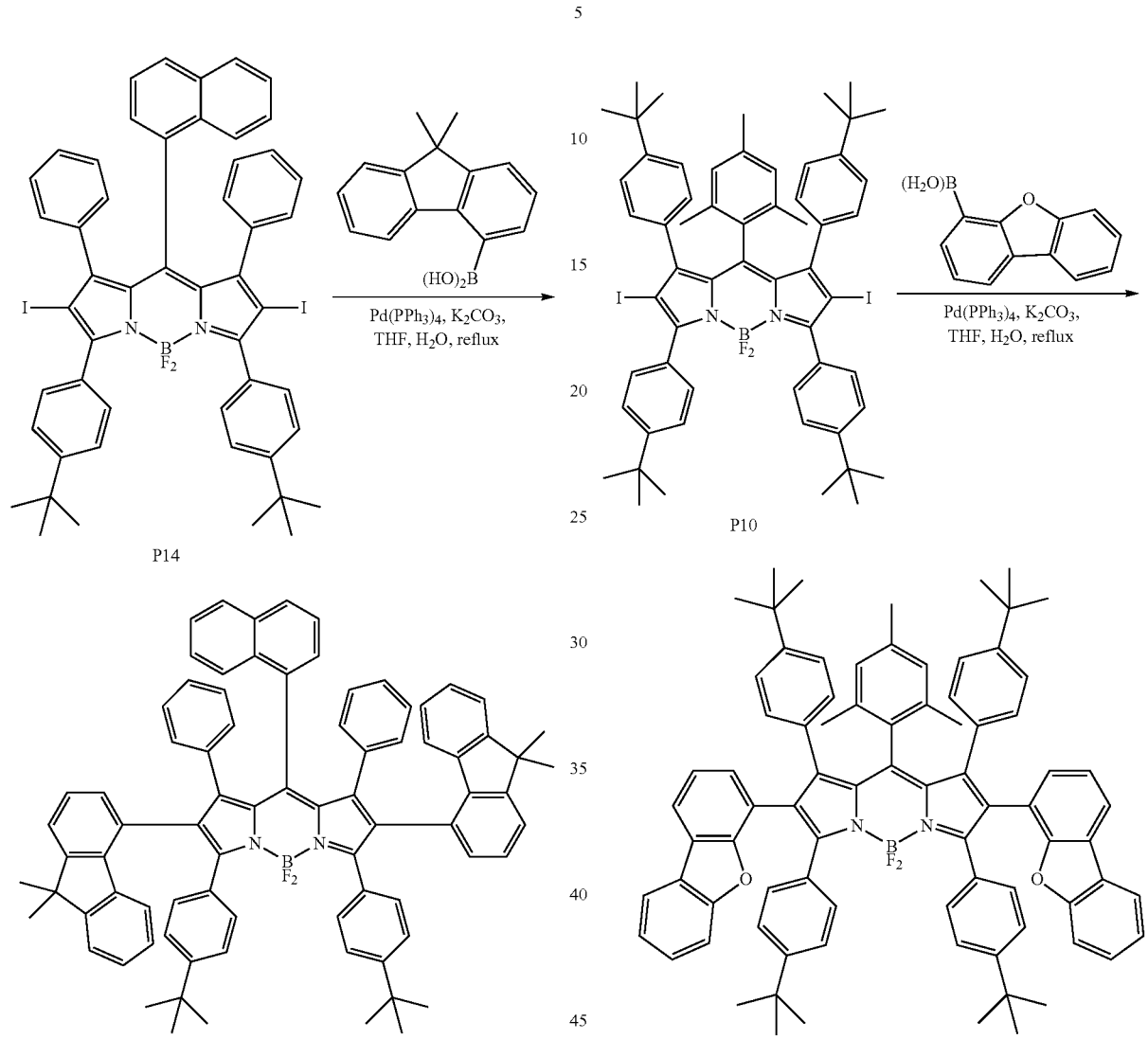

Compound P14 (1.2 g, 1.2 mmol), 9,9-dimethyl-9H-fluorene-4-boronic acid (2.2 g, 9.2 mmol), Pd(PPh$_3$)$_4$ (50 mg, 0.04 mmol), and K$_2$CO$_3$ (2.2 g, 16 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-69 (0.8 g, 59%).

[M−F=1100]

Compound P10 (2.8 g, 2.5 mmol), dibenzofuran-4-boronic acid (2.3 g, 11 mmol), Pd(PPh$_3$)$_4$ (50 mg, 0.05 mmol), and K$_2$CO$_3$ (2.5 g, 18 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-78 (1.9 g, 64%).

[M−F=1152]

Preparation Example 24) Production of Compound 1-82

Preparation Example 25) Production of Compound 1-83

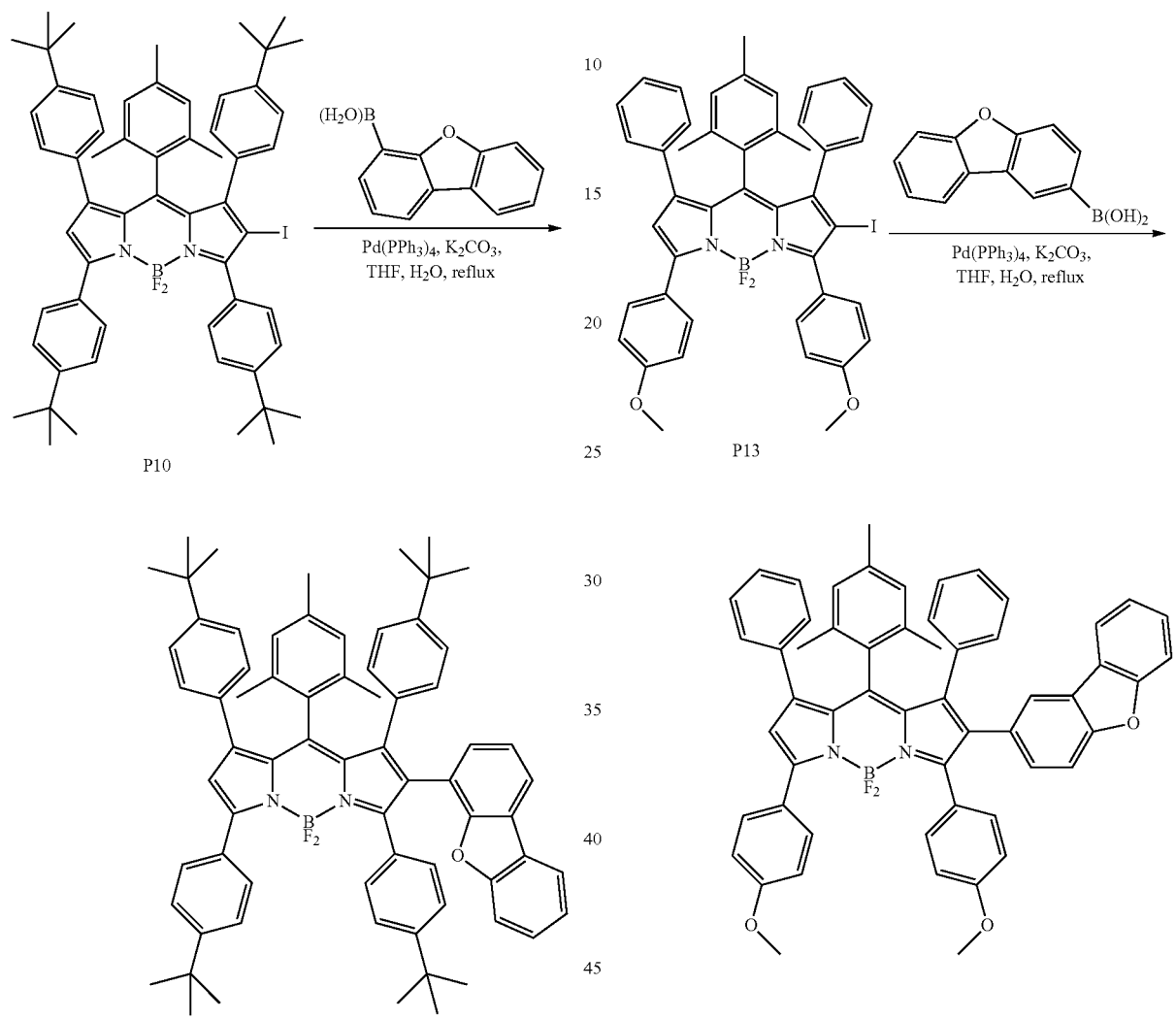

Compound P11 (1.9 g, 1.9 mmol), dibenzofuran-4-boronic acid (0.8 g, 4.0 mmol), Pd(PPh$_3$)$_4$ (50 mg, 0.04 mmol), and K$_2$CO$_3$ (0.9 g, 6.5 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-82 (1.3 g, 67%).

[M−F=986]

Compound P13 (1.6 g, 2.0 mmol), dibenzofuran-2-boronic acid (1.0 g, 4.7 mmol), Pd(PPh$_3$)$_4$ (50 mg, 0.05 mmol), and K$_2$CO$_3$ (1.0 g, 7.2 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-83 (1.0 g, 59%).

[M−F=821]

Preparation Example 26) Production of Compound 1-84

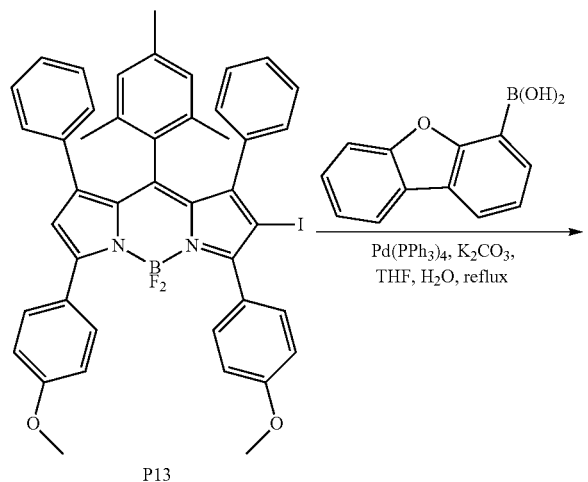

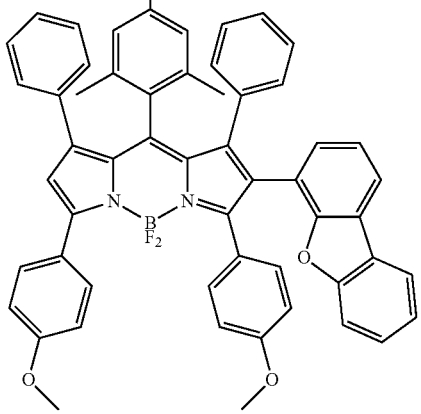

Compound P13 (2.2 g, 2.7 mmol), dibenzofuran-4-boronic acid (1.0 g, 4.7 mmol), Pd(PPh$_3$)$_4$ (50 mg, 0.05 mmol), and K$_2$CO$_3$ (1.0 g, 7.2 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-84 (1.3 g, 55%).

[M−F=821]

Preparation Example 27) Production of Compound 1-85

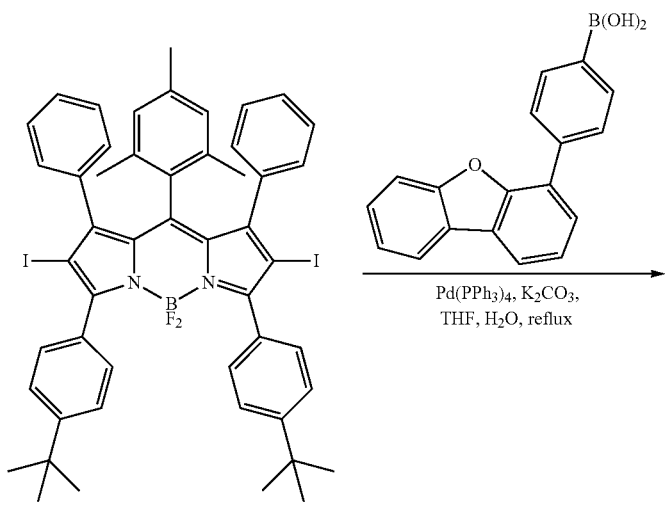

-continued

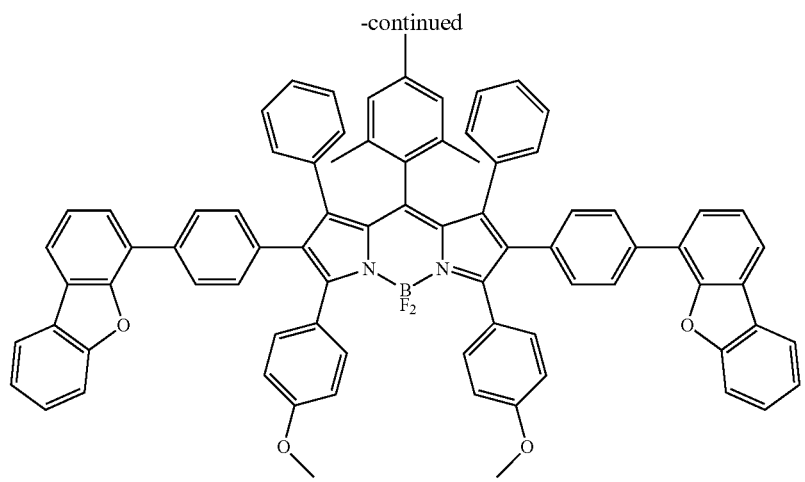

Compound P8 (2.1 g, 2.1 mmol), (4-(dibenzofuran-4)phenyl)boronic acid (1.8 g, 6.2 mmol), Pd(PPh$_3$)$_4$ (50 mg, 0.04 mmol), and K$_2$CO$_3$ (1.8 g, 13 mmol) were suspended in THF/H$_2$O, and then the resulting suspension was refluxed and stirred for 12 hours. After the temperature was increased to normal temperature, water was added thereto and the resulting product was extracted with ethyl acetate. The organic layer was separated, dried over anhydrous magnesium sulfate, and then distilled under reduced pressure. The resulting product was purified by column chromatography (hexane/ethyl acetate) to obtain blackish red solid Compound 1-85 (1.0 g, 39%).

[M-F=1191]

Comparative Example 1

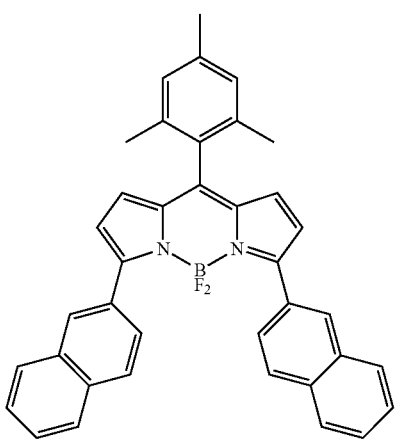

A first solution was produced by dissolving an organic phosphor having the structural formula in a reference document (Chem. Eur. J. 2011, 17, 3069-3073) in a solvent DMF. A second solution was produced by dissolving a thermoplastic resin PMMA in the solvent DMF. The first solution and the second solution were mixed such that the amount of the organic phosphor was 0.5 part by weight based on 100 parts by weight of PMMA, and the resulting mixture was uniformly mixed. The solid content of the mixed solution was 20 wt %, and the viscosity thereof was 200 cps. A color conversion film was produced by coating the solution on a PET base material, and then drying the solution. The brightness spectrum of the produced color conversion film was measured by a spectroradiometer (SR series manufactured by Topcon, Inc.). Specifically, the produced color conversion film was stacked on one surface of a light guide plate of a backlight unit comprising an LED blue backlight (a maximum light emission wavelength of 450 nm) and the light guide plate, a prism sheet and a DBEF film were stacked on the color conversion film, and then the brightness spectrum of the film was measured. An initial value was set, such that the luminosity of the blue LED light was 600 nit with or without the color conversion film when the brightness spectrum was measured.

From the color conversion film of the compound, light was emitted at 635 nm under the blue LED light, and the full width at half maximum was 55 nm. The color conversion film was stacked on the blue backlight, and then the ratio of the amount of decrease in blue fluorescence to the amount of increase in red fluorescence was 0.92. While the blue backlight was driven, the intensity of red fluorescence was decreased by 25% under the conditions of a temperature of 60° C. and a relative humidity of 90% after 500 hours. Further, the intensity of red fluorescence was decreased by 20% under the conditions of a temperature of 85° C. and a relative humidity of 85% after 500 hours without driving the blue backlight.

Comparative Example 2

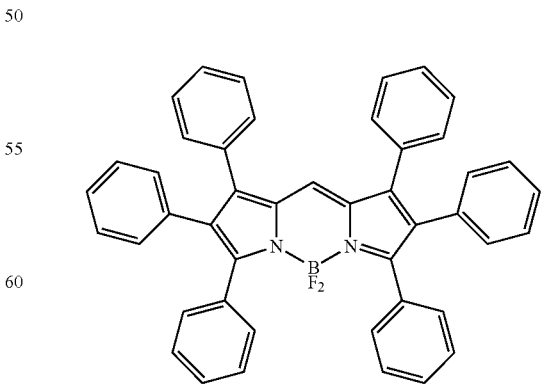

A color conversion film was produced in the same manner as in Comparative Example 1, except that an organic phosphor in a reference document (Chem. Lett. 2008, 37, 1094-1095) was used instead of the organic phosphor in Comparative Example 1.

From the color conversion film of the compound, light was emitted at 620 nm under the blue LED light, and the full width at half maximum was 51 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 30% under the conditions of a temperature of 60° C. and a relative humidity of 90% after 500 hours. Further, the intensity of red fluorescence was decreased by 15% under the conditions of a temperature of 85° C. and a relative humidity of 85% after 500 hours without driving the blue backlight.

Comparative Example 3

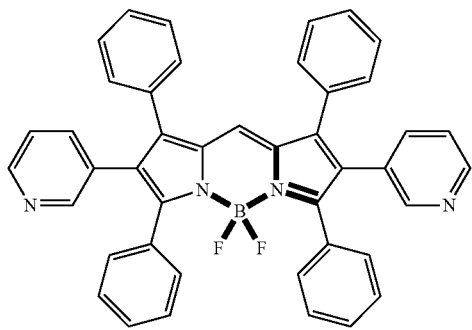

A color conversion film was produced in the same manner as in Comparative Example 1, except that the above organic phosphor in Comparative Example 3 was used instead of the organic phosphor in Comparative Example 1.

From the color conversion film of the compound, light was emitted at 640 nm under the blue LED light, and the full width at half maximum was 53 nm. The color conversion film was stacked on the blue backlight, and then the ratio of the amount of decrease in blue fluorescence to the amount of increase in red fluorescence was 0.92. While the blue backlight was driven, the intensity of red fluorescence was decreased by 25% under the conditions of a temperature of 60° C. and a relative humidity of 90% after 500 hours. Further, the intensity of red fluorescence was decreased by 25% under the conditions of a temperature of 85° C. and a relative humidity of 85% after 500 hours without driving the blue backlight.

Example 1

A color conversion film was produced in the same manner as in Comparative Example 1, except that Compound 1-60 was used instead of the organic phosphor in Comparative Example 1.

From the color conversion film of the compound, light was emitted at 633 nm under the blue LED light, and the full width at half maximum was 49 nm. The color conversion film was stacked on the blue backlight, and then the ratio of the amount of decrease in blue fluorescence to the amount of increase in red fluorescence was 0.99. While the blue backlight was driven, the intensity of red fluorescence was decreased by 2% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 2

A color conversion film was produced in the same manner as in Comparative Example 1, except that Compound 1-61 was used instead of the organic phosphor in Comparative Example 1.

From the color conversion film of the compound, light was emitted at 624 nm under the blue LED light, and the full width at half maximum was 53 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 3% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 3

A color conversion film was produced in the same manner as in Comparative Example 1, except that Compound 1-62 was used instead of the organic phosphor in Comparative Example 1.

From the color conversion film of the compound, light was emitted at 645 nm under the blue LED light, and the full width at half maximum was 51 nm. The color conversion film was stacked on the blue backlight, and then the ratio of the amount of decrease in blue fluorescence to the amount of increase in red fluorescence was 1.00. While the blue backlight was driven, the intensity of red fluorescence was decreased by 5% under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 4

A color conversion film was produced in the same manner as in Comparative Example 1, except that Compound 1-65 was used instead of the organic phosphor in Comparative Example 1.

From the color conversion film of the compound, light was emitted at 640 nm under the blue LED light, and the full width at half maximum was 50 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 4% under the conditions of a temperature of 60° C. and a relative humidity of 90% after 500 hours. Further, the intensity of red fluorescence was decreased by 5% under the conditions of a temperature of 85° C. and a relative humidity of 85% after 500 hours without driving the blue backlight.

Example 5

A color conversion film was produced in the same manner as in Comparative Example 1, except that Compound 1-66 was used instead of the organic phosphor in Comparative Example 1.

From the color conversion film of the compound, light was emitted at 650 nm under the blue LED light, and the full width at half maximum was 56 nm. The color conversion film was stacked on the blue backlight, and then the ratio of the amount of decrease in blue fluorescence to the amount of increase in red fluorescence was 0.90. While the blue backlight was driven, the intensity of red fluorescence was decreased by 8% under the conditions of a temperature of 60° C. and a relative humidity of 90% after 500 hours. Further, the intensity of red fluorescence was decreased by 7% under the conditions of a temperature of 85° C. and a relative humidity of 85% after 500 hours without driving the blue backlight.

Example 6

A color conversion film was produced in the same manner as in Comparative Example 1, except that Compound 1-68 was used instead of the organic phosphor in Comparative Example 1.

From the color conversion film of the compound, light was emitted at 624 nm under the blue LED light, and the full width at half maximum was 49 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 5% under the conditions of a temperature of 60° C. and a relative humidity of 90% after 500 hours. Further, the intensity of red fluorescence was decreased by 4% under the conditions of a temperature of 85° C. and a relative humidity of 85% after 500 hours without driving the blue backlight.

Example 7

A color conversion film was produced in the same manner as in Comparative Example 1, except that Compound 1-69 was used instead of the organic phosphor in Comparative Example 1.

From the color conversion film of the compound, light was emitted at 632 nm under the blue LED light, and the full width at half maximum was 48 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 2% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 8

A color conversion film was produced in the same manner as in Comparative Example 1, except that Compound 1-78 was used instead of the organic phosphor in Comparative Example 1.

From the color conversion film of the compound, light was emitted at 635 nm under the blue LED light, and the full width at half maximum was 48 nm. The color conversion film was stacked on the blue backlight, and then the ratio of the amount of decrease in blue fluorescence to the amount of increase in red fluorescence was 0.99. While the blue backlight was driven, the intensity of red fluorescence was decreased by 2% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 9

A color conversion film was produced in the same manner as in Comparative Example 1, except that Compound 1-82 was used instead of the organic phosphor in Comparative Example 1.

From the color conversion film of the compound, light was emitted at 628 nm under the blue LED light, and the full width at half maximum was 47 nm. The color conversion film was stacked on the blue backlight, and then the ratio of the amount of decrease in blue fluorescence to the amount of increase in red fluorescence was 0.98. While the blue backlight was driven, the intensity of red fluorescence was decreased by 2% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

Example 10

A color conversion film was produced in the same manner as in Comparative Example 1, except that Compound 1-85 was used instead of the organic phosphor in Comparative Example 1.

From the color conversion film of the compound, light was emitted at 655 nm under the blue LED light, and the full width at half maximum was 54 nm. The color conversion film was stacked on the blue backlight, and then the ratio of the amount of decrease in blue fluorescence to the amount of increase in red fluorescence was 0.96. While the blue backlight was driven, the intensity of red fluorescence was decreased by 2% or less under the conditions of a temperature of 60° C. and a relative humidity of 90% after 500 hours. Further, the intensity of red fluorescence was decreased by 2% or less under the conditions of a temperature of 85° C. and a relative humidity of 85% after 500 hours without driving the blue backlight.

From the foregoing, it can be seen that when the compound of the present specification is applied to a color conversion film, it is possible to improve light emitting efficiency, decrease a full width at half maximum, and implement a long service life. The color conversion film is useful for a display device which needs high color gamut and high efficiency.

EXPLANATION OF REFERENCE NUMERALS AND SYMBOLS

101: Branch-type light source
102: Reflective plate
103: Light guide plate
104: Reflective layer
105: Color conversion film
106: Light-dispersion pattern

The invention claimed is:
1. A compound represented by the following Chemical Formula 1:

[Chemical Formula 1]

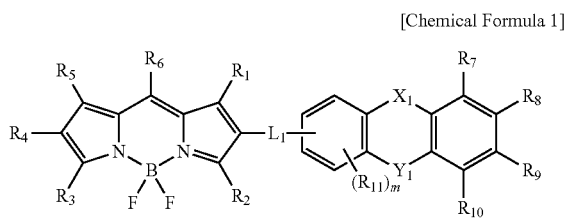

in Chemical Formula 1,
$L_1$ is a direct bond; a substituted or unsubstituted alkylene group; or a substituted or unsubstituted arylene group,
$X_1$ is $CR_{12}R_{13}$, $NR_{14}$, O, or S,
$Y_1$ is a direct bond, $CR_{15}R_{16}$, or O,
$R_1$ to $R_{16}$ are the same as or different from each other, and are each independently hydrogen; deuterium; a halogen group; a nitrile group; a nitro group; a carbonyl group; a carboxyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted amine group; a substituted or unsubstituted aryl group; or a substituted or unsubstituted heterocyclic group, or any adjacent two of $R_7$ to $R_{10}$ are optionally linked to each other to form a substituted or unsubstituted hydrocarbon ring; or a substituted or unsubstituted hetero ring, and m is an integer of 1 to 3.

2. The compound of claim 1, wherein the compound represented by Chemical Formula 1 is represented by the following Chemical Formula 2:

[Chemical Formula 2]

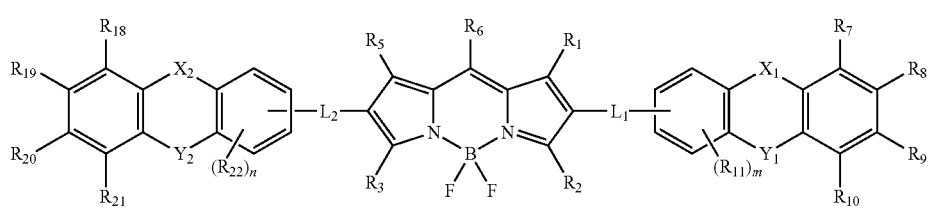

in Chemical Formula 2,
the definitions of $L_1$, $X_1$, $Y_1$, $R_1$ to $R_3$, $R_5$ to $R_{11}$, and m are the same as those in Chemical Formula 1,
$L_2$ is a direct bond; a substituted or unsubstituted alkylene group; or a substituted or unsubstituted arylene group,
$X_2$ is $CR_{23}R_{24}$, $NR_{25}$, O, or S,
$Y_2$ is a direct bond, $CR_{26}R_{27}$, or O, $R_{18}$ to $R_{27}$ are the same as or different from each other, and are each independently hydrogen; deuterium; a halogen group; a nitrile group; a nitro group; a carbonyl group; a carboxyl group; an ester group; an imide group; an amide group; a sulfonate group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted amine group; a substituted or unsubstituted aryl group; or a substituted or unsubstituted heterocyclic group, or any adjacent two of $R_{18}$ to $R_{21}$ are optionally linked to each other to form a substituted or unsubstituted hydrocarbon ring; or a substituted or unsubstituted hetero ring, and n is an integer of 1 to 3.

3. The compound of claim 1, wherein in the compound represented by Chemical Formula 1, a maximum light emission peak in a film state is present within 520 nm to 550 nm.

4. The compound of claim 1, wherein in the compound represented by Chemical Formula 1, a maximum light emission peak in a film state is present within 610 nm to 650 nm.

5. The compound of claim 1, wherein in the compound represented by Chemical Formula 1, a maximum light emission peak in a film state is present within 610 nm to 650 nm, and a full width at half maximum of the light emission peak is 60 nm or less.

6. The compound of claim 1, wherein the compound represented by Chemical Formula 1 has quantum efficiency of 0.9 or more.

7. The compound of claim 1, wherein in the compound represented by Chemical Formula 1, a ratio of an amount of decrease in blue fluorescence to an amount of increase in red fluorescence is 0.96 or more in a film state during a measurement of a brightness spectrum when a blue backlight has a maximum light emission wavelength of 450 nm, and a blue LED light has a luminosity of 600 nit.

8. The compound of claim 1, wherein $R_1$ to $R_6$ are the same as or different from each other, and are each independently hydrogen; a halogen group; a nitrile group; a sulfonate group; a carboxyl group; a substituted or unsubstituted alkyl group; a substituted or unsubstituted cycloalkyl group; a substituted or unsubstituted aryl group; or a substituted or unsubstituted heterocyclic group.

9. The compound of claim 1, wherein any adjacent two of R_7 to R_10 are linked to each other to form a substituted or unsubstituted hydrocarbon ring.
10. The compound of claim 1, wherein the compound represented by Chemical Formula 1 is any one selected from the following compounds 1-1 to 1-111:
Compound 1-1
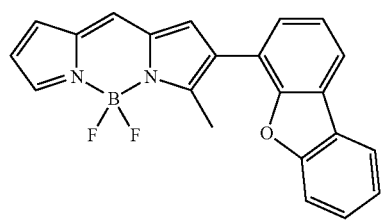
Compound 1-2
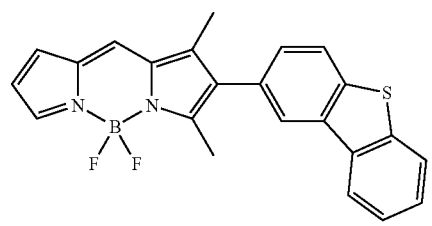
Compound 1-3
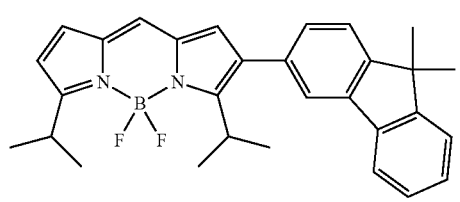
Compound 1-4
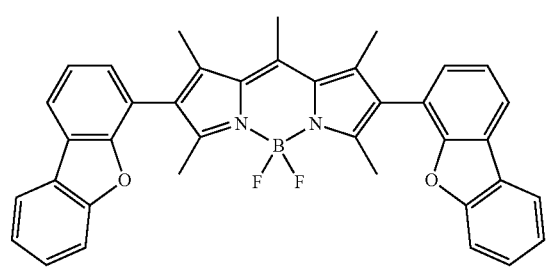
Compound 1-5
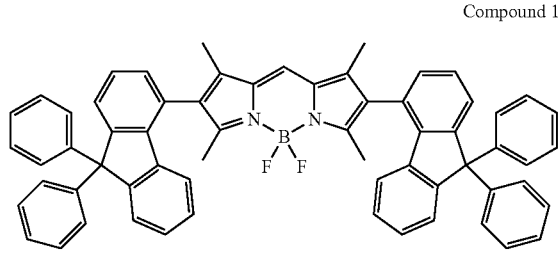
Compound 1-6
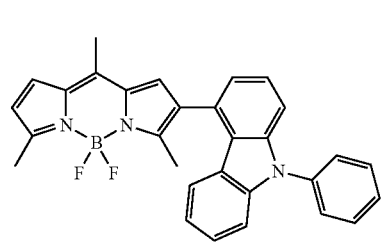
Compound 1-7
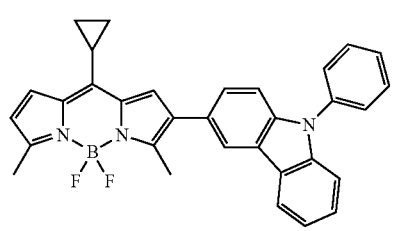
Compound 1-8
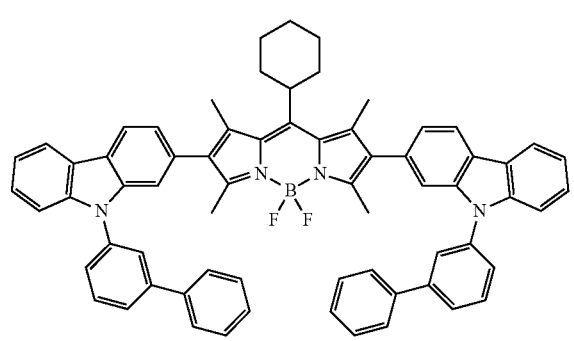

Compound 1-9
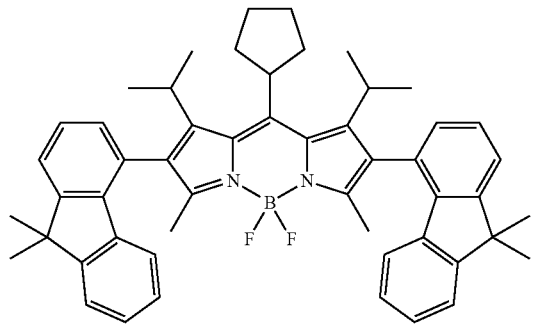
Compound 1-10
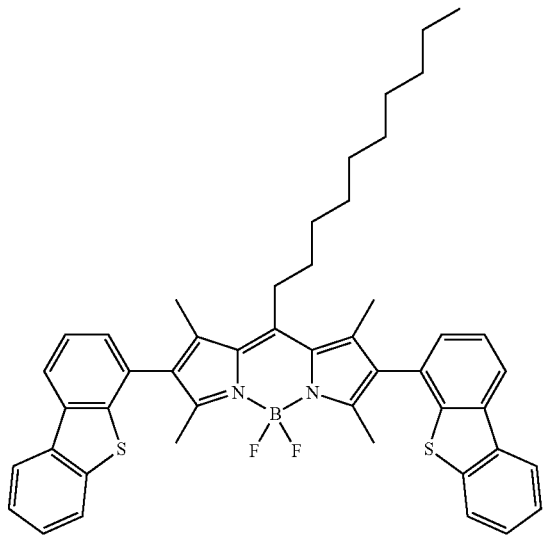
Compound 1-11
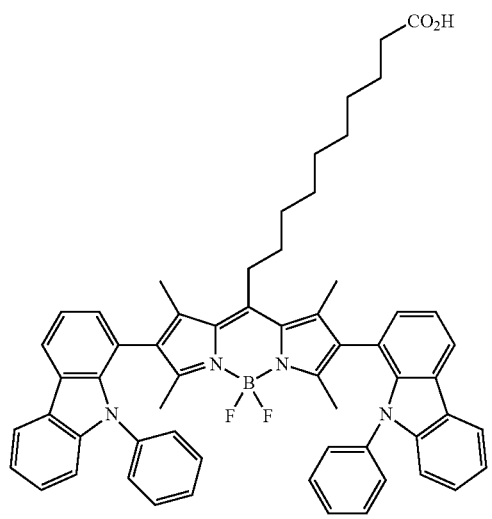
Compound 1-12
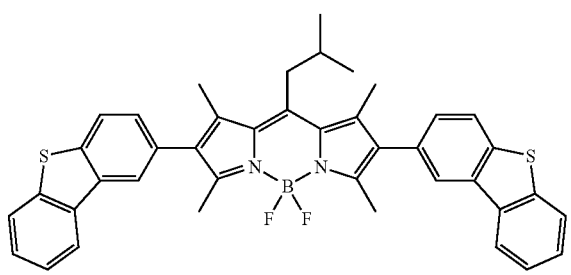
Compound 1-13
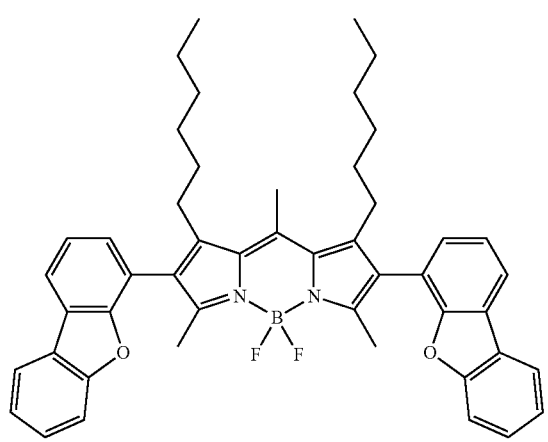
Compound 1-14
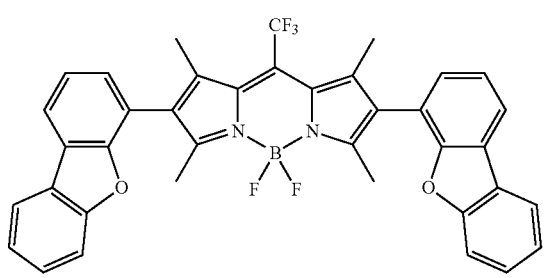

-continued
Compound 1-15
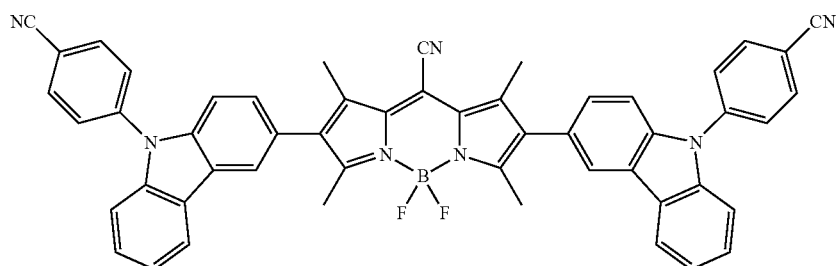
Compound 1-16
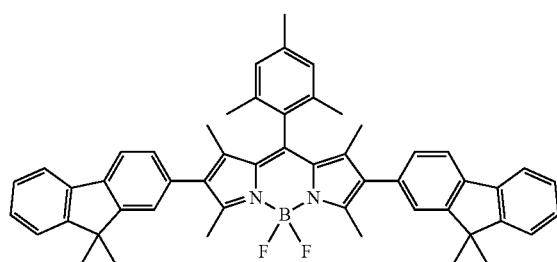
Compound 1-17
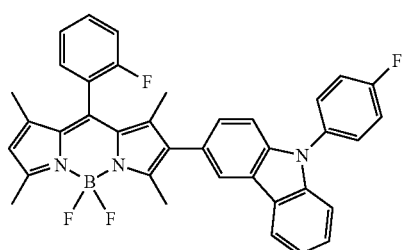
Compound 1-18
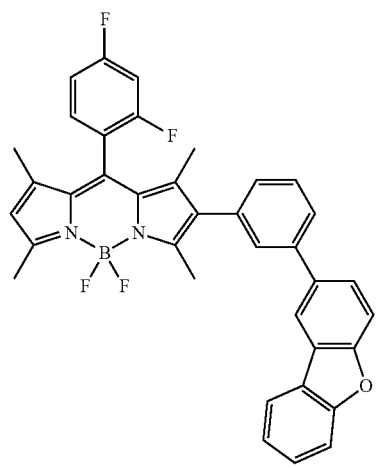
Compound 1-19
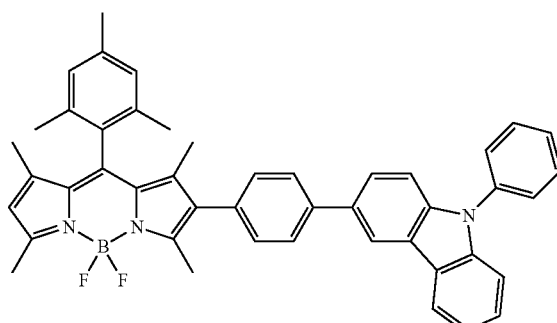
Compound 1-20
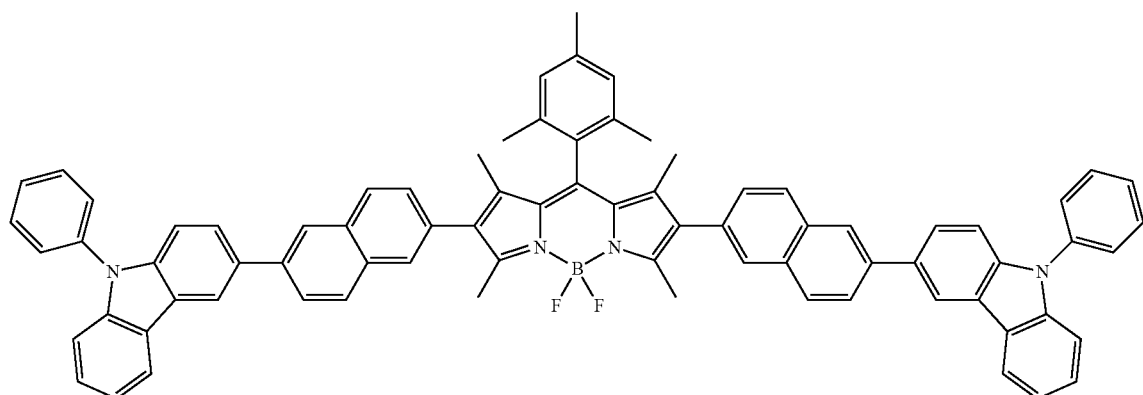

-continued
Compound 1-21
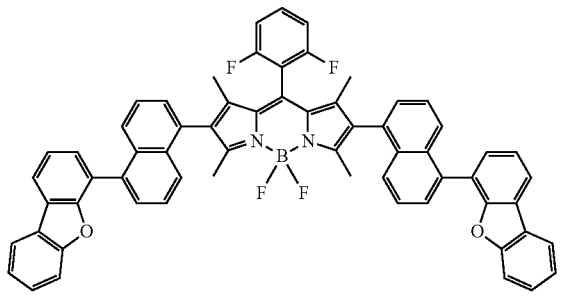
Compound 1-22
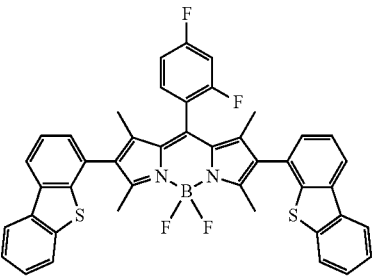
Compound 1-23
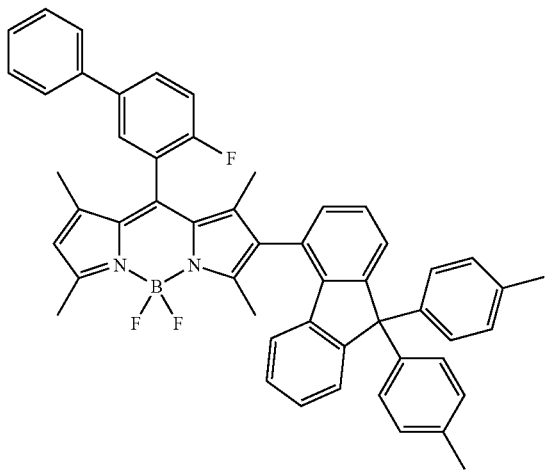
Compound 1-24
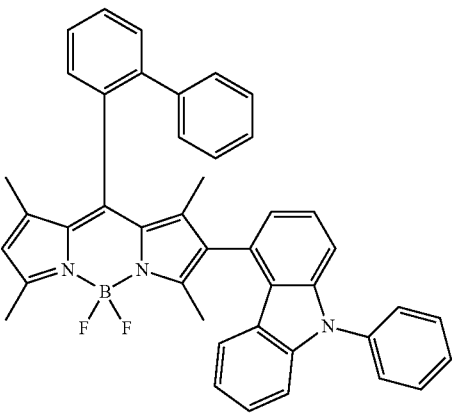
Compound 1-25
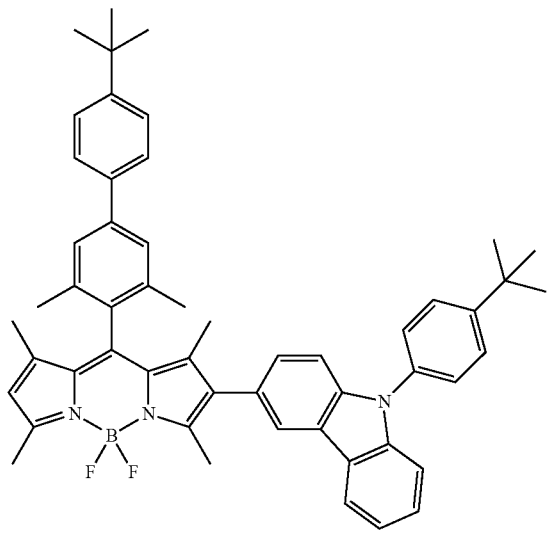
Compound 1-26
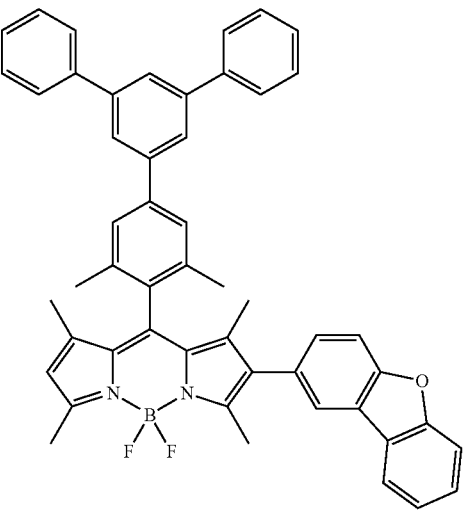

-continued
Compound 1-27
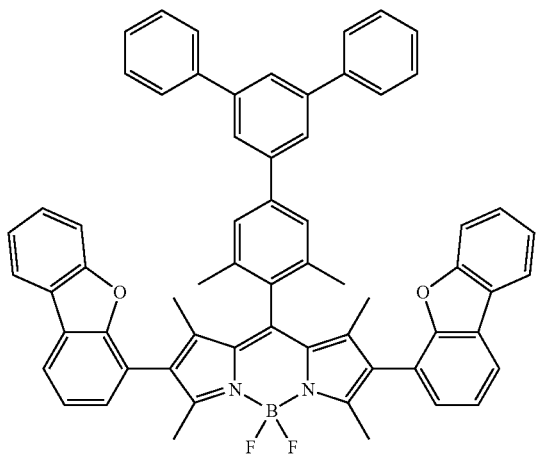
Compound 1-28
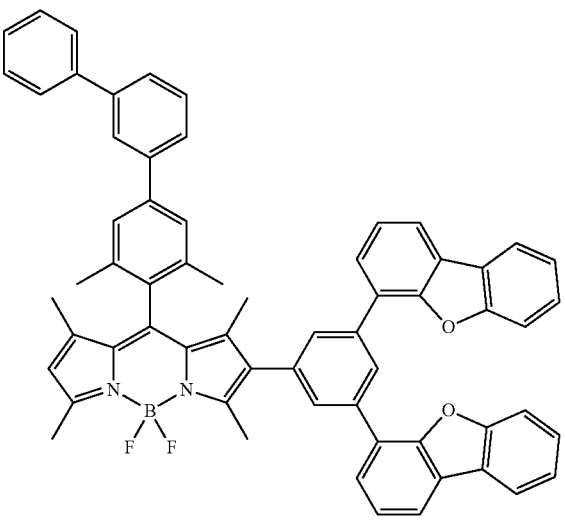
Compound 1-29
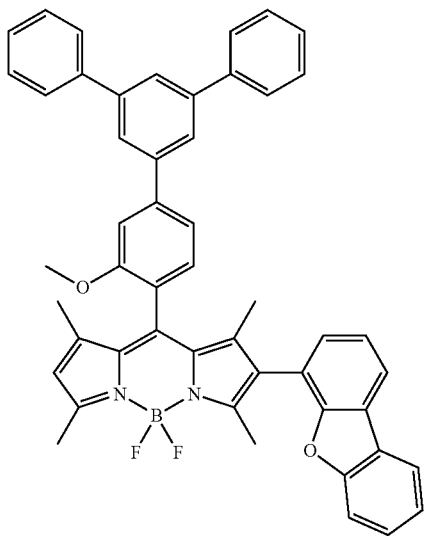
Compound 1-30
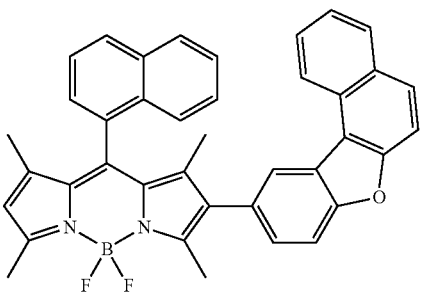
Compound 1-31
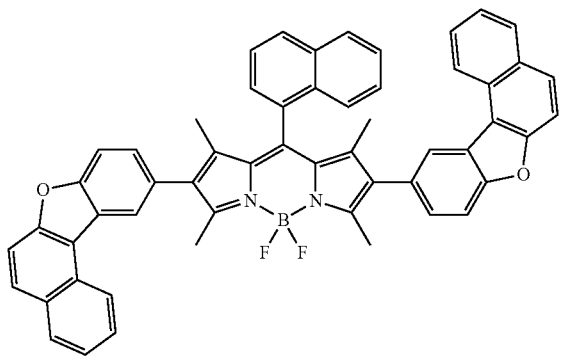
Compound 1-32
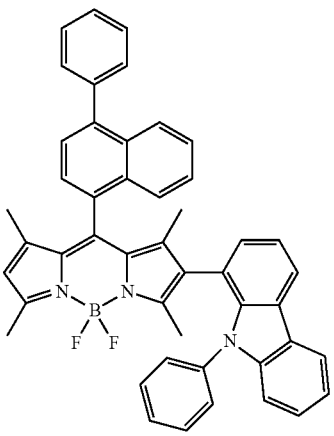

-continued
Compound 1-33
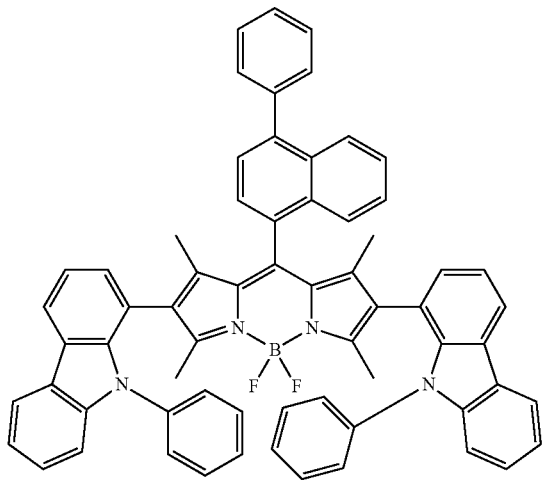
Compound 1-34
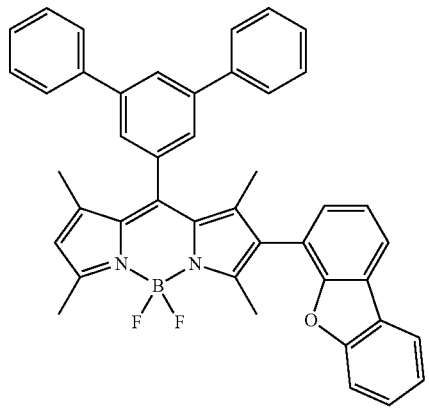
Compound 1-35
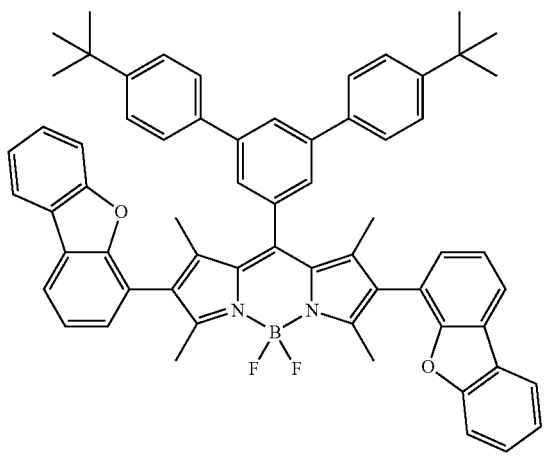
Compound 1-36
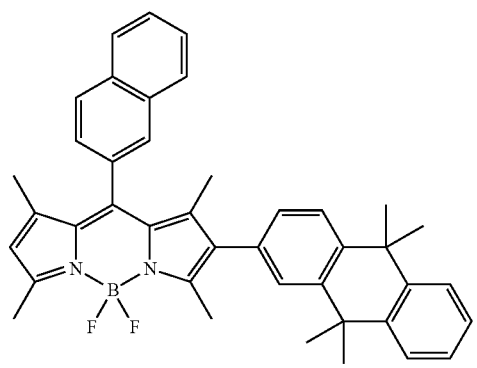
Compound 1-37
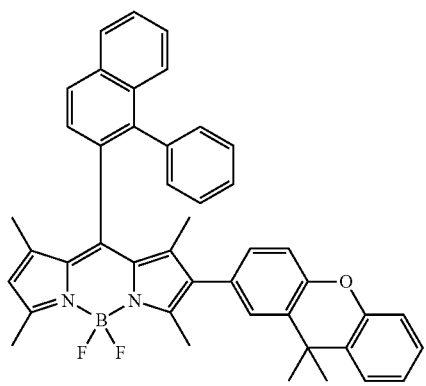
Compound 1-38
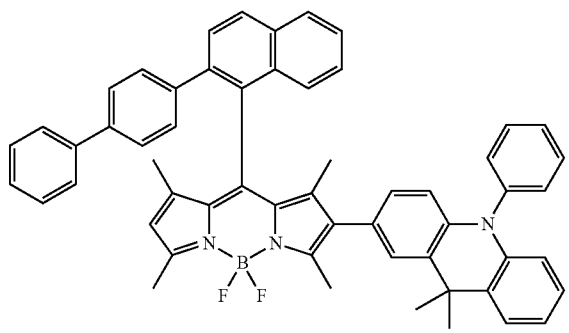

-continued
Compound 1-39
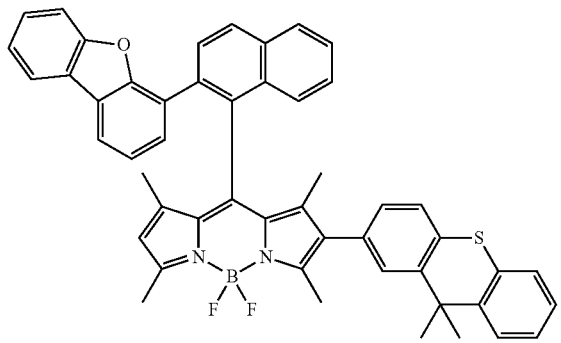
Compound 1-40
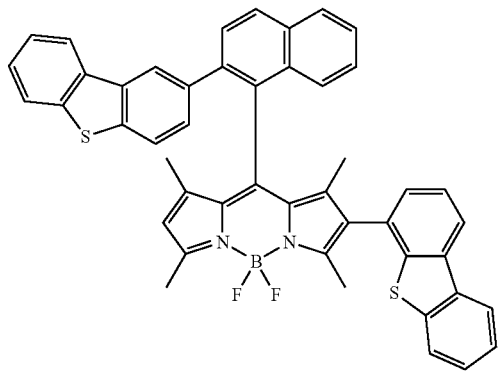
Compound 1-41
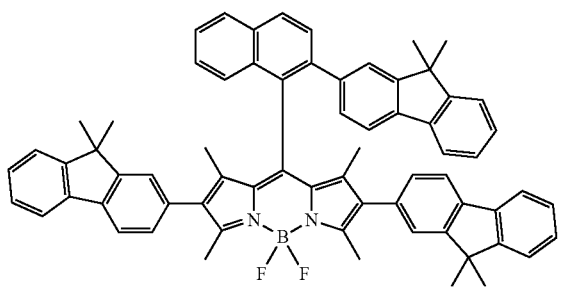
Compound 1-42
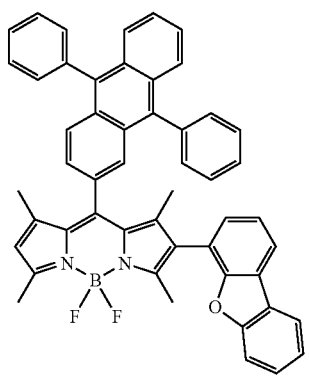
Compound 1-43
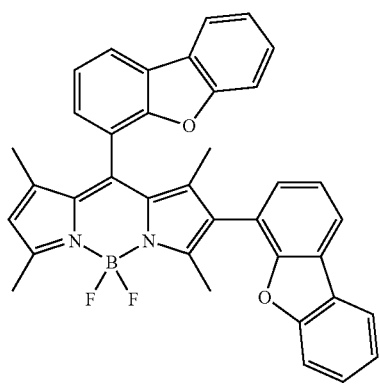
Compound 1-44
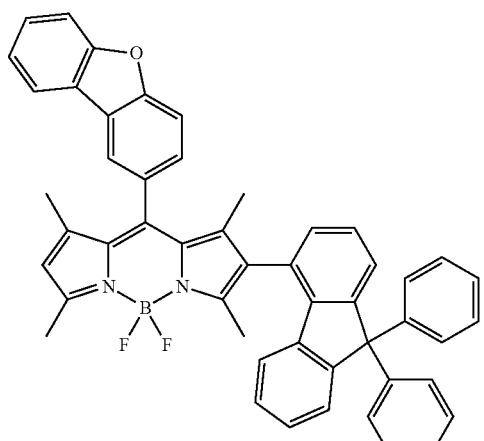
Compound 1-45
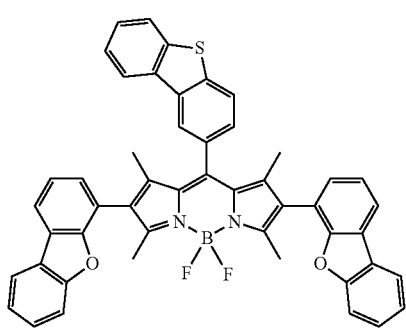
Compound 1-46
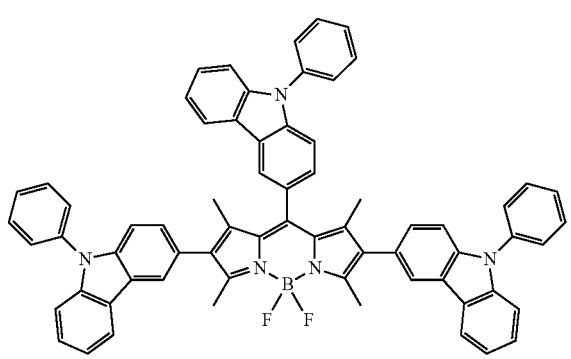

Compound 1-47
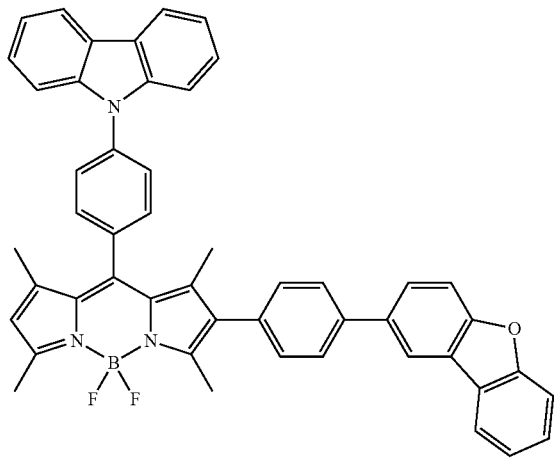
Compound 1-48
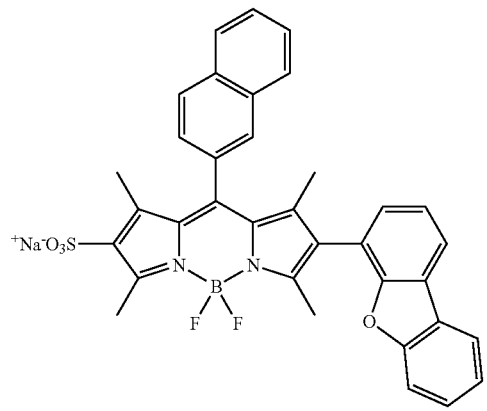
Compound 1-49
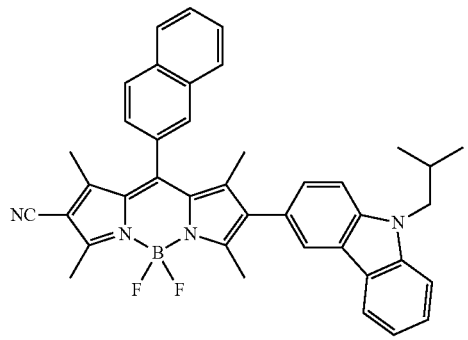
Compound 1-50
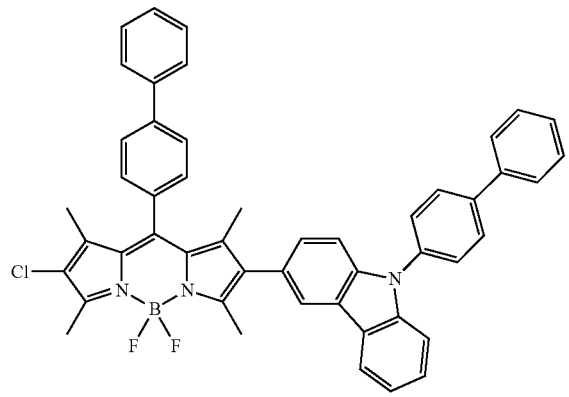
Compound 1-51
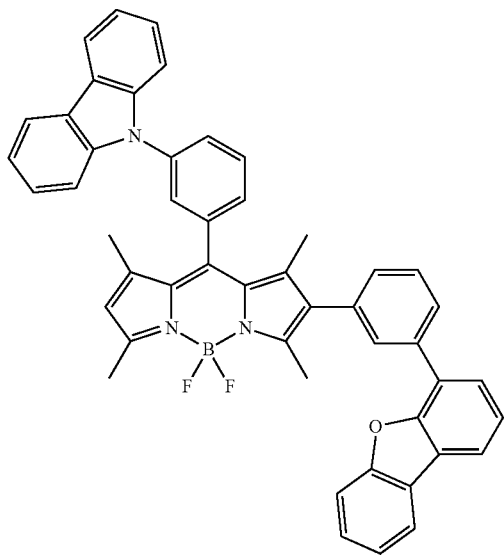
Compound 1-52
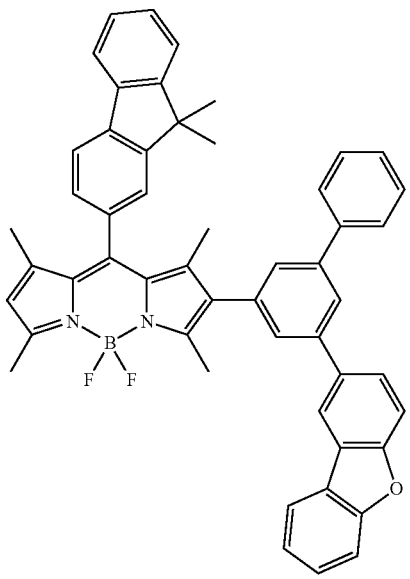

-continued
Compound 1-53
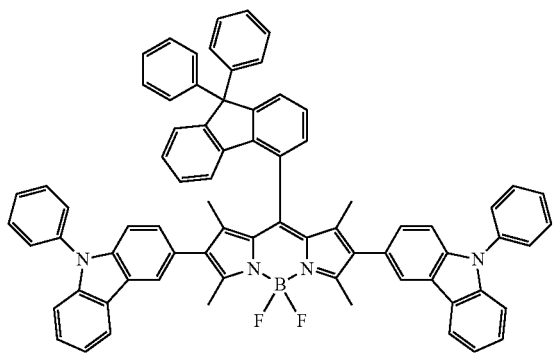
Compound 1-54
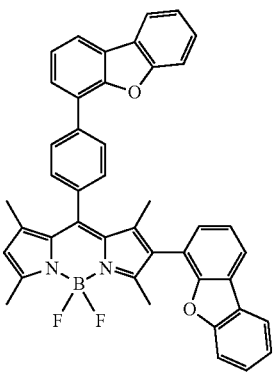
Compound 1-55
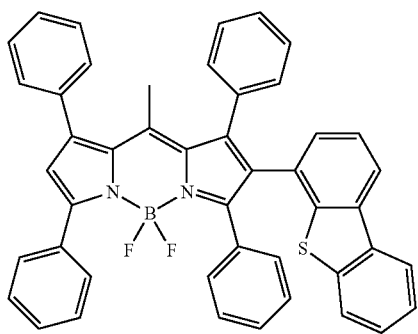
Compound 1-56
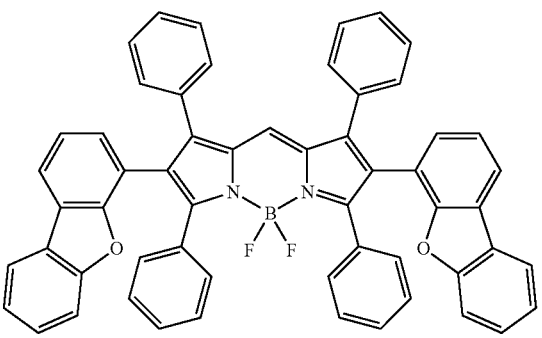
Compound 1-57
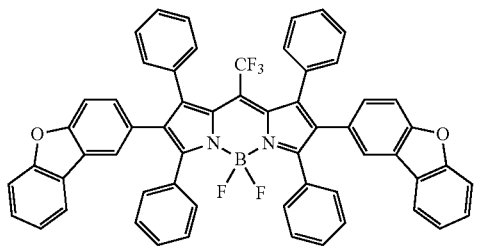
Compound 1-58
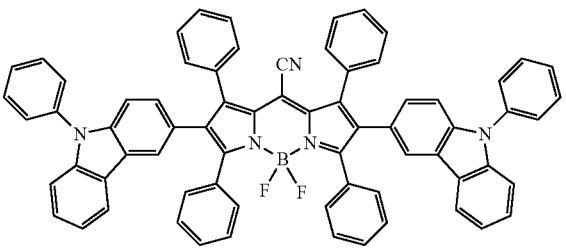
Compound 1-59
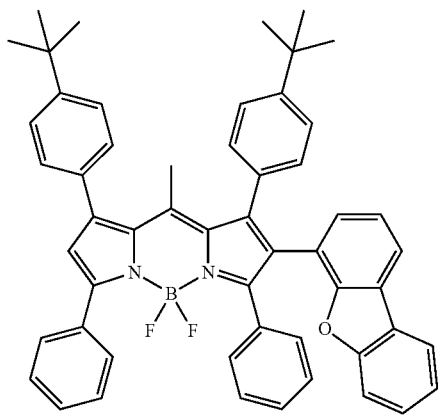
Compound 1-60
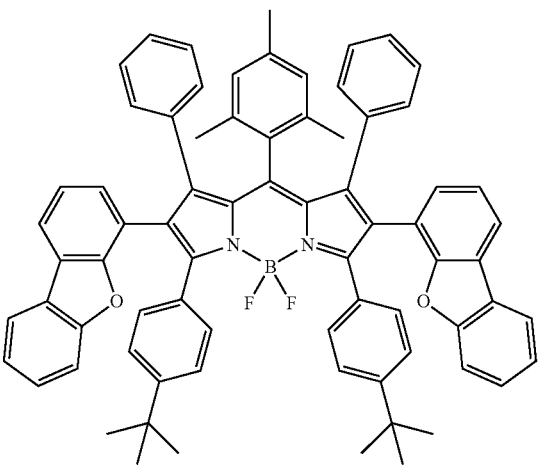

-continued
Compound 1-61
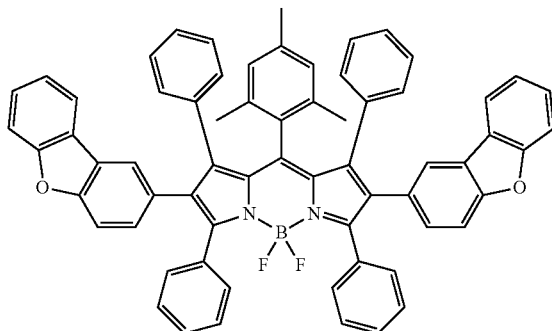
Compound 1-62
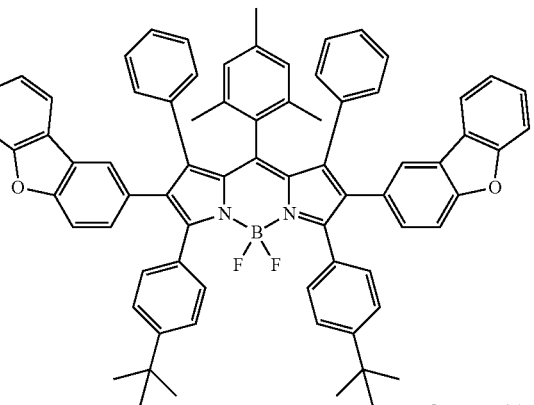
Compound 1-63
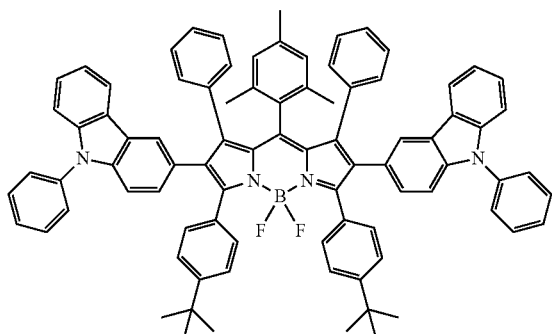
Compound 1-64
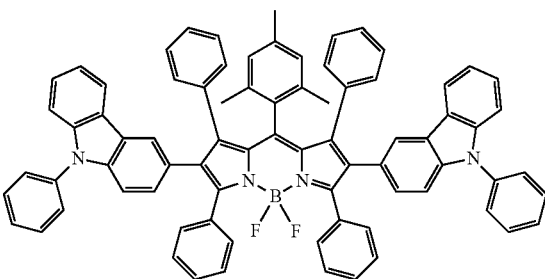
Compound 1-65
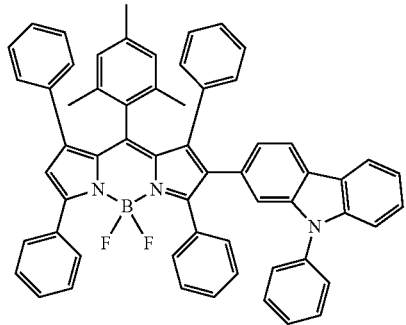
Compound 1-66
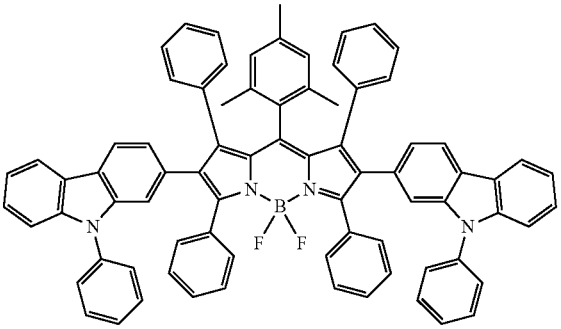
Compound 1-67
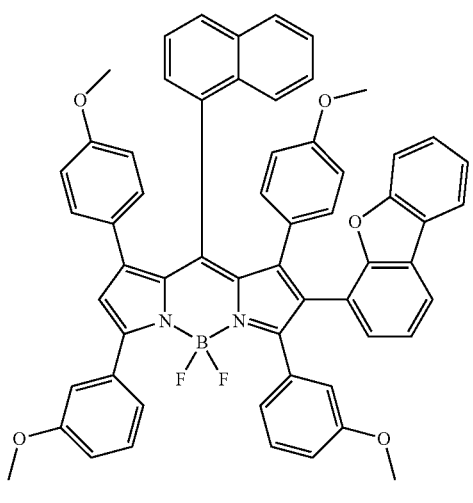
Compound 1-68
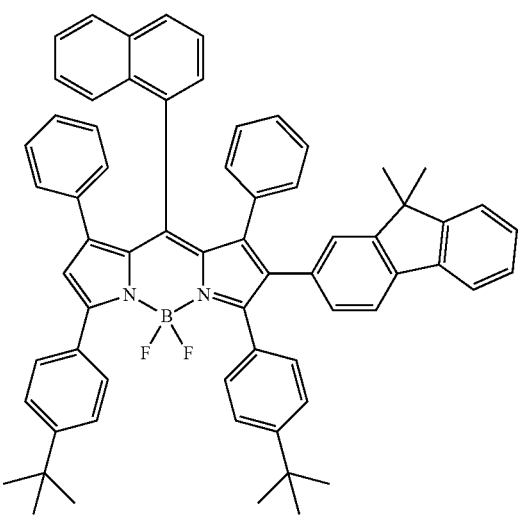

Compound 1-69
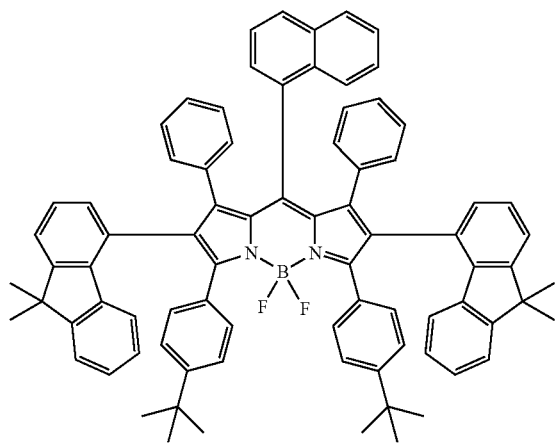
Compound 1-70
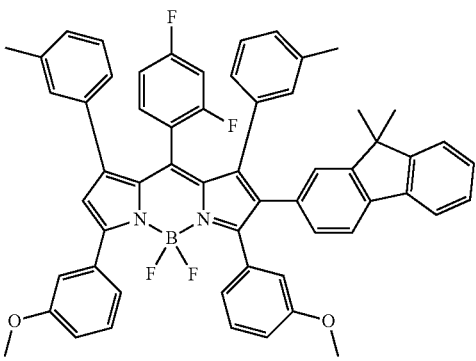
Compound 1-71
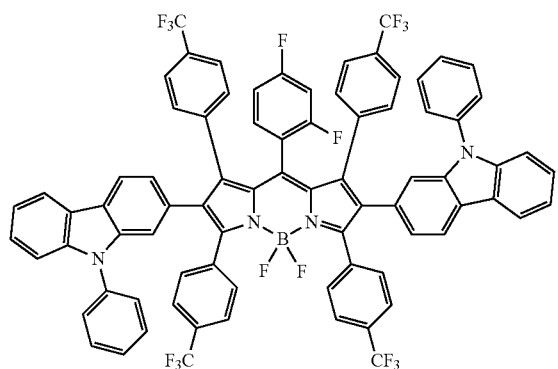
Compound 1-72
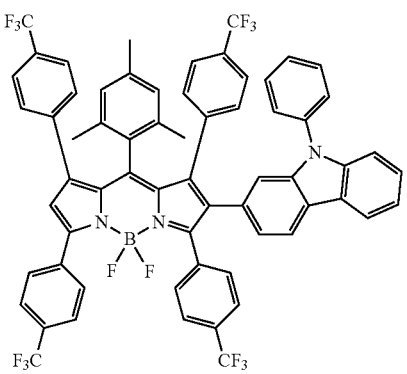
Compound 1-73
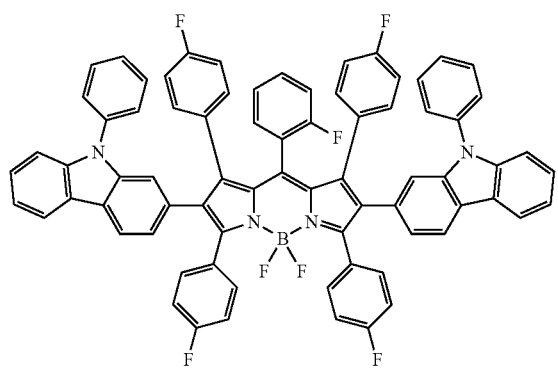
Compound 1-74
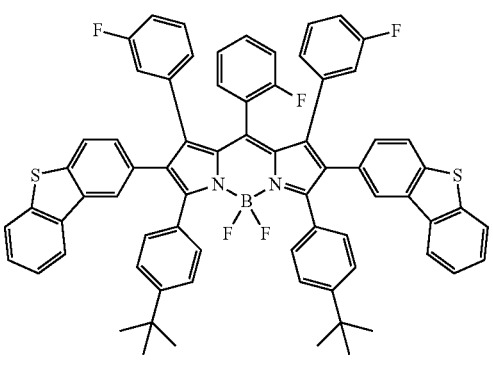
Compound 1-75
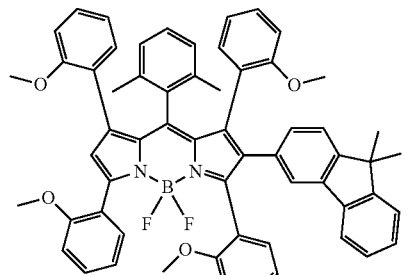
Compound 1-76
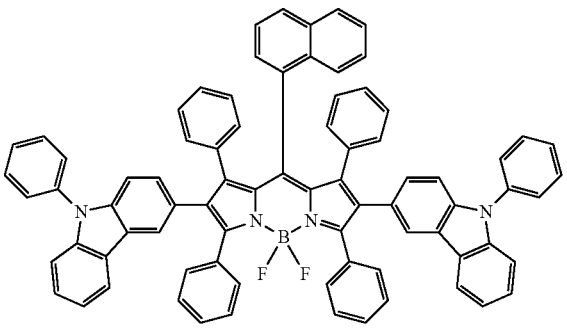

Compound 1-77
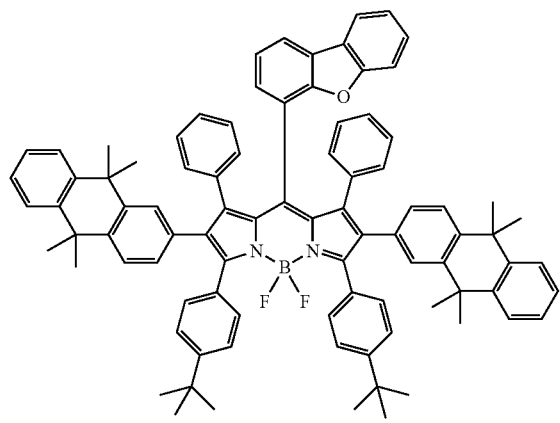
Compound 1-78
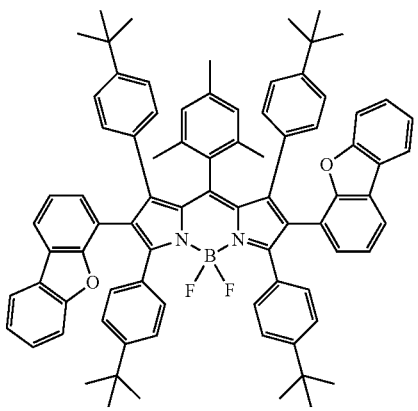
Compound 1-79
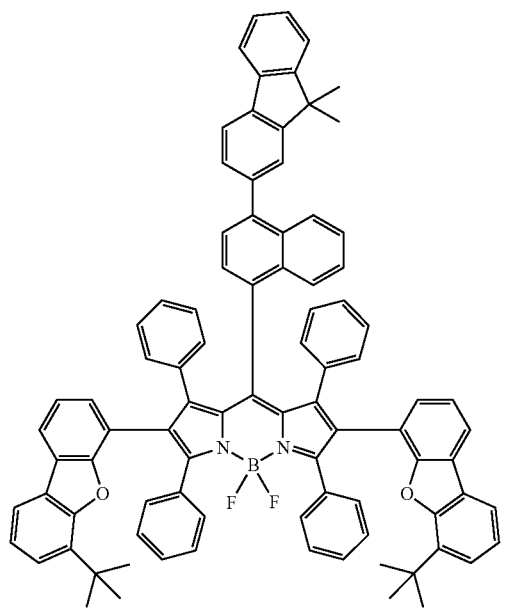
Compound 1-80
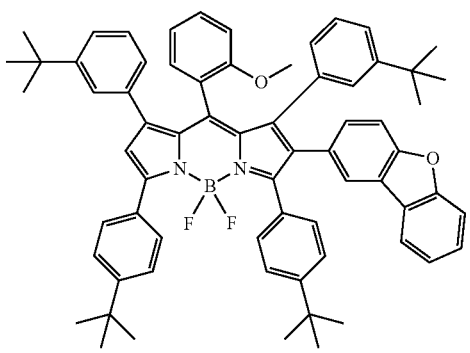
Compound 1-81
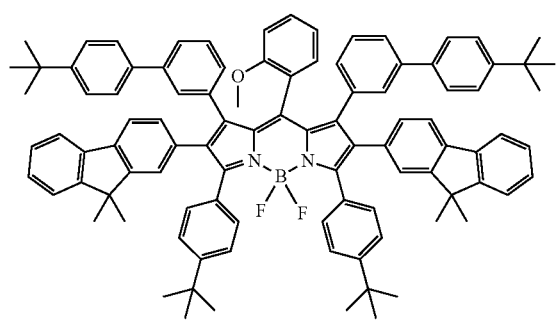
Compound 1-82
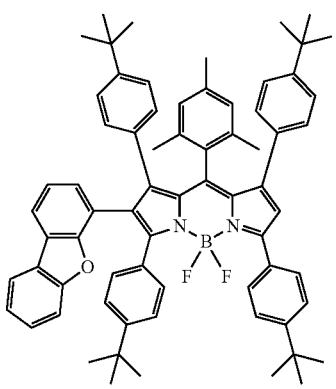

-continued
Compound 1-83
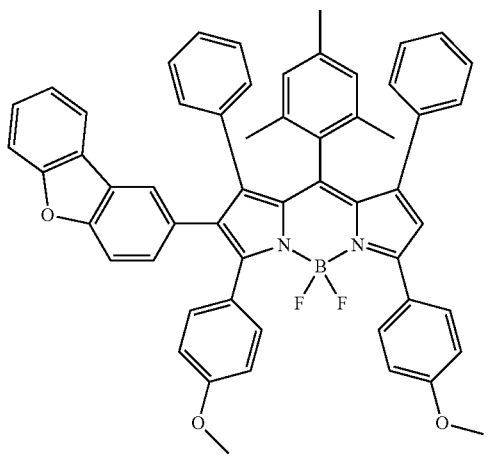
Compound 1-84
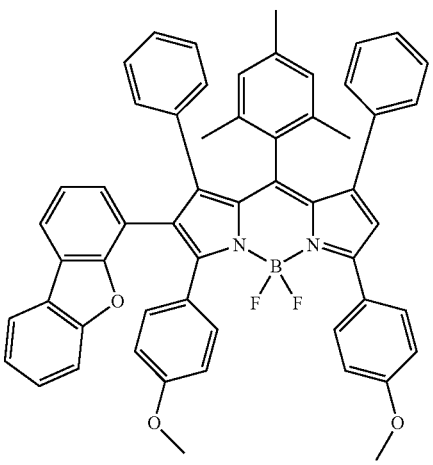
Compound 1-85
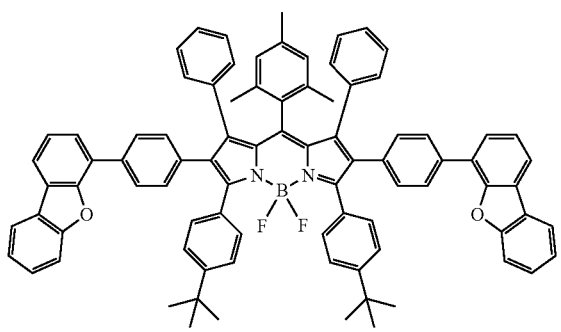
Compound 1-86
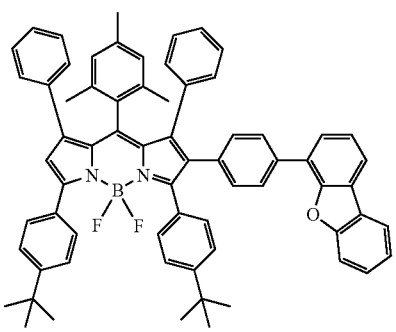
Compound 1-87
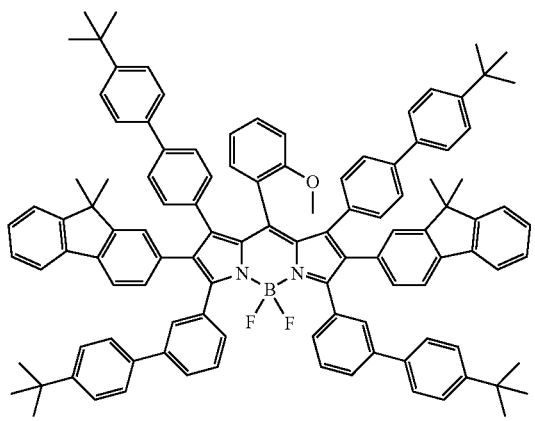
Compound 1-88
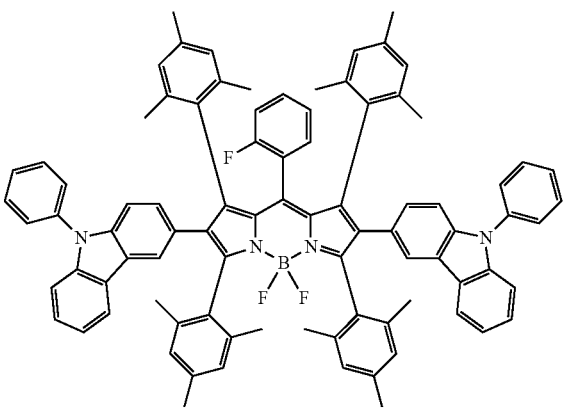
Compound 1-89
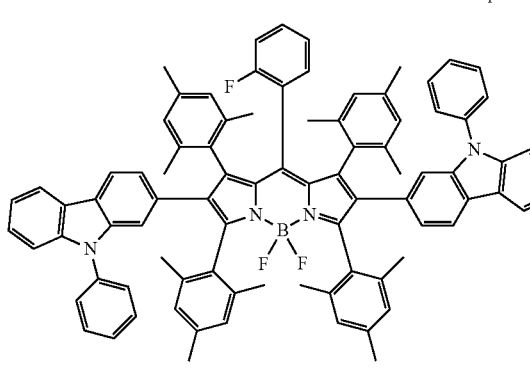
Compound 1-90
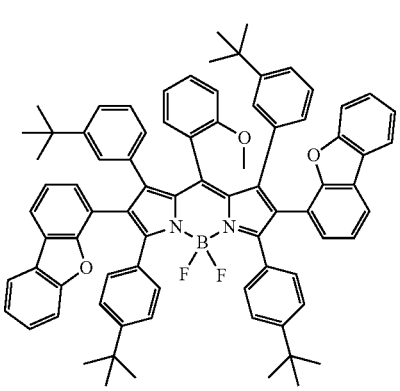

Compound 1-91
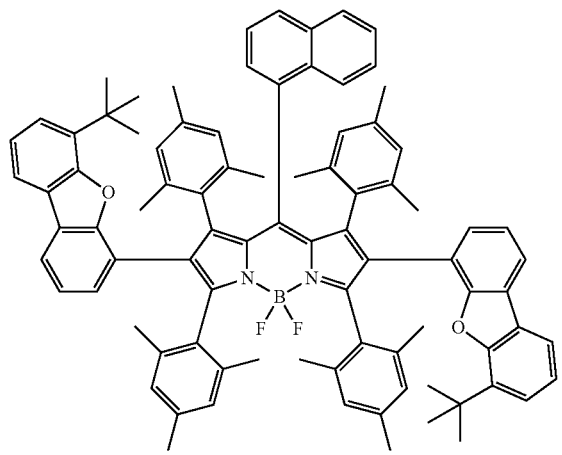
Compound 1-92
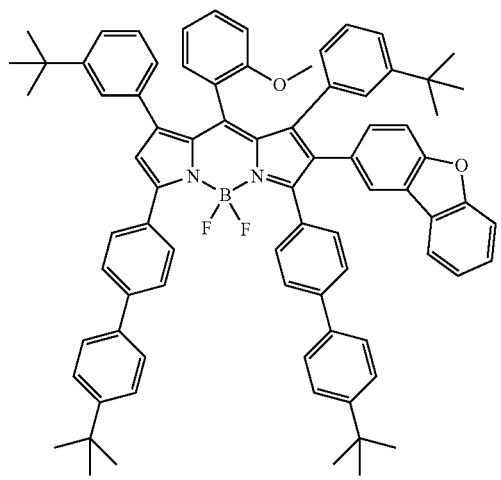
Compound 1-93
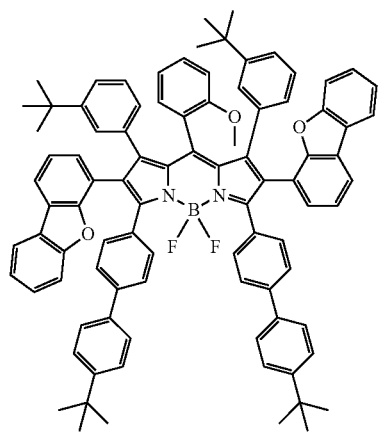
Compound 1-94
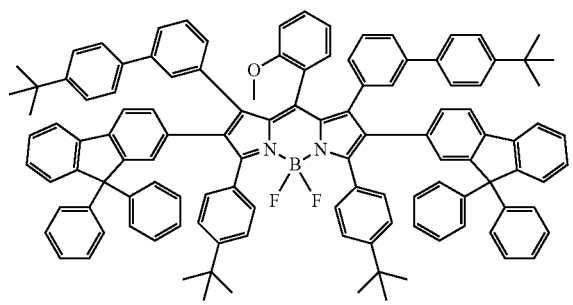
Compound 1-95
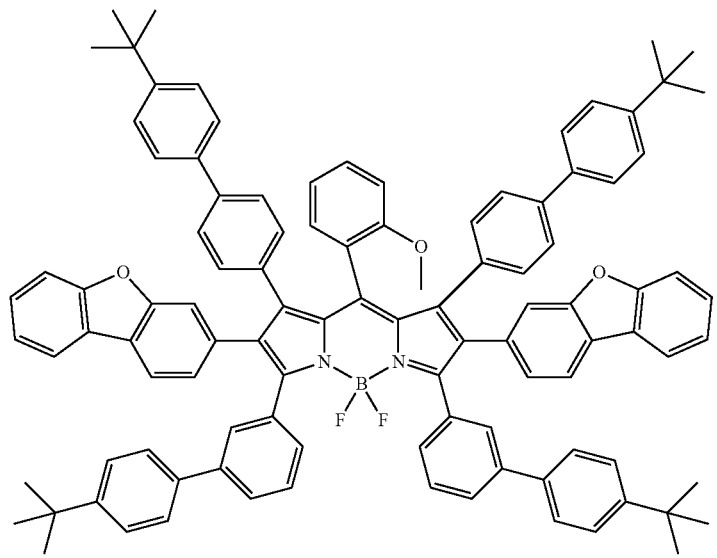

Compound 1-96
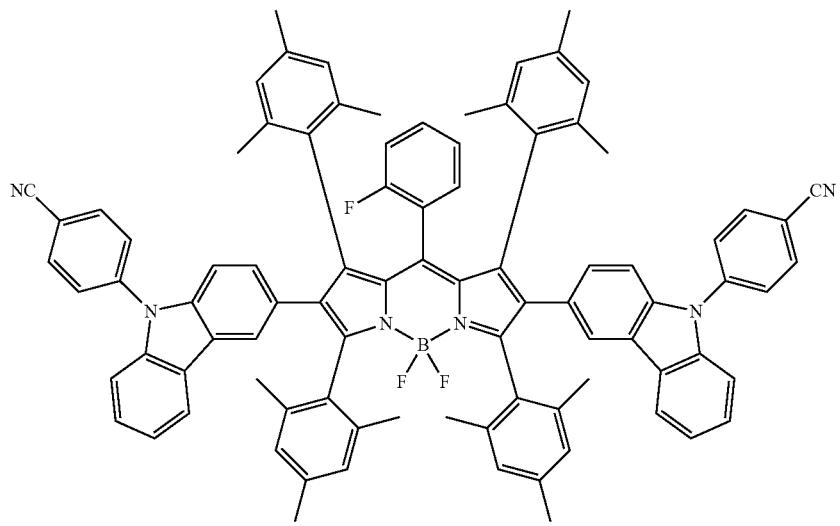
Compound 1-97
Compound 1-98
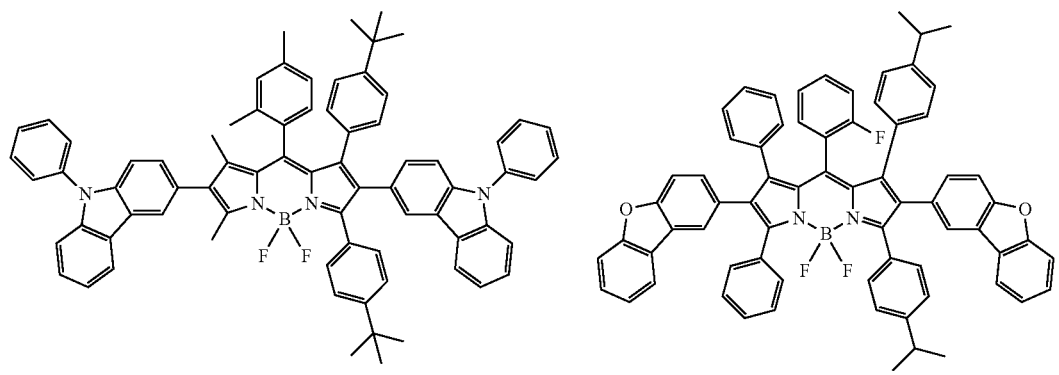
Compound 1-99
Compound 1-100
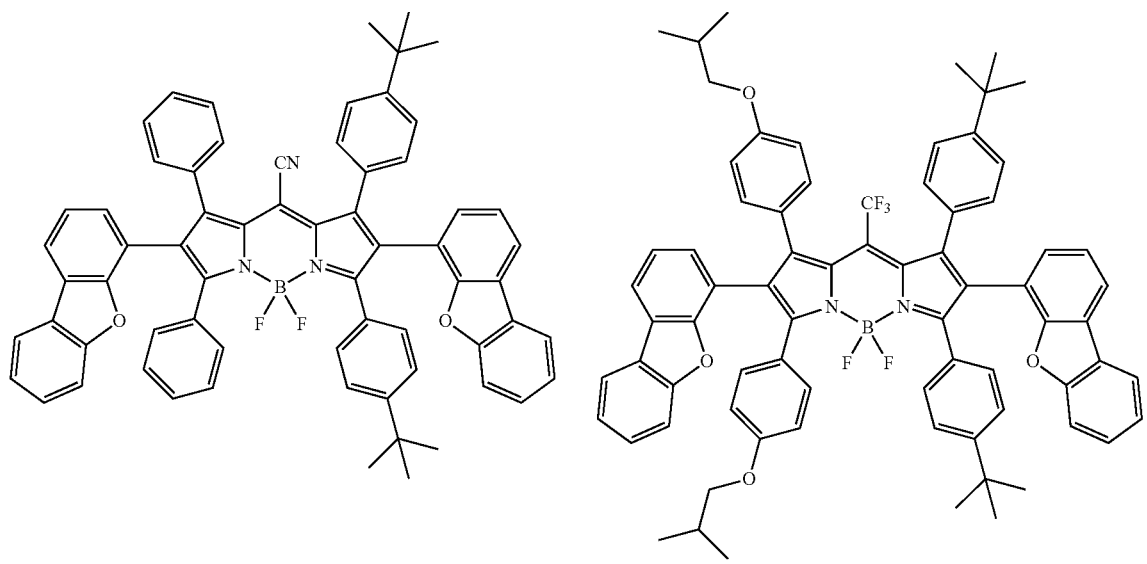

Compound 1-101
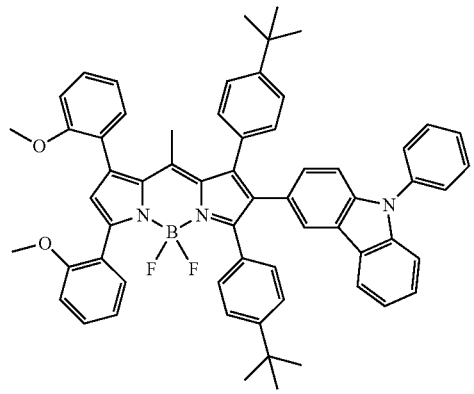
Compound 1-102
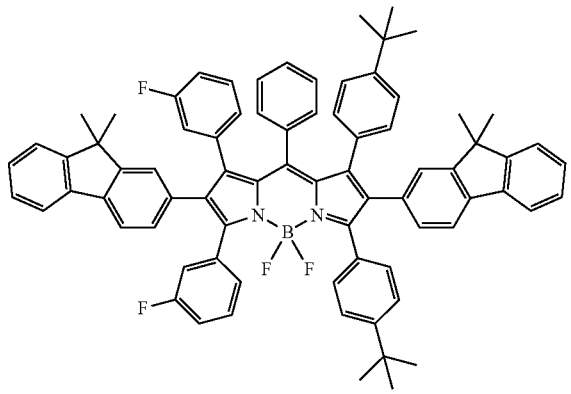
Compound 1-103
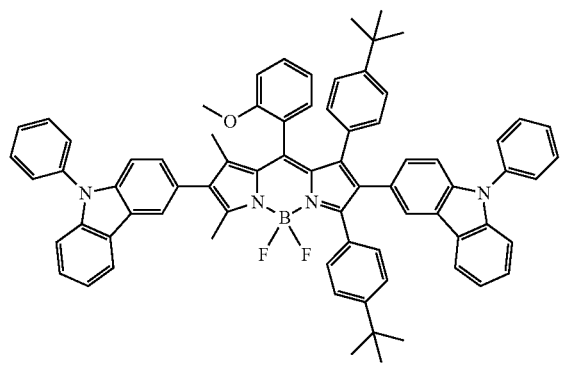
Compound 1-104
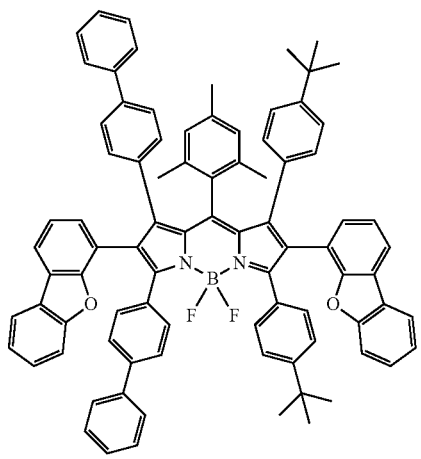
Compound 1-105
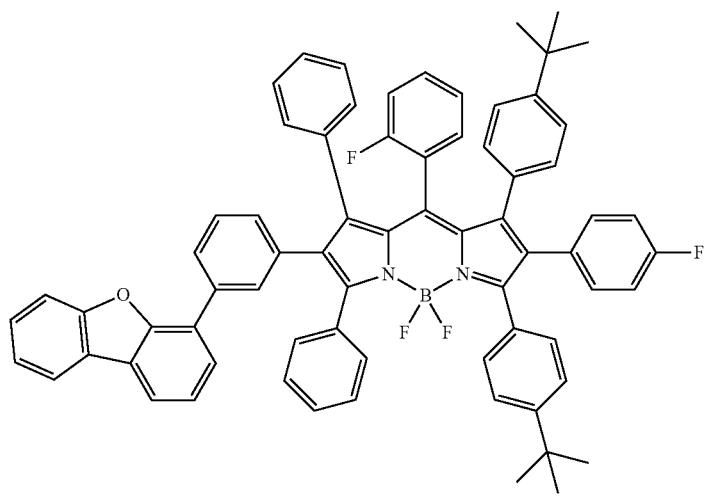

Compound 1-106
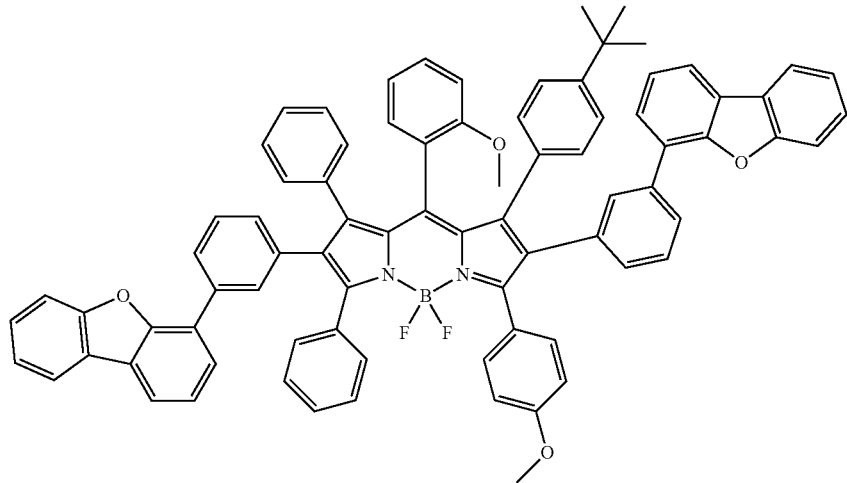
Compound 1-107
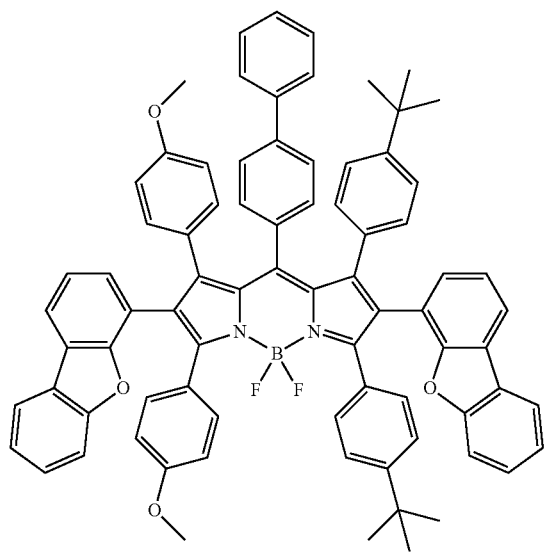
Compound 1-108
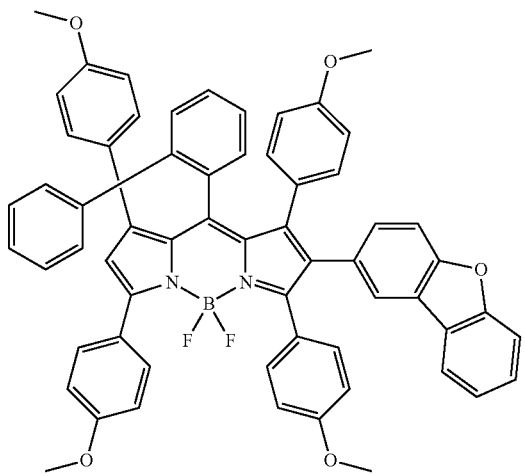
Compound 1-109
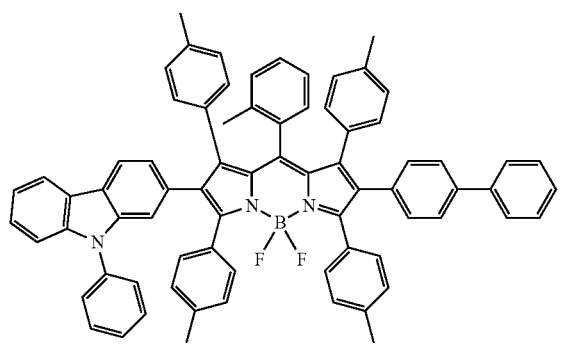
Compound 1-110
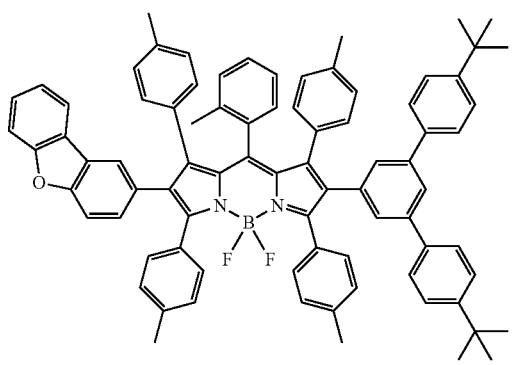

Compound 1-111
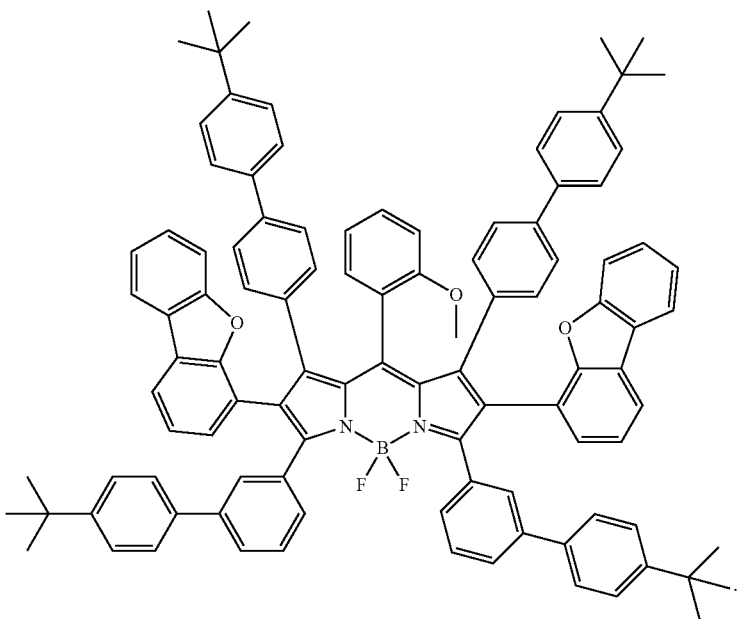
11. A color conversion film comprising: a resin matrix; and the compound of claim 1, which is dispersed in the resin matrix.
12. A backlight unit comprising the color conversion film of claim 11.
13. A display device comprising the backlight unit of claim 12.
* * * * *